United States Patent
Alchemy et al.

(10) Patent No.: US 11,461,848 B1
(45) Date of Patent: Oct. 4, 2022

(54) METHODS OF OBTAINING HIGH ACCURACY IMPAIRMENT RATINGS AND TO ASSIST DATA INTEGRITY IN THE IMPAIRMENT RATING PROCESS

(71) Applicant: Alchemy Logic Systems, Inc., Santa Rosa, CA (US)

(72) Inventors: John William Alchemy, Santa Rosa, CA (US); Daniel Robert Brown, Santa Rosa, CA (US); Daniel Ryan Penn, Santa Rosa, CA (US); Joshua Ryan Moore, Santa Rosa, CA (US); Jerry Lee Artz, St. Paul, MN (US); Anne Elise Weilepp, Santa Rosa, CA (US); Marten Lee Thompson, Spicer, MN (US)

(73) Assignee: Alchemy Logic Systems, Inc., Santa Rosa, CA (US)

( * ) Notice: Subject to any disclaimer, the term of this patent is extended or adjusted under 35 U.S.C. 154(b) by 672 days.

(21) Appl. No.: 14/996,067

(22) Filed: Jan. 14, 2016

Related U.S. Application Data

(60) Provisional application No. 62/103,479, filed on Jan. 14, 2015.

(51) Int. Cl.
  *G06Q 40/08* (2012.01)
  *G16H 10/60* (2018.01)

(52) U.S. Cl.
  CPC ............. *G06Q 40/08* (2013.01); *G16H 10/60* (2018.01)

(58) Field of Classification Search
  None
  See application file for complete search history.

(56) References Cited

U.S. PATENT DOCUMENTS

| | | |
|---|---|---|
| 4,916,611 A | 4/1990 | Doyle, Jr. et al. |
| 4,987,538 A | 1/1991 | Johnson et al. |

(Continued)

FOREIGN PATENT DOCUMENTS

| | | | |
|---|---|---|---|
| CA | 2707207 A1 * | 6/2009 | ........... G06Q 10/087 |
| WO | WO2008006117 A2 | 1/2008 | |
| WO | 2018224937 A1 | 12/2018 | |

OTHER PUBLICATIONS

Park, Y., & Butler, R. J. (2000). Permanent Partial Disability Awards and Wage Loss. Journal of Risk and Insurance, 67(3), 331. Retrieved from https://dialog.proquest.com/professional/docview/769439682?accountid=142257 (Year: 2000).*

(Continued)

*Primary Examiner* — Lena Najarian
(74) *Attorney, Agent, or Firm* — Haverstock & Owens, A Law Corporation

(57) ABSTRACT

A method and system teaches unique applications of logic and statistics to medical processes to obtain substantially improved accuracy in the measurement of a examinee's pathology due to an injury. The method and the system incorporate strict protocols, or "Administrative Rule Sets" to direct the examination for the purpose of obtaining an optimal data set, from which a rating of the impairment due to the pathology resulting from an injury may be determined. Additionally, within this method and system, a statistical analysis may additionally assist in obtaining an improved accuracy of impairment ratings. Consequently, the errors in the impairment rating presently carried forward through the disability, care and compensation phases of the process are now avoided.

6 Claims, 34 Drawing Sheets

(56) References Cited

U.S. PATENT DOCUMENTS

| | | |
|---|---|---|
| 5,182,705 A | 1/1993 | Barr et al. |
| 5,367,675 A | 11/1994 | Cheng et al. |
| 5,517,405 A | 5/1996 | McAndrew et al. |
| 5,544,044 A | 8/1996 | Leatherman |
| 5,613,072 A | 3/1997 | Hammond |
| 5,778,345 A | 7/1998 | McCartney |
| 5,911,132 A | 6/1999 | Sloane |
| 5,957,227 A | 9/1999 | Besson |
| 6,003,007 A | 12/1999 | DiRienzo |
| 6,065,000 A | 5/2000 | Jensen |
| 6,604,080 B1 | 8/2003 | Kern |
| 6,810,391 B1 | 10/2004 | Birkhoelzer et al. |
| 6,954,730 B2 | 10/2005 | Lau et al. |
| 7,337,121 B1 | 2/2008 | Beinet |
| 7,401,056 B2 | 7/2008 | Kam |
| 7,440,904 B2 | 10/2008 | Hasan et al. |
| 7,475,020 B2 | 1/2009 | Hasan et al. |
| 7,509,264 B2 | 3/2009 | Hasan et al. |
| 7,630,911 B2 | 12/2009 | Kay |
| 7,630,913 B2 | 12/2009 | Kay |
| 7,707,046 B2 | 4/2010 | Kay |
| 7,707,047 B2 | 4/2010 | Hasan et al. |
| 7,778,849 B1 | 8/2010 | Hutton |
| 7,813,944 B1 | 10/2010 | Luk |
| 7,870,011 B2 | 1/2011 | Kay |
| 7,904,309 B2 | 3/2011 | Malone |
| 7,930,190 B1 | 4/2011 | Milanovich |
| 7,949,550 B2 | 5/2011 | Kay |
| 7,970,865 B2 | 6/2011 | DeCesare et al. |
| 8,019,624 B2 | 9/2011 | Malone |
| 8,041,585 B1 | 10/2011 | Binns et al. |
| 8,065,163 B2 | 11/2011 | Morita et al. |
| 8,069,066 B2 | 11/2011 | Stevens et al. |
| 8,185,410 B2 | 5/2012 | Brigham |
| 8,301,575 B2 | 10/2012 | Bonnet et al. |
| 8,346,573 B2 | 1/2013 | Glimp et al. |
| 8,489,413 B1 | 7/2013 | Larson et al. |
| 8,489,424 B2 | 7/2013 | Hasan et al. |
| 8,510,134 B1* | 8/2013 | Sweat ................ G06Q 10/10 705/2 |
| 8,527,303 B2 | 9/2013 | Kay |
| 8,615,409 B1 | 12/2013 | McKown |
| 8,630,878 B1* | 1/2014 | Kravets ............... G06Q 40/08 705/4 |
| 8,725,524 B2 | 5/2014 | Fano |
| 8,725,538 B2 | 5/2014 | Kay |
| 8,751,252 B2 | 6/2014 | Chamberlain |
| 8,751,263 B1 | 6/2014 | Cave et al. |
| 8,751,266 B2 | 6/2014 | Stang |
| 8,775,216 B1 | 7/2014 | Amick et al. |
| 8,864,663 B1 | 10/2014 | Kahn et al. |
| 8,868,768 B2 | 10/2014 | Sokoryansky |
| 8,888,697 B2 | 11/2014 | Bowman et al. |
| 8,900,141 B2 | 12/2014 | Smith et al. |
| 8,910,278 B2 | 12/2014 | Davne et al. |
| 8,930,225 B2 | 1/2015 | Morris |
| 8,959,027 B2 | 1/2015 | Kusens |
| 8,954,339 B2 | 2/2015 | Schaffer |
| 9,002,719 B2 | 4/2015 | Tofte |
| 9,015,055 B2 | 4/2015 | Tirinato et al. |
| 9,020,828 B2 | 4/2015 | Heidenreich |
| 9,710,600 B1 | 7/2017 | Dunleavy |
| 2001/0053984 A1 | 12/2001 | Joyce |
| 2002/0069219 A1 | 6/2002 | Larkin |
| 2002/0077849 A1 | 6/2002 | Baruch |
| 2004/0044546 A1 | 3/2004 | Moore |
| 2005/0060184 A1* | 3/2005 | Wahlbin ............. G06Q 40/02 705/2 |
| 2005/0177403 A1 | 8/2005 | Johnson |
| 2005/0256744 A1 | 11/2005 | Rohde |
| 2006/0161456 A1 | 7/2006 | Baker |
| 2006/0287879 A1 | 12/2006 | Malon |
| 2007/0118406 A1 | 5/2007 | Killin |
| 2007/0250352 A1 | 10/2007 | Tawil |
| 2008/0154672 A1 | 6/2008 | Skedsvold |
| 2008/0183797 A1 | 7/2008 | Soon-Shiong |
| 2009/0099875 A1* | 4/2009 | Koenig ................ G06Q 40/08 705/3 |
| 2010/0042435 A1 | 2/2010 | Kay |
| 2010/0106520 A1 | 4/2010 | Kay |
| 2010/0106526 A1 | 4/2010 | Kay |
| 2010/0114609 A1 | 5/2010 | Duffy, Jr. et al. |
| 2010/0217624 A1 | 8/2010 | Kay |
| 2010/0240963 A1 | 9/2010 | Brighman |
| 2011/0077980 A1 | 3/2011 | Kay |
| 2011/0077981 A1 | 3/2011 | Kay |
| 2011/0145012 A1 | 6/2011 | Nightingale |
| 2011/0161115 A1 | 6/2011 | Hampton |
| 2011/0257919 A1 | 10/2011 | Reiner |
| 2011/0257993 A1 | 10/2011 | Shahani |
| 2011/0313785 A1 | 12/2011 | Lash |
| 2011/0313912 A1 | 12/2011 | Teutsch |
| 2012/0022884 A1* | 1/2012 | Chillemi ............. A61B 5/1121 705/2 |
| 2012/0102026 A1 | 4/2012 | Fortune |
| 2012/0130751 A1 | 5/2012 | McHugh |
| 2012/0232924 A1 | 9/2012 | Bingham |
| 2012/0278095 A1 | 11/2012 | Homchowdhury |
| 2013/0024214 A1 | 1/2013 | Schoen et al. |
| 2014/0052465 A1 | 2/2014 | Madan |
| 2014/0058763 A1 | 2/2014 | Zizzamia |
| 2014/0073486 A1 | 3/2014 | Ahmed |
| 2014/0136216 A1 | 5/2014 | Beebe |
| 2014/0172439 A1 | 6/2014 | Conway et al. |
| 2014/0201213 A1 | 7/2014 | Jackson |
| 2014/0278479 A1 | 9/2014 | Wang et al. |
| 2014/0303993 A1 | 10/2014 | Florian |
| 2015/0019234 A1 | 1/2015 | Cooper |
| 2015/0221057 A1 | 8/2015 | Raheja et al. |
| 2015/0235334 A1 | 8/2015 | Wang et al. |
| 2015/0278462 A1 | 10/2015 | Smoley et al. |
| 2015/0324523 A1 | 11/2015 | Parthasarathy et al. |
| 2016/0063197 A1 | 3/2016 | Kumetz |
| 2016/0125544 A1 | 5/2016 | Edwards |
| 2016/0292371 A1 | 10/2016 | Mhimiri |
| 2017/0154374 A1 | 6/2017 | Iglesias |
| 2017/0177810 A1 | 6/2017 | Fulton |
| 2017/0228517 A1 | 8/2017 | Saliman |
| 2017/0255754 A1 | 9/2017 | Allen |
| 2017/0316424 A1 | 11/2017 | Messana |
| 2017/0352105 A1 | 12/2017 | Billings |
| 2018/0025334 A1 | 1/2018 | Pourfallah |
| 2018/0279919 A1 | 10/2018 | Bansbach |
| 2020/0126645 A1 | 4/2020 | Robbins |
| 2020/0279622 A1 | 9/2020 | Heywood |
| 2020/0286600 A1 | 9/2020 | De Brouwer |

OTHER PUBLICATIONS

In B. Pfaffenberger, Webster's new World&Trade; Computer Dictionary(10th ed). Houghtpon Mifflin Harcourt, Credo reference:https://search.credoreference.com/content/entry/webster.com/database(year 2003).

"Physician's Guide to Medical Practice in the California Worker's Compensation System", 2016, State of California Department of Industrial Relations Division of Worker's Compensation, 4th ed., all pages. (Year 2016).

In B. Pfaffenberger, Webster's new World&Trade; Computer Dictionary (10th ed.) Houghton Mifflin Harcourt, Credo reference: https://search.credoreference.com/content/entry/webster.com/database (year 2003).

Hakkinen, Arja, et al. "Muscle strength, pain, and disease activity explain individual subdimensions of the Health Assessment Questionaire disability index, especially in women with rheumatoid arthritis." Annals of the rheumatic diseases 65.1 (2006): 30-34. (Year: 2006).

Rondinelli, Robert D., Guides to the Evaluation of Permanent Impairment, 2008 Sixth Edition, American Medical Association, pp. 25-26.

(56) References Cited

OTHER PUBLICATIONS

Cocchiarella, Linda and Andersson, Gunnar B.J., Guides to the Evaluation of Permanant Impairment, 2001 Fifth Edition, American Medical Association, pp. 11-12.

* cited by examiner

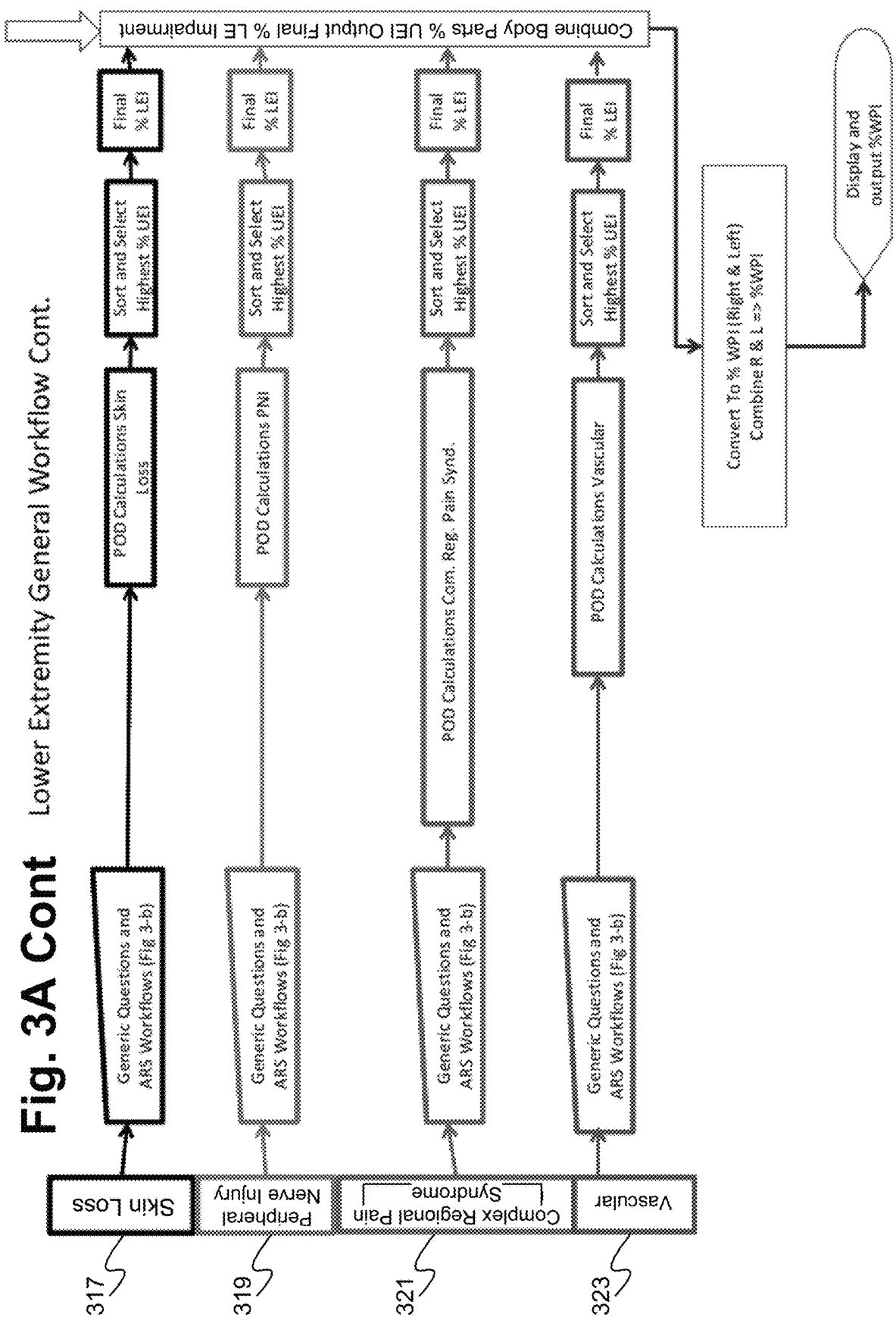
Fig. 3A Cont    Lower Extremity General Workflow Cont.

Fig. 3C Columns Represent ARS for POD Calculators Fig 3a

| | Limb Length Discrepancy | Gait Derangement | Muscle Atrophy | Muscle Strength | ROM Analysis | Arthritis DJD | Amputation | Diagnosis Based Estimates | Skin Loss | Peripheral Nerve Injury | Complex Regional Pain Synd. | Vascular |
|---|---|---|---|---|---|---|---|---|---|---|---|---|
| Vascular | | X | | | | | | | | | X | |
| Complex Regional Pain Synd. | | X | X | O | O | | | | | X | | X |
| Peripheral Nerve Injury | | X | X | X | | | | | | | X | |
| Skin Loss | | X | | | | | | | | | | |
| Diagnosis Based Estimates | | X | X | X | X | | | | | | | |
| Amputation | X | X | X | | | | | | | | | |
| Arthritis DJD | | X | X | X | X | | | | | | | |
| ROM Analysis | | X | X | X | | X | | X | | | O | |
| Muscle Strength | | X | X | | X | X | X | X | | X | O | |
| Muscle Atrophy | | X | | X | X | X | X | X | | X | X | |
| Gait Derangement | X | | X | X | X | X | X | X | X | X | X | X |
| Limb Length Discrepancy | | X | | | | | X | | | | | |

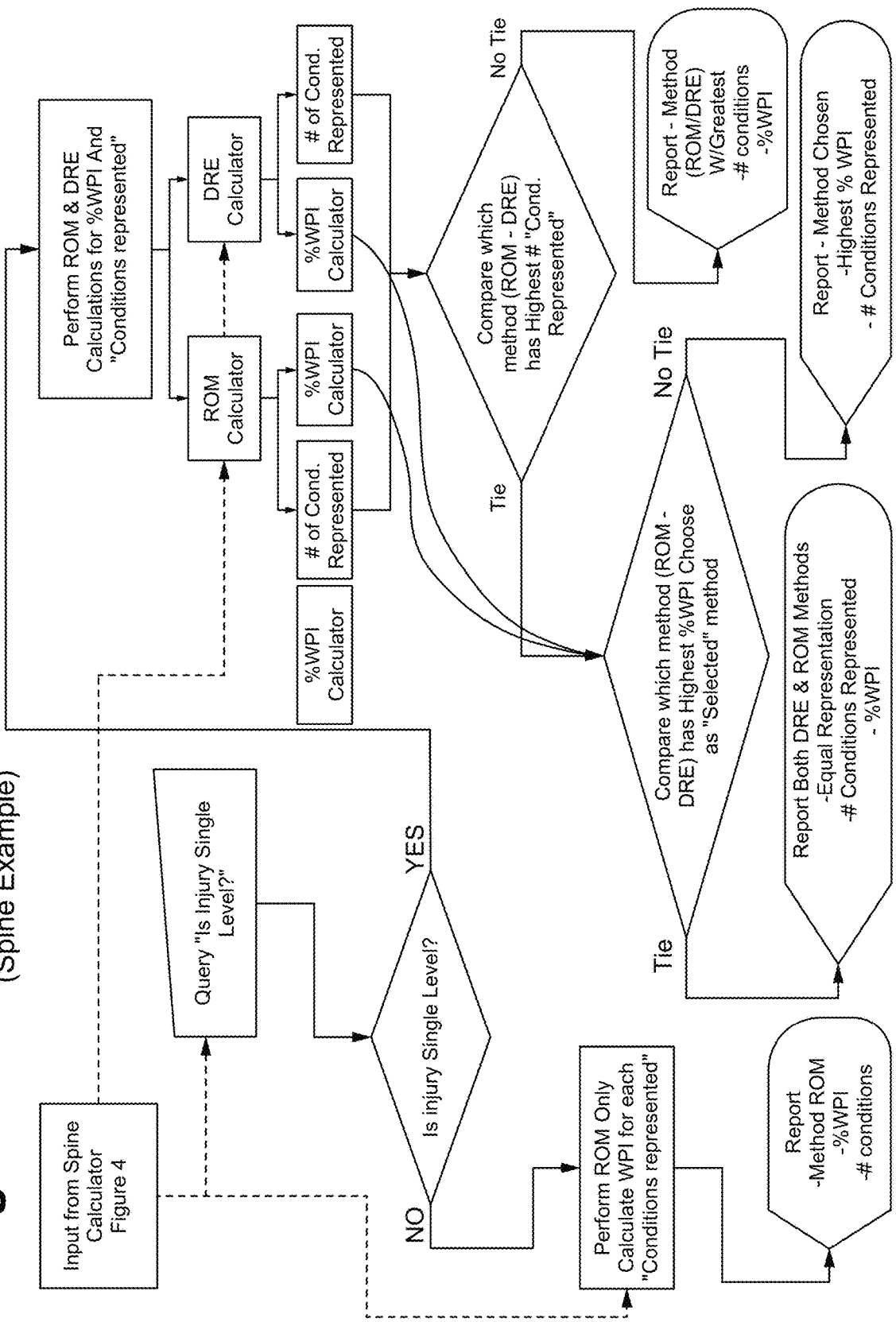
Fig. 9   Comparison of ROM and DRE (Spine Example)

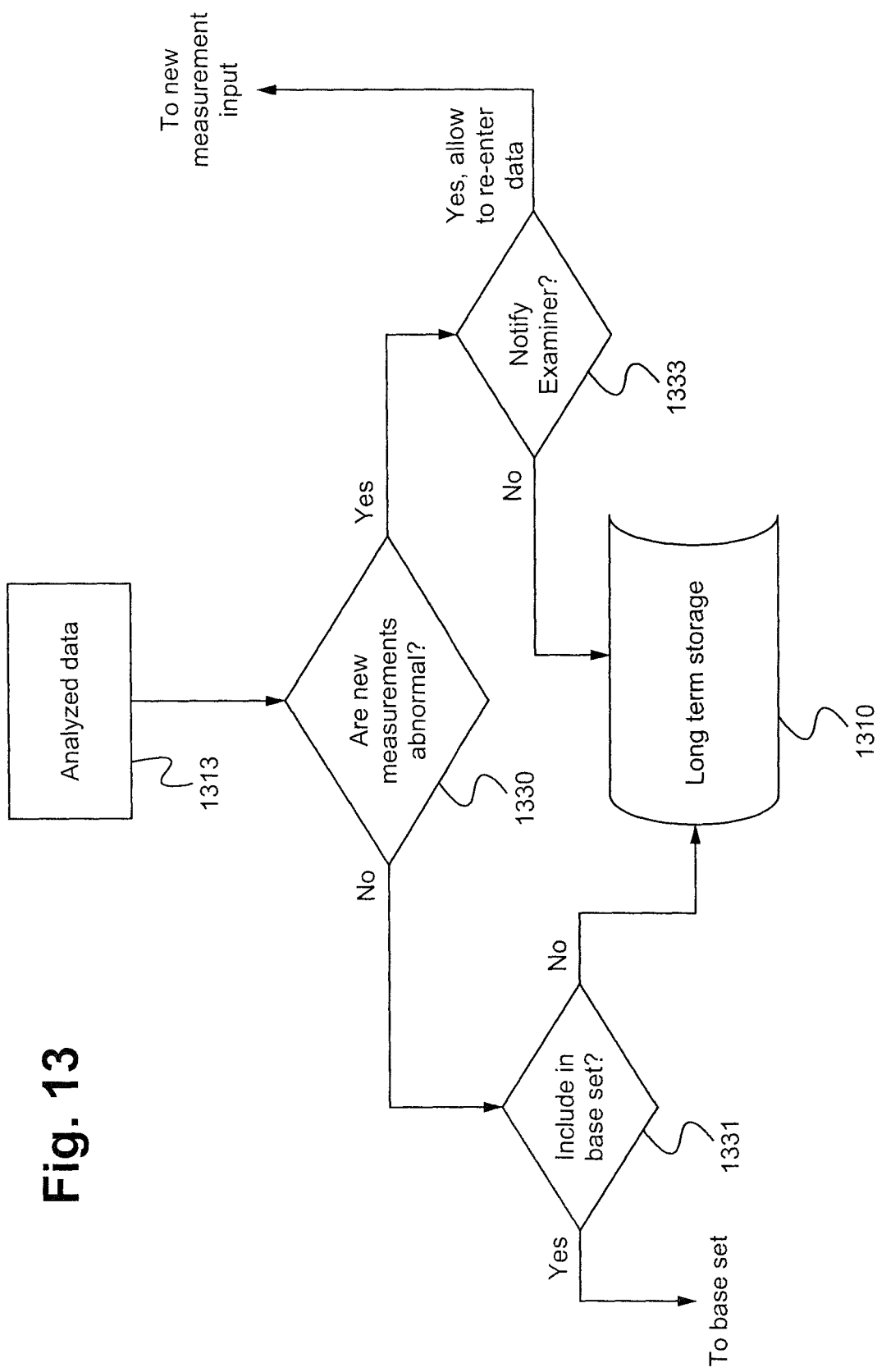

Injured Side

| Statistics | | Inequality | | Divisibiliy | |
|---|---|---|---|---|---|
| Min | 63 | %GT | 0.333333 | % /2 | 0.472441 |
| Max | 180 | %LT | 0.490196 | % /3 | 0.32381 |
| Range | 117 | %= | 0.176471 | % /5 | 0.165354 |
| Mean | 153.3 | | | | |
| Median | 157.5 | | | | |
| Mode | 172 | | | | |

Uninjured Side

| Statistics | | Inequality | | Divisibiliy | |
|---|---|---|---|---|---|
| Min | 117 | %GT | 0.276596 | % /2 | 0.504762 |
| Max | 185 | SLT | 0.531915 | % /3 | 0.32381 |
| Range | 68 | S= | 0.191489 | % /5 | 0.171429 |
| Mean | 163.7 | | | | |
| Median | 166.0 | | | | |
| Mode | 174 | | | | |

Fig. 19

METHODS OF OBTAINING HIGH ACCURACY IMPAIRMENT RATINGS AND TO ASSIST DATA INTEGRITY IN THE IMPAIRMENT RATING PROCESS

RELATED APPLICATIONS

This Patent application claims priority under 35 U.S.C. 119(e) of the U.S. provisional patent application, Application No. 62/103,479, filed on Jan. 14, 2015, and entitled "METHODS FOR OBTAINING HIGH ACCURACY IMPAIRMENT RATINGS," which is hereby incorporated in its entirety by reference.

FIELD OF THE INVENTION

The present invention is generally directed to automated applications of logic and statistics to medical processes to obtain improved accuracy in the measurement of a examinee's pathology from an injury. More specifically, the present invention is directed to a method and system of strict protocols, or Administrative Rule Sets (ARS) that direct examination for the purpose of obtaining an optimal data set, from which a rating of the impairment due to the pathology from an injury may be determined. A statistical analysis may additionally assist in obtaining an improved accuracy of impairment ratings.

BACKGROUND OF THE INVENTION

The current Workers Compensation practice enables the insertion of subjective opinion based on education and experience, and may even encourage it. The subjective nature of the 'diagnosis' is readily apparent to those involved in this process and can create a significant problem for society. For one to corroborate this need only observe the amount of litigation surrounding the Worker Compensation process. The result is needless expense, effort and delay in settling the claims.

Data collection and validation is the foundation of impairment rating. The accuracy and reproducibility of clinical data is necessary for the distribution of administrative benefits to applicants and for providing substantial justice, or fairness and speed required by the legal system. This application includes but is not limited to social security, workers' compensation, the VA Medical system and private insurance policies, etc. When the accuracy of clinical data recording is incorrect, it results in a great burden for the stakeholders in the system in the forms of fraud (intentional and unintentional), delay, and added expense and resources of second opinions and litigation. Therefore, the methods of collecting accurate and reproducible results in the impairment value determination arena is of the utmost importance, if the system is to serve the stakeholders as desired.

The ratable data set collected in the clinical setting must be accurate, reproducible regardless of clinician and verifiable to be considered valid. If the clinical data collected is inaccurate, the conclusions, which follow such as, benefit payment, access to future care, and impact on future earning ability are likewise incorrect. Moreover, fraud in the system is well recognized at the government level. For example, the California Department of Industrial Relations (DIR) has repeatedly issued public statements to the community acknowledging fraud is economically detrimental to society, with penalties including felony charges.

The American Medical Association's Guide to the Evaluation of Permanent Impairment, 5th Edition (the AMA Guide), notes that "[t]wo measurements made by the same Examiner using the Guides that involve an individual or an individual's function would be consistent if they fall within 10% of each other. Measurements should also be consistent between two trained observers or by one observer on two separate occasions, assuming the individual's condition is stable." [American Medical Association's Guide to the Evaluation of Permanent Impairment, 5th Edition, page 20]

Clinical evaluators responsible for the determination of the ratable impairment value face multiple challenges in the task of performing examinations. Error risks include the provider's experience and knowledge, as well as institutional bias (eg. creating false impairment values in return for economic return of referral business from either employers or patients). Institutional bias can be as obvious as fabrication of clinical data, or as subtle as using numeric patterns of similar cadence to simulate an independent data set. Additional error sources include right/left errors, and injured/non-injured body side and segment errors. Numeric reversal is yet another source of error (eg. the provider enters a "36" when s/he intended to enter a "63"). Taken in total, there are multiple challenges, both intentional and unintentional, in the current measurement system that represents a great economic and human resource cost.

The current practice to determine an impairment rating is for a clinician or doctor ("Examiner") to perform an evaluation on the worker resulting in a diagnosis of the amount of impairment. This rating is then documented and reported to various stakeholders. Studies have shown the variability of the impairment rating varies greatly among Examiners. This variance can be attributed to a variety of causes including; Examiner is not appropriately trained and experienced in impairment rating process, there is a bias on the part of the Examiner as to the nature of the injury, there is collusion between the Examiner and either the stakeholders or the worker. This variability, whatever the cause, is difficult to identify and correct as the stakeholder institutions have become reliant and even dependent on the process to have built in mechanisms to allow for these biases. The variability or error is then carried forward into the disability and compensation phases of the Workers Compensation claim.

Quite frequently, the error of the impairment rating results in other costly events such as: seeking a second opinion, the initial claim being rejected and needing to be re-done, litigation and added administrative oversight or the injured worker being undercompensated. In addition to the frequency and cost of these events is the time and effort spent on the attainment of the appropriate impairment rating and most importantly, the worker outcome.

SUMMARY OF THE INVENTION

The present invention addresses the root causes leading to inaccuracies in the impairment rating process. Providing a tool, which causes the Examiner to execute an accurate rating regardless of intention. Also, by providing established bounds of the rating process reduces or eliminates the ability of the Examiner to insert subjective bias into the examination process.

This invention provides examinees a clear and timely process for an optimal outcome, including approaches to mitigate the risk of intentional and unintentional error creation in the ratable data set. It also reduces the burden on the part of the Examiner to be in compliance with all established protocols. The stakeholders can benefit from a reproducible, accurate analysis enabling a predictable business model. A long term benefit of this derived objective invention is that it can always be adjusted in the future. If certain inaccuracies in the protocol or advances in medical science occur, the Administrative Rule Sets can be adjusted to account for improvements in the cost/benefit/outcome of a worker's injury. Injury as defined herein for the purposes of this document includes, but is not limited to a specific or cumulative injury, illness, or exposure.

As described below, algorithms are used to guide the measurement of the examinee's pathology resulting from an injury. Pathology as defined herein for the purposes of this document includes, but is not limited to a loss, loss of use or derangement of any body part, organ system, or organ function as these concepts are defined by the AMA Guides $5^{th}$ Ed. page 2 or similar definitions set forth in previous and subsequent editions. The application of this set of methods provides highly accurate and reproducible Impairment Ratings for Workers Compensation claims. This begins with use of proper measurement methods and data acquisition. This objective data set is used to perform established, unique and proprietary analysis that provides reproducible results. These methods enable a broad range of Examiners to perform such ratings and attain much more precision in the rating outcome with little or no variation across jurisdictions, clinics, and geographies.

The method also uses algorithms that can be accessed via a computer, laptop, tablet and smart phone app. The algorithms guide the Examiner to perform specific tests to ascertain the strength, range of motion, and pain present in the examinee. Pain is defined herein for the purposes of this document to include, but is not limited to pain and/or symptoms resultant from an injury. The Examiner is provided a step-by-step menu for the data generation and documentation process. Entering the data into the algorithm results in several unique simultaneous responses, depending on the number and nature of injuries, body part(s), value range of data entered. Body part(s) is defined herein for the purposes of this document to include but is not limited to body part(s) and/or organ systems. The data is evaluated for variance and possible anomalies in the data. The methods also store measurements for later calculation and use and/or select appropriate protocols (or Administrative Rule Sets—ARS), and perform calculations among which can be a partial or Whole Person Impairment rating.

The wide diversity of examination protocols resulting from the different body parts imposes a vast array of different interactive protocols. This is particularly cumbersome when multilateral injuries\pathologies are present simultaneously. Hence, the distinct different protocols (or "Administrative Rule Sets"—ARS) requires each body part to have it's own unique algorithms. Examples of body parts, representing different and unique algorithms, are: the spine, upper extremities, lower extremities, skin, pain, etc. Because of the wide range of protocols and resulting unique algorithms, the Examiner is faced with a myriad of decisions in the clinical setting, in addition to the performance of the exam itself. This complexity is a significant source of the errors and variability in the impairment rating process. Having these ARS's predetermined enables the clinical evaluation to target the appropriate tests and measurements, eliminating error and reducing variability in the impairment rating process.

Currently, the AMA guides call for the various portions of the body to be evaluated differently. Each body part has it's own unique characteristics to be examined. This results in each body part having a different Administrative Rule Set and resulting algorithm. In addition, another uniquely complex algorithm set that manages the interaction between the body part algorithms.

Nine different unique algorithms make up this invention, including: RateFast HUB, The Upper Extremity, The Lower Extremity, The Spine, Skin, Variable Thread Analytic Computation (VTAC), Maximal Medical Improvement (MMI), Calculator tool, Almaraz-\Guzman, Cannon v. the City of Sacramento, AMA Guides $5^{th}$ Ed. Section 1.20% Whole Person, Apportionment, Chapter 18 Pain AMA Guides $5^{th}$ Ed. Calculator and Comparison of Methods or similar conceptual definitions set forth in previous or subsequent AMA Guides Editions, and Comparison of Methods.

The data collection and validation is the foundation of an impairment rating. The accuracy and reproducibility of clinical data is necessary for the distribution of administrative benefits to applicants. This application includes but is not limited to social security, workers' compensation, the VA Medical system and private insurance policies, etc. When the accuracy of clinical data recording is incorrect, it results in a great burden to the stakeholders in the system in the forms of fraud (intentional and unintentional), delay, and added expense and resources of second opinions and litigation. Therefore, the methods of collecting accurate and reproducible results in the impairment value creation arena is the first step, if the system as it exists is to serve the stakeholders as intended.

The ratable data set collected in the clinical setting must be accurate, reproducible and verifiable to be considered valid. If the clinical data collected is inaccurate, the conclusions, which follow such as, benefit payment, access to future care, and impact on future earning ability are likewise incorrect. Moreover, fraud in the system is well recognized at the state government level. By preventing inaccuracies, fraud is likewise prevented.

The AMA Guides 5th Edition states on page 20, "Two measurements made by the same Examiner using the Guides that involve an individual or an individual's function would be consistent if they fall within 10% of each other. Measurements should also be consistent between two trained observes or by one observer on two separate occasions, assuming the individual's condition is stable."

Collection of biologic data presents a unique consideration, as the data sets are not distributed in a normal symmetric distribution. This means that when the data, for a shoulder forward flexion used as an example, distributes in an asymmetric fashion around the mean. The distribution of data, when studied plane by plane (of which there are six directions in the shoulder), begins to show reproducible patterns unique to each specific direction. In other words, both non-injured and injured body parts have "unique thumbprints" which reflect unique wave contours and curves only discoverable when plotted in this method. Furthermore, when the validated data is collected and analyzed, it can serve as a reference curve, or "gold standard" to be used to compare the statistical probability of a new data set being considered for valid comparison, based on the experience of the known valid data set. Once known, this curve has great value, as it can serve to determine fraud (both intentional and unintentional). The economic benefit of such a system is enormous in its impact and serves to solve the unnecessary waste and delay in the present system, as it offers a real time validity check for the stakeholders.

In one aspect, a method of obtaining a high accuracy injury impairment rating implemented within a computing system comprising a processor, a storage and a communications interface for communicatively coupling with a user device comprises choosing a jurisdictional province relative to the injury, choosing a working location, validating an injury demographic data set based upon the jurisdictional province and the working location, choosing an injury report, choosing an injured body part, based upon the injured body part, entering subjective present and historical data relating to the injured body part, describing a current treatment of the injured body part including work restrictions, describing a course of future care, analyzing the entered data based upon the jurisdictional province, and outputting an impairment rating for the described injury. In some embodiments, the jurisdictional province selects an administrative rule set that is applied to the entered data. The jurisdictional province can be different than the working location. In some embodiments, the subjective and historical data comprises both general and specific examinee complaints regarding the activities of daily living. In some embodiments, one or more body part is analyzed to obtain an organ subset or a whole person impairment rating.

In another aspect, a method of measuring an examinee's pathology from an injury comprises evaluating the examinee to determine an initial injury to the examinee, based upon the evaluation, performing one or more tests on the examinee to obtain injury data, applying an administrative rule set to the injury data, and outputting an impairment rating based upon the injury data. In some embodiments, the impairment rating is performed on a single body part. The impairment rating of one or more body parts can be combined to obtain a whole person impairment rating. The impairment rating can be determined for one or more organ sets. There is an administrative rule set for each body part.

In a further aspect, a method of calculating an impairment rating is based upon an observed clinical data set. The method comprises dividing the clinical data set into one or more organ system subsets, receiving each of the organ system subsets at a impairment rating calculator, applying logic to the organ system subsets to define an impairment rating for each organ system subset, and combine each organ system subset impairment rating to calculate a final whole impairment rating. In some embodiments, the one or more organ system subsets comprise a plurality of body parts. Each body part can comprise a unique calculator. The logic is defined by one or more administrative rule sets unique to the organ system. In some embodiments, the highest possible impairment rating is assigned to each body part including alternative valid rating methods and outcomes. The impairment rating can comprise an organ system impairment rating. In some embodiments, the impairment rating can comprise a whole person impairment rating.

In still a further aspect, a method of determining abnormal behavior within the impairment rating process comprises determining a unique base set of data, defining abnormal behavior according to the unique base set, analyzing incoming data based upon the abnormal behavior, and classifying the incoming data as valid or statistically abnormal. In some embodiments, the data is analyzed according to a cutoff value or threshold value of tolerance. A unique base set of data can be created for each direction of motion of a body part.

In another aspect, a method of constructing an apportionment of a permanent disability determination resulting from a permanent impairment comprises identifying one or more functional activity limitations based on the permanent impairment, identifying one or more non-industrial contributors and/or factors of the one or more functional activity limitations based on the permanent impairment, creating one or more independent models using an adjusted pain value method, subtracting an apportionment percentage of each of the one or more functional activity limitations from a sentinel injury being considered by a stakeholder, assigning a weighted apportionment of the one or more functional activity limitations, and delivering one or more final percentage contributions of the one or more functional activity limitations.

BRIEF DESCRIPTION OF THE FIGURES

FIGS. 3A-3C illustrate lower extremity impairment algorithms in accordance with some embodiments.

FIG. 9 illustrates a comparison of methods (ROM & DRE) in accordance with some embodiments.

FIG. 13 illustrates a method of processing analyzed data when determining abnormal behavior within the impairment rating process in accordance with some embodiments.

FIG. 19 illustrates a distinction between an injured shoulder and an uninjured shoulder in accordance with some embodiments.

DETAILED DESCRIPTION OF THE EMBODIMENTS

Glossary

Figure 1A:
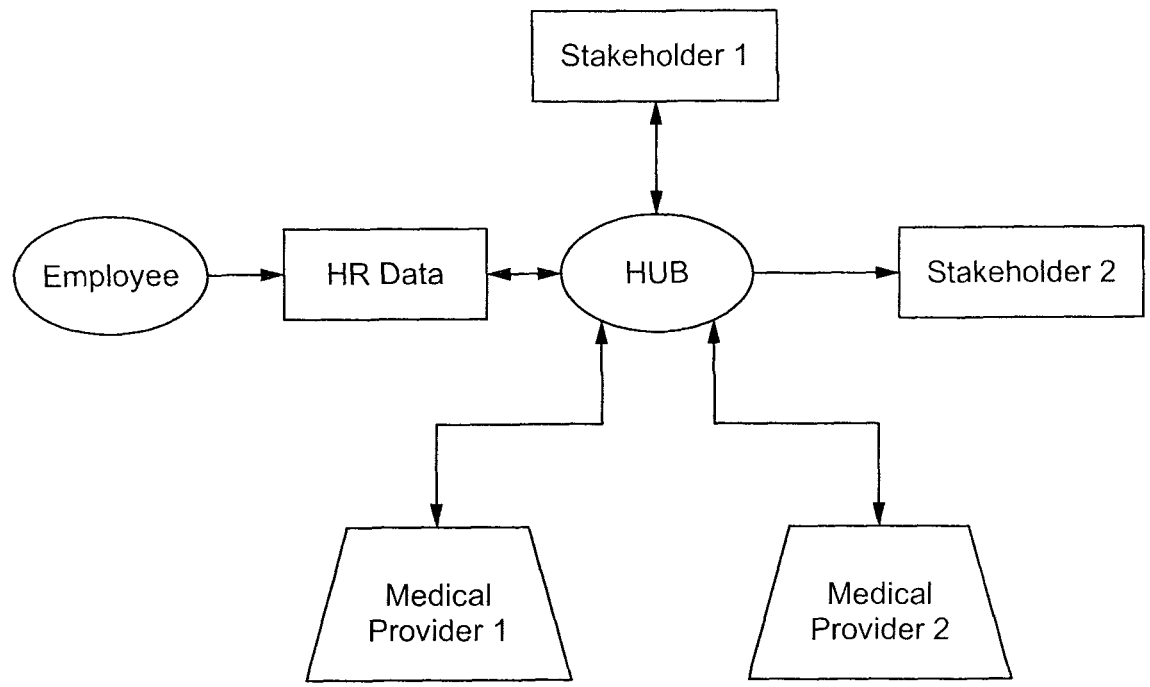
FIG. 1A illustrates a hub workflow diagram for a method of obtaining a high accuracy impairment rating in accordance with some embodiments.

The following terms are defined here as they relate to the content of this document.

Administrative Rule Set (ARS):

The logic structure provided for analyzing an injured body region; that includes but is not limited to The American Medical Association's (AMA) Guide to the Evaluation of Permanent Impairment or federal or state mandates, US Social Security, the VA Medical Center system, or any other national or international set of administrative rule sets. This unique incorporation of a diversity of ARSs, particularly when multiple body parts are simultaneously involved, provides a basis for a very complex and robust interaction in the rating process. For this reason, the Rate Fast algorithms incorporate a diversity of ARSs in them. The diversity of ARSs, in a clinical 'pencil and paper, process is the primary source of impairment rating error. For a clinician to be aware of all the ARSs and their interactions, in a time constrained clinical setting makes it virtually impossible to achieve accurate, reproducible ratings without a governing algorithm.

American with Disabilities Act (ADA):

"A civil rights law, signed in 1990, that protects individuals with disabilities against discrimination in such diverse areas as employment, government service entitlement, and access to public accommodations." Page 599 AMA Guides 5th ed.

The AMA Guides® to the Evaluation of Permanent Impairment:

The publication of the American Medical Association to be referred to in this document, as "The Guides" is a widespread recognized authoritative document. There are numerous existing versions of this document; it is currently in the 6th Edition as of the drafting of this application. The AMA Guides® are used in multiple states for workers' compensation administrative purposes and also used by the US Federal Government for adjudicating federal injured worker cases, as well as, Maritime and the Federal Railroad systems. The Guides are also used internationally for injury evaluation and impairment description.

Algorithm:

For the purposes of this invention, an algorithm is defined but not limited to the automated application of an ARS applied to the claim data set for the purposes and utility of obtaining the most accurate and efficient methods for obtaining an impairment rating.

Apportionment:

AMA Guides 5th ed. Defines apportionment as "A factor(s) (e.g. physical, chemical, biological, or medical condition) that adversely alters the course or progression of the medical impairment. Worsening of a preexisting medical condition or impairment." Page 599. For purposes of the teaching this document, historical data which can compared to the current clinical data set relied upon for, but not limited to, includes subjective complaints (e.g. pain presence or absence, analogue pain report (e.g. 0-10/10 pain intensity score, and frequency), activities of daily living, and measurable (e.g. objective data such as functional measurement and/or diagnostic imaging or any observable measurement or means of documenting a prior condition which precedes the date of injury (DOI) being considered for permanent impairment rating. Apportionment can affect the final claim benefit if a pre-existing condition (e.g. permanent impairment) is identified which has resulted in a permanent disability prior to the DOI for the present claim being evaluated.

Available Treatment:

Maximum medical improvement (MMI) is a concept and point in treatment process that is a combination of availability of administrative resources and the medical judgment of the treating provider. These authors consider the concept of a "probable MMI" point in treatment process as a speculative activity, as a definition of "available" is essentially unbounded. Furthermore, extrapolating an individual's estimated measurable impairment rating, whole person impairment (% WPI), outcome on population statistical studies, models or algorithms is not expressly discussed or endorsed by any version of the AMA Guides through the 6th ed. The process of extrapolation is not specific to the individual being considered for impairment rating.

The statement "available to them" for purposes of this teaching, implies all "available" treatments modalities, surgical interventions or pharmaceutical, or technical interventions mechanical, therapeutic or chemical (medicine), but not limited to these examples.

Furthermore, "available" treatment may be dependent upon legislative creation of mandated guidelines with examples such as, but not limited to, the American College of Occupational and Environmental Medicine© (ACOEM) 2nd Ed, the California Medical Treatment Utilization Schedule© (MTUS), the Official Disability Guidelines© (ODG) or otherwise medically determined appropriate by peer reviewed process (e.g.: Utilization Review Process).

The AMA Guides® 6th ed. considers impairment rating on the basis of functional diagnosis which is a subjective determination process, not based on prior AMA Guides® (Edition 1-5) teaches an impairment rating based on data driven and insensitive to subjective diagnoses by the evaluator. "In this edition there is a paradigm shift, which adopts a contemporary model of disablement; it is simplified, functionally based and internally consistent to the fullest extent possible." Page 2, Section 1.2a AMA Guides® 6th ed. "Rating percentages derived according to the Guides are functionally based, to the fullest practical extent possible." Page 2, Section 1.2b item 4 AMA Guides® 6th ed.

Although the AMA Guides advocates a paradigm shift, the creation of permanent impairment percent value (% WPI) is still dependent on the collection of observable and measurable loss which is the spirit and method of the preceeding editions. In fact, some accuracy in the creation of impairment measurements, such as upper extremity, results in more ambiguity in the AMA Guides 6th ed. because of consolidations of measurement ranges, and not the assignment of a more specific value to an actually obtained measurement (e.g. AMA Guides 5th ed.).

A consolidation of the impairment rating process further provides a basis of ambiguity to the rating process.

Base Set:

A set of range of motion (ROM) measurements taken for the specific purpose of serving as a template for future data. It is upon the base set of data that all statistical knowledge of the data is assumed.

Body System Impairment Value:

An impairment value(s) assigned to but not limited to a body part or organ system.

Boolean Logic:

An application of logic dependent on gating of data input including, but not limited to calculations results and workflow decision trees which may include collective logic function. Examples are 'Basic Operations': "AND", "OR", "NOT", and 'Derived Operations'; "Material Implication", "Equivalence" and "Exclusivity".

Calculator Engine:

A sub routine program that performs an impairment rating function.

Causation:

The process of the determination that includes, but is not limited to the claimed injury being assigned to a particular event or set of circumstances for which medical treatment access may or may not be provided by a stakeholder.

Characteristic Profile:

A collection of traits characterizing the base set of measurements for a particular direction of motion. These traits include, but are not limited to: measurement distribution, disparity between measurements, and associated probability density functions (PDFs). Also numerical properties such as inequality between multiple measurements within a single case, divisibility of measurements, range, mean, median, mode, measures of skewness, among other representative properties. When the data is plotted the resulting shape or "Profile" is unique to that data set and model.

Claim Set Impairment Value (CSIV):

Any and all ratable content and data contained within the clinical data set (CDS) to which an impairment value may be assigned or affects the creation and the assignment of an impairment value. This definition includes any contribution to the hierarchy of impairment value creation from the ratable data sets (RDS) to the % WPI.

Clinical Data Set (CDS):

The subset of the examinee claim includes but is not limited to a data set including measurable and reproducible signs, symptoms, physical and functional measurements and diagnostic findings relevant to an injured body system part or parts.

Continuous:

Continuous to refers to a probability density function that is defined for all values between two points e.g. Exponential density is defined for any value greater than or equal to zero. This distinguishes continuous PDF's from discrete, which are only defined for specific values.

Data Set:

A collection of inputs, including but not limited to clinical measurements, test results, or ranges of results for the purposes of creating an impairment value or other metrically driven result.

Date of Injury (DOI):

The date which a defined injury occurs (e.g. slip and fall) to the examinee, or the administrative date (e.g. onset of carpal tunnel) assigned for the ARS.

Diagnostic Test:

A device based on a fundamental unit of objective measurement. This includes but is not limited to image analysis, weight, length, temperature, rates of biological events, pressures, force, light, intensity, signals, etc.

Digitized Data Set:

A collection of inputs, including but not limited to clinical measurements, test results, or ranges of results for the purposes of creating an impairment value or other metrically driven result that are inputted into an electronic environment or setting.

Disability:

"The term disability has historically referred to a broad category of individuals with diverse limitations in the ability to meet social or occupational demands." Page 8, Section 1.2b AMA Guides 5th ed. "The Guides continues to define disability as an alteration of an individual's capacity to meet personal, social, or occupational demands or statutory or regulatory requirements because of an impairment." Page 8, Section 1.2 AMA Guides 5th ed.

"Activity limitations and/or participation restrictions in an individual with a health condition, disorder, or disease." Page 5, Section 1.3d AMA Guide 6th ed.

Discrete:

Discrete refers to a probability distribution that is defined only for a specific set of values e.g. the Poisson PDF is only defined for integer values greater than or equal to zero. This distinguishes discrete PDF's from continuous, which are defined for all values within a specified range.

Employee Assistance Program (EAP):

A program function of the employer's Human Resource department that assists an individual to address medical conditions and support to optimize the individual's safe return to the workplace and remain compliant with the ADA requirements and other employment administrative laws and requirements.

Examinee:

An Examinee is an individual who is the subject of an impairment rating process.

Examinee Demographic Data Set (EDDS):

An examinee data set is a collection of individual identities associated with the examinee and may include but not be limited to an individual's name, biological gender, assumed social gender, date of birth, social security number, physical address, email address, phone number(s), ethnicity, languages and next of kin.

Fit for Duty Exam:

An examination requested by a stakeholder based on an observed behavior while the individual in arriving to, performing, or leaving the workplace. (e.g. smells of alcohol).

"Four Corners":

This is a term emanating from California Workers' Compensation Appeals Board ruling regarding the cases of Mario Almaraz and Joyce Guzman. This landmark ruling shall be referred to as the Almaraz-Guzman case in this document. The four corners is described in this ruling as the examining physician's basis for evidence that may be presented to demonstrate that the standards for rebutting the AMA Guides impairment rating have been met. Within this discussion are the critical factors in the physicians' opinion to rebut the 'Guides'. They are; physicians judgment, experience, training, and skill. These four attributes are known as the four corners. There are substantial discussion and explanation of these attributes in this ruling; the reviewer is encouraged to obtain this document if further detail is desired.

Fraud:

Fraud is defined in the broadest sense as "deception made for personal gain". This is described in the AMA "Guides" on Page 6, Guides to the Evaluation of Disease and Injury Causation, American Medical Association 2008. This topic is so significant that the California Department of Industrial Relations Division of Workers Compensation in October of 2012 sent out a broad communication regarding impairment rating fraud.

For the medical provider the four areas highlighted, but not limited to, were; billing fraud, employing individuals to solicit new patients, unnecessary treatment or self-interested referrals, and failing to report a work injury.

In this communication is the following excerpt: "Workers' compensation fraud is a drain on California's economy. Workers compensation fraud harms employers by contributing to the high cost of worker compensation insurance and self-insurance and it harms employees by undermining the perceived legitimacy of the workers' compensation claims. Workers' compensation fraud is not limited to claimant fraud. The workers' compensation program can also be victimized by fraud committed by medical providers, employers, claims adjusters and attorneys."

Collusion between at least two of the parties involved in impairment rating can represent fraud. The goal of the RateFast algorithms is to apply the highest ethical and legal standards to the impairment rating process and to reduce or eliminate the chance of fraud occurring.

Functional Capacity:

"From the disability perspective, the idea of a task is the central concept of functional capacity. A task is a complex physical or mental action with a defined result (e.g. climbing stairs, writing, reading, calculating, multiple simultaneous attention). After reduction by impairment, what is left is a residual functional capacity, which is usually expressed as a limit: . . . ." Page 119, A Physician's Guide to Return to Work, American Medical Association 2005.

Functional Measurement:

The process documenting with numeric assignment to include but not limited to any dynamic motion of function (e.g. range of motion described in degrees of motion) considered valid if reproducible within a tolerance described by the ARS.

Fuzzy Logic:

The application of logic that allows subsets of answers that provide a more accurate weighted value in the use of Boolean logic. For example, the presence of pain can be further defined by using terms such as "Occasional (25%)", "Intermittent (50%)", "Frequent (75%)" or "Constant (100%)".

Generalization:

If Function A is a generalization of Function B, then Function A has all the capabilities of B, plus additional freedom. Function B would be a limiting case of Function A.

Group Logic Data Set (GLDS):

A grouping of Administrative Rule Sets that variable thread analytic computation (VTAC) can be applied to arrive at the optimum impairment rating.

Health Information Privacy Protection Act (HIPPA):

"The HIPAA Privacy Rule, which protects the privacy of individually identifiable health information; the HIPAA Security Rule, which sets national standards for the security of electronic protected health information" US Department of Health and Human Service (http://www.hhs.gov/ocr/privacy/).

Hierarchy of Impairment:

Hierarchy of impairment includes, but is not limited to, the process of converting an impairment value(s) from the most primary level of the ratable data set to a single number representative of the claim data set. For example, using the AMA Guides® 5th Edition administrative rule set, a ratable data set for a finger would begin with impairment assignment as "digit impairment." This numerical value, in conjunction with other relevant impairment values, is then progressively converted to "hand impairment," "upper extremity impairment," and finally "whole person impairment."

Histogram:

A graphical representation of numerical data's distribution. To construct a histogram, one must first partition the range of data into a series of smaller subintervals. Then, one counts how many data points fall within each subinterval. Finally, a rectangle is drawn to a height reflecting this count. Within the invention, histograms of ROM data for a direction of motion are created as described and then scaled to have an area equal to one.

Human Resource (HR):

A person engaged to perform a function for an organization. This person can have a fiduciary contract with the organization that is directing the person's activities. In larger organizations, the educational background or formalized training must be in accordance with the job description as outlined by government regulations such as "Sarbaines-Oxley". These definitions of Human Resource and Job Description cause development of formalized, accepted job descriptions by an overseeing government. An example is the State of California RU-91.

Hypermobility:

"Hypermobility" is a condition where the combination of an excessive Range of Motion beyond that described in the AMA Guides and the Activities of Daily Living are not impacted or affected. Hypermobility is a condition that includes but is not limited to hyperextension, hyperflexion, subluxation, hyperlaxity, or dislocation. This condition, though not normal, is common enough and significant enough to merit examination for its presence in the writing of the AMA Guides 5th ed, page 455, where it is discussed: "If an involved joint has "normal" motion according to the values specified in the Guides and the contralateral uninvolved joint has greater than average motion, there is a relative loss of motion a zone beyond the normal values does not as a rule represent a loss of function or impairment." However, it further states, "In rare cases, based on the Examiner's clinical judgment, an impairment percent not to exceed 2% of the maximal regional impairment value of a unit of motion can be given.

Impairment:

"A loss, loss of use, or a derangement of any body part, organ system, or organ function." Page 2, Section 1.2 AMA Guides® 5th ed.

"A significant deviation, loss, or loss of use of any body structure or body function in an individual with a health condition, disorder, or disease." Page 5, Section 1.3d AMA Guides® 6th ed.

Both definitions of Maximal Medical Improvement from the 5th and 6th editions of the AMA Guides® are used herein. The definition in the 5th edition is preferred as it logically is more cogent and applicable to the objective "spirit" of the impairment rating process.

Injury demographic data set (IDDS):

An injury demographic data set may include but is not limited to members of the examinee's treatment execution team, employer, occupation, date of injury, last date employed, date of MMI, insurance carrier, insurance carrier contact information, name and contact information of utilization review service, insurance adjuster contact information, and nurse case manager contact information, etc.

All data in an injury claim includes but is not limited to demographics, occupation/industry, payer information and information obtained in the course of evaluating prior conditions, executed treatment, offered treatment, recommendations, available treatments, pre-existing same and other body system conditions, prior surgical same and/or other body system, social history, a vocational activities and hobbies, other employment, military and/or other exposures, the signs, symptoms, effects of treatments and physical measurements, concluded diagnoses, treatments offered (past and future), or otherwise any and all findings obtained during the examination process (e.g. including but not limited to physical exam findings, functional measurements, and diagnostic testing results.)

Institutional Bias:

Institutional bias is defined as an institution that knowingly enables error, primarily by omission of guidance or lack of rigor, by the submitting professionals and the reviewing stakeholders. Bias in this definition refers to the institution's wide acceptance of a broader range of ratings or values than should be present. Hence, the likely value can fall within the range of typical evaluations; it is the tolerance of variance that is the actual bias, obfuscating the true rating by the professional. This impairment variance is then propagated forward, and embellished, to the overlaying of the "Activities of Daily Living" (ADL) and toward impact (Disability) on the earning capacity or livelihood, and equitable distribution of benefits.

International Classification of Diseases (ICD):

"The ICD is designed as a health care classification system, providing a system of diagnostic codes for classifying diseases, including nuanced classifications of a wide variety of signs, symptoms, abnormal findings, complaints, social circumstances, and external causes of injury or disease. This system is designed to map health conditions to corresponding generic categories together with specific variations, assigning for these a designated code, up to six characters long." http://en.wikipedia.org/wiki/International_Statistical_Classification_of_Diseases_and_Related Health_ Problems Limitation:

"Limitation is what a person cannot do as a result of illness or injury. For example, a person is limited from (physically incapable of) driving an automobile while having a generalized seizure, as he or she is unconscious during the seizure. By virtue of this definition, limitation is usually measurable or objectifiable. In practice, an estimate of functional capacity by limitation is usually supported because it is judged clinically proportionate to a demonstrated impairment." Page 120, A Physician's Guide to Return to Work, American Medical Association 2005.

Limiting Case:

If Function B is a limiting case of Function A, then Function A has all the capabilities of B, plus additional freedom. Function A would be a generalization of Function B.

Maximal Medical Improvement:

"'Maximal Medical Improvement' (MMI), meaning it is well stabilized and unlikely to change substantially in the next year with or without medical treatment. The term impairment in the Guides refers to permanent impairment, which is the focus of the Guides." Page 2, Section 1.2 AMA Guides® 5$^{th}$ ed.

"Maximal Medical Improvement" refers to a status where patients are as good as they are going to be from the medical and surgical treatment available to them. It can also be conceptualized as a date from which further recovery or deterioration is not anticipated, although over time (beyond 12 months) there may be some expected change." Page 26, Section 2.5.e *AMA Guides® 6th ed.*

Mean:

Synonymous with 'average'. For a discrete distribution, summing the data points and dividing by the number of data points may find the mean. For a continuous distribution, the following formula is used instead to find the mean of distribution. A base set's mean is one numerical property in its characteristic profile.

Median:

The value at the center of a data set. A base set's median is one numerical property in its characteristic profile.

Medical Diagnosis:

A term referenced but not heretofore defined in the AMA Guides. For the purposes of this document medical diagnosis will be adopted as described by Wikipedia (http://en.wikipedia.org/wiki/Medical_diagnosis) as: "Medical diagnosis (often abbreviated dx or Dx) is diagnosis in the field of medicine, that called simply diagnosis when the medical context is implicit. Both the process of determining which disease or condition is present and the conclusion that is reached by this process are called "diagnosis" (for example, the process of diagnosis can yield a diagnosis of strep throat). The foundation of diagnosis is always the information from the history and the physical examination, but often one or more diagnostic procedures, such as diagnostic tests, are also done during the process. Diagnosis is often challenging, because many signs and symptoms are nonspecific. For example, redness of the skin (erythema), by itself, is a sign of many disorders and thus doesn't tell the physician what is wrong."

Medical Provider Network:

A medical provider network (MPN) is an entity or group of health care providers set up by an insurer or self-insured employer and approved by DWC's administrative director to treat workers injured on the job. Under state regulations, each MPN must include a mix of doctors specializing in work-related injuries and doctors with expertise in general areas of medicine. MPNs are required to meet access to care standards for common occupational injuries and work-related illnesses. The regulations also require MPNs to follow all medical treatment guidelines established by the DWC and allow employees a choice of provider(s) in the network after their first visit.

Additionally, MPNs must offer an opportunity for second and third opinions if the injured worker disagrees with the diagnosis or treatment offered by the treating physician. "State of California Department of Industrial Relations (http://www.dir.ca.gov/dwc/MPN/DWC_MPN_Main.html)

Organ systems Organ systems are described in the AMA "Guides" 5th edition in chapters 3, 4, 5, 6, 7, 9, 10 12, and 13. The systems are comprised of Heart and Aorta, Systemic and Pulmonary Arteries, Respiratory, Digestive, Urinary and Reproductive, Hematopoietic, Endocrine, Visual, Central and Peripheral Nerves.

Mode:

A mode in a data set is any value which has maximal probability. The mode of a continuous variable with probability density would be any such that is a local maximum. A base set's mode is one numerical property in its characteristic profile.

Percent Whole Person Impairment (% WPI):

The single and final impairment value assigned in a numeric range value of 0-100 when all data within the "clinical data set" (CDS) has been determined and advanced through the hierarchy of impairment.

Permanent Disability Rating (PDR):

An administrative calculation based on a permanent impairment value or documentation of a permanent impairment being present.

Physician Skill:

Physicians' skill is the utility of a physician to illicit information from the individual being examined. This includes the ability to obtain a history and performing a relevant exam. In the exam the physician's skill can employ the use of his/her ability to see, smell, touch, or hear.

Probability Density Function (PDF):

The language surrounding 'density' and 'distribution' is often vague and/or contradictory within the literature. Here, as in other texts, we use the following definitions. Continuous data is represented by a probability density function.

Example: data is Normal if it is governed by the Normal PDF. Then, the probability that data falls within a specified range of possible values would be found by integrating the Normal PDF over that range. This data would be referred to as being 'Normally Distributed'.

Probability Distribution:

Discrete data is governed by probability distributions. A probability distribution is a function that assigns each acceptable input with its appropriate probability. This is different than a PDF, as a density function itself does not assign probabilities; the integral of it does.

Ratable data set (RDS):

The subset of the examinee clinical data set includes but not limited to which numeric valuation is assigned and which contributes to the calculation of an impairment value; e.g. loss of motion in a joint or the distribution of pain/ symptoms in a limb. Example, a lumbar spine nerve root manifesting symptoms in an anatomic distribution (e.g. Pain above the knee is internally consistent with the second lumbar nerve root dysfunction in the back.

Reasonable Accommodation(s) (RA):

The employer process to incorporate the findings of a permanent impairment, that an impaired individual and the desire for enabling ongoing employment to provide suitable worksite modifications. This can include a review of current infrastructure or an alteration of the physical environment in compliance with the ADA.

Return to Work Exam:

The "Return to work exam' is a medical examination of an individual who is absent from the workplace for a non-industrial medical condition for determination of the ability to resume usual and customary work activities.

RU-91 of the State of California:

A formal standardized job description that expresses essential job activities to be defined as correct by employer and employee that serves a historic document agreed upon for future injury used for return to work consideration either for an industrial or non-industrial conditions.

Shell Program: Includes but is not Limited to the Following Functions:

Controls the graphic user interface guiding the user through the data collection and entry process, and automatically alerts the user when a "real time" collection of data results in a non-valid calculation required by the ARS. Collects both user-related information and claim data sets entered by the user. Places a "thin client" program on the user's internet-connected computing device to facilitate user input. Encrypts and passes user and claims data sets to the database controller for storage.

Sign:

Signs are the observable findings of the Examiner. This includes but is not limited to the physical appearance, measurements both static (e.g. limb length cm or degrees of angulation) and functional (e.g. degrees of motion), and/or the necessity of a durable medical device to restore function. The collection of signs by the Examiner also includes his/her ability to see, smell, touch, or hear.

Stakeholders:

A stakeholder is defined as any party, entity, company or individual with an interest such as but not limited to the examinee, medical providers, employers, insurers and state and federal entities etc.

Static Measurement:

The process documenting with numeric assignment to include but not limited to any static measurement (e.g. limb length described in centimeters (cm), limb circumference (cm), or an x-ray of a joint which describes an abnormal angulation or cartilage interval in millimeters (mm) considered valid if reproducible within a tolerance any standardized bony or anatomical landmark referenced and described by the ARS.

Subset Impairment Values (SSIV):

A subset of the CDS specific to an identified body system and the subsequent assignment of impairment value.

A numerical value is assigned as a quantifiable value to a finding, which includes but is not limited to, an assignment of a lowest common denominator or lowest mean value of a single variable within the ratable data set and later to be used in the hierarchy of impairment rating. Example, an index distal phalanx joint subset impairment value describes the limitation in the flexion plane of motion to 10 degrees, is assigned a digit impairment value of 4% (% DI).

Symptom:

The individual's claimed subjective report of an injury or illness.

Substantial Justice

Substantial Justice is a concept and obligation to provide fairness and speed within the legal system. For example, the California Worker's Compensation Appeals Board (WCAB) defines the concept and obligation of Substantial Justice in the case of *Greene* v. *Central Parking* Systems as constitutionally mandated to accomplish substantial justice in all cases, expeditiously, inexpensively, and without incumbrance. *Greene* v. *Central Parking,* 2015 Cal. Wrk. Comp. P.D. LEXIS 283.

User:

Includes but is not limited to any individual or shareholder that can contribute, input or consume results on the RateFast platform.

User Data Set (UDS):

All information pertaining to the user; including but not limited to name, professional credentials, occupation, specialty training, and geographic location. Examples of a user can include health care providers, administrators, government entities, private industry, insurance carriers and even an individual who is self examining a claim.

Variable Thread Analytic Computation (VTAC):

The method used to solve and/or analyze simultaneous interactive functions to determine multiple comparisons of theoretical outcome and possibilities, used to assign optimal compliance with the ARS.

Work Capacity:

"Capacity refers to concepts such as strength, flexibility, and endurance." Page 9, A Physician's Guide to Return to Work, American Medical Association 2005.

Work Limitation:

"What the patient lacks the current ability to do." Page 11, A Physician's Guide to Return to Work, American Medical Association 2005.

Work Restriction:

"A work restriction is something a patient can do, but should not do" Page 7-8, A Physician's Guide to Return to Work, American Medical Association 2005.

Work Tolerance:

"Work tolerance is a psychophysiological concept. It is the ability to tolerate sustained work or activity at a given level." Page 10, A Physician's Guide to Return to Work, American Medical Association 2005.

Worker or Employee or Examinee and Employer or Stake Holder:

In this document, the "Worker" or "Patient" or "Examinee" is meant in the broadest terms. A "Worker" is a person who has been directed to execute a function or task, or set of functions or tasks, on the part of an "Employer". Also, in this document, "Employer" is meant to be in the broadest terms possible. "Employer" is an entity that has engaged the "Worker" specifically to perform in a function or set of functions. The Employer can be a person, a company, a government, etc. When the "Worker" is in the act of execution of the functions or tasks sustains an injury(ies), this combination of circumstance is usually what comprises a Workers Compensation Claim. Governing entities typically require some form of evaluation of the injury (ies) and initiate a preliminary report of the initial sustained impairment rating. After some significant time, the employee is evaluated for the permanent impairment when it is thought that "Maximal Medical Improvement" (MMI) has been obtained.

Section 1: Introduction:

The current invention is for a system and method called RateFast that provides an automated platform that guides medical practitioners through the systematic collection of impairment related clinical data. The program eliminates the requirement that medical practitioners have and apply subspecialized knowledge as to what clinical data needs to be gathered for evaluation of any impairment. It also provides the practitioner with formatted reports required by administrative entities for documentation and monetization of a claimed disability. Additionally, it provides a compliant method of storing and retrieving previously entered data at a future time.

RateFast allows a quantifiable impairment rating (Percent Whole Person Impairment; e.g. % WPI) by direct examination of the examinee's acquired clinical data set while simultaneously applying a matrix of Administrative Data Sets/algorithms unique to each individual examinee injury (ies) and impairment(s).

RateFast is a non-obvious process to the user because it provides complex computations specific to the administrative rule set the user is working in and specialized formatting of clinical information entered by the user.

No tool currently exists that allows medical care providers to accurately and reproducibly calculate impairment ratings across the array of administrative rule sets. Calculation of an accurate impairment rating requires numerous combinations of clinical signs and symptoms be considered in a logical hierarchy following strict, layered rules set forth by the administrative rule set relevant to the examinee and impairment type. Consequently, a variety of administrative rule sets exist, each defining its own unique hierarchy. The vast diversity of administrative rule sets give rise to error in the diagnosis and impairment rating process. As such, a unique algorithm must exist for each type of impairment. Adherence to the logic is necessary for impairment ratings to be considered acceptable to administrative and/or employer insurers or other entities. Failure to follow and enact individualized algorithms in the administrative rules sets give rise to propagation of error and interpretation of identifying the absence or presence of disability and correctly weighing the economic or resultant examinee benefit. Disability conclusions drawn on incorrect impairment values are therefore also faulty.

The conditions affecting single body part evaluation are different under different administrative rule sets. This complexity is compounded when two or more body systems are being evaluated. Each body part may or may not affect the impairment values of another and this affectation can be different under various administrative rule sets.

RateFast provides medical care providers with a method of consistently and correctly applying the correct administrative rule sets to any given set of clinical data, regardless of the rule set and number of body parts being evaluated. The method does not require the user to have specialized knowledge of the complex logic required to either calculate impairment ratings or generate medical or legal reports based on those ratings. As such, RateFast improves the accuracy of the impairment rating process, and enables a much broader array of medical providers to apply the method. RateFast accesses a higher command of administrative rules sets by using algorithms resulting in the development of a larger user base with reduced error/waste. Further, the method avoids errors in the impairment rating presently carried forward through the disability, care and compensation phases of the process in addition to complying with the judicial mandate of substantial justice, as defined earlier in this document.

Section 2: Algorithm Attributes

Current methods do not allow algorithmic impairment rating calculations for all body parts. RateFast expands the scope by applying an automatic impairment rating for all body parts and body systems. RateFast decreases error and increases calculation accuracy and provides efficiency to the process, making this impairment rating skill accessible to a larger user base.

Additionally, RateFast increases data valuation by concurrently and automatically processing raw clinical entered data for validity. For example, most administrative rules sets require that evaluation of certain joint injuries include three separate measurements be performed and tested for <10% variance. Previous models allow invalid data sets to be processed, which results in invalid or even nonsensical conclusions. RateFast performs data validations to ensure that accurate impairment ratings are generated. This ensures that medical practitioners document impairments, and helps ensure that those impairments are properly monetized to a disability when applicable.

As two or more body parts are considered for impairment rating, the opportunity for error is more probable. The complex administrative rule sets which affect the adjoining rules for impairment value assignment can or can not influence the outcome given specific conditions of the data set. Calculation of an impairment rating for multiple body parts is more complex than a single body part injury because the interaction of hierarchical data sets and algorithms becomes even more complex. Adherence to existing administrative rule sets requires that the hierarchy of impairment rating correlates and is adjusted for each involved body part.

Additionally, the invention not only assists medical practitioners in documenting the claimed injury and calculating an impairment rating but also formats the appropriate parts of the clinical data set and associated impairment values into a written report acceptable to stakeholders such as but not limited to the examinee, medical providers, employers, insurers and state and federal entities. Further, upon clinical follow up and analysis and following the non-permanent impairment and the effects of available treatment, the ultimate benefit on the final impairment in the context of geographic circumstance, and administrative rules sets is achieved.

Moreover, an unmet challenge in injury claim and impairment claim evaluation is the variability between administrative rule sets. For example, a clinical data set submitted for a Veteran's Disability Claim is processed differently than a worker's compensation state claim. Past attempts have only allowed analysis within a single administrative system, rather than allowing the user to choose across a wide array of administrative rule sets that apply to any given examinee's circumstance. For example, using the aforementioned example, RateFast allows the clinical data set to be analyzed in either (or both) the Veterans' disability or workers' state compensation system. The RateFast platform allows the user to choose among a variety of administrative rules, to appropriately process the impairment claim.

Section 3: The Process

As described below, the method and system provides unique applications of logic and statistics to medical processes to obtain substantially improved accuracy in the measurement of a examinee's pathology due to an injury. These methods and the system incorporate strict protocols, or "Administrative Rule Sets" to direct the examination for the purpose of obtaining an optimal, accurate and reproducible data set, from which a rating of the impairment due to the pathology resulting from an injury can be determined. Additionally, within this method and system, a statistical analysis can additionally assist in obtaining an improved accuracy of impairment ratings. Consequently, the errors in the impairment rating presently carried forward through the disability, care and compensation phases of the process are avoided.

Figure 10:
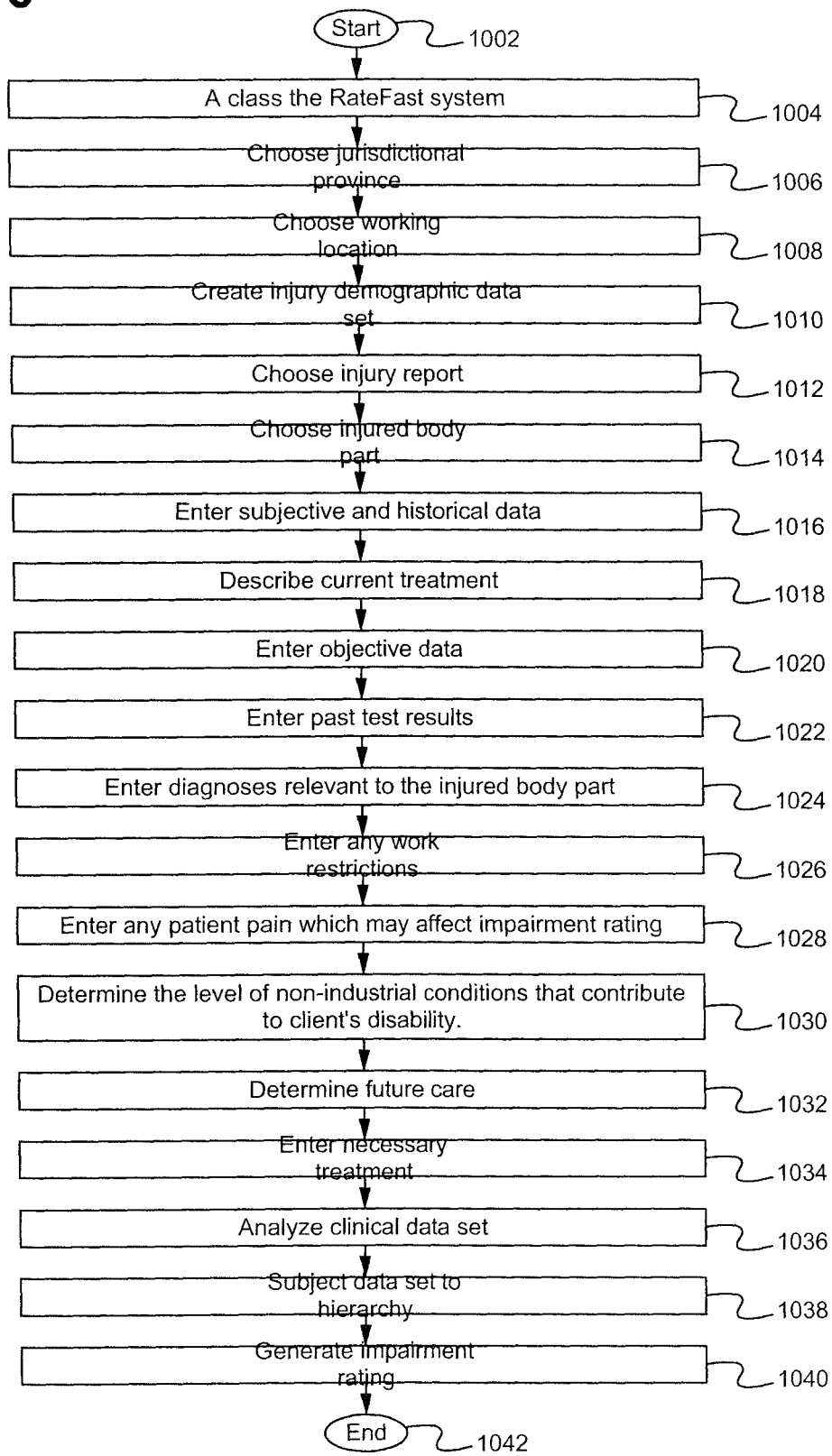
FIG. 10 illustrates a method of obtaining a high accuracy impairment rating in accordance with some embodiments.

Referring now to FIG. 10, a method of obtaining a high accuracy impairment rating according to the attributes as described above, is depicted therein. The method describes a process of calculating an impairment rating of the examinee (client) by a user (medical professional).

The method begins in the step 1002. In the step 1004, a user accesses the RateFast program with an electronic device and connects to the internet to create a user data set within the RateFast main frame. In some embodiments, the server model code software utilizes a redundant array of computer servers on which the majority of the software runs (user interface, calculation engines, etc.) A second array of redundant servers allows storage and indexing of user and claim data set. A user can access software through internet connected computer devices and secured login methods. In some embodiments, a small portion of software runs on the user's computing device. This enables software to more efficiently access the RateFast main frame data and improves performance. Alternatively, the software can be stored and operated on the user's device. In this alternative, the data taken in the exam can also be stored locally.

In the step 1006, the user chooses a jurisdictional province (state) relative to the client's injury. In some embodiments, a pictorial prompt such as a map of the United States is displayed. By selecting the jurisdictional province, the user is effectively automatically selecting the appropriate administrative rule set (ARS) that will be applied to the claim data set to be entered. In some embodiments, the ARS is chosen and suggested to the user by the RateFast software. The user verifies and validates the ARS as correct.

In the step 1008, the user is prompted to choose a working location based upon his or her profile. The profile includes an option to identify the state of origin of the client and can override the user's geographical default assigned by the user account. The system is capable of handling users and clients that work for and/or provide services in a diverse geographical environment. For example, a client with an employer bound by "state A" is injured and treated in "state B", is evaluated and an ARS is applied from "state A" by a treater in "state B". This allows the stakeholders to apply the correct ARS at the time of injury to correctly provide benefits as opposed to at a time remote from the date of the actual injury. Additionally, this increases the accuracy of the clinical data set (CDS) and avoids confusion, error, delay or the need for a reexamination in the home "state A" of the affected client.

The user is then directed to the client's injury demographic data set (IDDS). The user can then choose to edit data for an established client or create a new profile in the IDDS, in the step 1010. The user is prompted to enter and/or update information within the IDDS. The RateFast program validates the entered injury demographic data set to ensure the minimum required information has been entered to create a valid report required by the stakeholders and the ARS.

The user is then directed to a library of injury reports associated with the chosen IDDS, and in the step 1012 the user is prompted to choose an injury report on which to work from a list of available report options. The user is then guided to enter the CDS.

In the step 1014, the user selects an injured body part. For example, in some embodiments, the body part is selected from a drop-down menu or other appropriately desired selection field. In the step 1016, the user enters subjective and historical data such as examinee complaints, both general and specific to the activities of daily living, past medical and social history, including but not limited to medical conditions, medications, smoking and drug use, marital status, education, occupation(s), employment status and hobbies. The user can also enter information such as past surgical history. This information is stored in a separate library of information for use in subsequent claims or clinical data sets and additional utility of safety features for significant adverse outcomes. Occupational history can also be collected and stored for the comparison of impairment, not disability associated with occupation.

In the step 1018, the user enters information describing treatment of the current injury. This information can include any medications and associated side-effects, physical therapy, chiropractic therapy, acupuncture, durable medical equipment, any medical procedures, medical providers and or facilities participating in the care of current injury. Then, in the step 1020, objective data is entered. This can include but is not limited to objective data unique to the injured body part based on a physical examination, such as vital signs and biometric measurement of the injured body part. In the step 1022, diagnostic test results such as medical imaging studies, laboratory values, an ancillary test such as electrocardiogram and electromyogram are entered.

Then, in the step 1024, diagnoses relevant to the injured body part are entered. This includes but is not limited to International Classification of Diseases (ICD) codes. For example, in some embodiments, a user is prompted to choose from a menu of possible diagnoses and their associated ICD codes. The user can enter others not included on the menu. RateFast also automatically includes diagnoses including, but not limited to past medical, social, and surgical history. However, these can be excluded if desired.

In the step 1026, any work restrictions are entered. This includes but is not limited to any physical limitations and/or environmental surrounding limitations. In the step 1028, the user is then prompted to enter information including but not limited to the examinee's pain, which can affect the impairment rating. In the step 1030, the user is prompted to determine how much including but not limited to any, non-industrial conditions contribute to the client's permanent disability. This process is called apportionment. In the step 1032, future care, including necessary treatments or resources needed for the management of the permanent impairment (e.g. a claim that has been determined to be MMI) is entered and in the step 1034 the user enters the necessary treatment, including but not limited to therapeutic interventions and medication necessary for immediate management in a non-MMI claim.

After the complete claim data set has been entered, it is encrypted and transferred over the internet to the RateFast servers. In the step 1036, the clinical data set is decrypted and then analyzed by a calculation process automatically selected in response to the injured body region and the ARS as chosen by the user. This process can include, but is not limited to an internal consistency check to ensure congruency within a clinical data set (e.g. physical examination findings of a right shoulder injury should correlate with imaging findings on the right shoulder). Congruency within the CDS reduces the opportunity for error and also allows stakeholders to verify the accuracy of the report with independent validation. Impairment values are assigned according to the ARS. Within any given administrative rule set, there is a wide variety in scope and complexity for the criteria applied to any given body part. For example, an elbow is evaluated using different criteria than a knee. In the step 1038, the impairment values are subjected to the hierarchy of impairment processes, and in the step 1040 a single number, whole person impairment rating is generated.

A clinical report can be issued which draws information from the CDS and the calculated impairment rating. The clinical report can also be encrypted and sent to the user. Particularly, the clinical report can be sent to the user over the internet. The user can select from a variety of formats in which to receive the report. Most commonly, the user will receive a computer file in a portable document file (.pdf) format via email. Alternatively, the file can be sent to an electronic health record software program which contains the client's health records and to which the user has access. In some embodiments, users can also request a tailored, HIPAA-compliant search of the RateFast database to obtain a wide variety of medical and industrial impairment related information. For example, a private corporation can be interested in assessing the differences in the frequency and the degree of work-related injuries and resultant impairment ratings across various geographic locations and occupations. In the step 1042, the method ends. The finished report is signed by the user and the report can be formally issued to an appropriate stakeholder.

Section 4: The Ratefast Hub

Referring now to FIG. 1A, an example of a RateFast Hub Workflow is depicted therein. The RateFast Hub implements the RateFast method, such as described above and below. The RateFast Hub enables interested parties, with permission to search the RateFast database, including the RateFast Hub to obtain a wide variety of stored medical and industrial impairment related information.

A RateFast Hub is comprised of HIPPA compliance, permission accounts of stakeholders including but not limited to the benefit of human resources input data upon hire, share demographics with doctors, allow pre-placement exams to establish injury baselines, and on file formal job descriptions using both pre and post injury examinations to obtain compliance with the Americans with Disabilities Act (ADA) and assessing a "reasonable accommodation" consideration by the employer. In addition, the RateFast hub supplies work functional limitations to the employee environment so they can compliant with the ADA.

Stakeholder access requests and/or approval for treatments can include but is not limited to; medications, diagnostic imaging, specialty consultations, and evidence of objective documentation of improvement of the injured individual. The RateFast Hub can find active practices accepting specific body part injuries within an active Medical Provider Network (MPN) and share RateFast administrative and medical data. This streamlines the delivery of data and enables stakeholders such as an employer, a worker and a treating doctor to identify one another in a HIPPA compliant environment resulting in more accurate and timely delivery of care.

The RateFast hub also expedites the process of specialized accommodations such as but not limited to fit for duty exam, return to work exam, communicating work restrictions, work capacity and work tolerance in compliance with the job description format. Additionally, the RateFast data can be "owned" by a stakeholder (e.g. employer, insurance carrier, physician) allowing the owner to invite or un-invite parties to participate in treatment and/or administrative events of the injured individual.

Figure 1B:
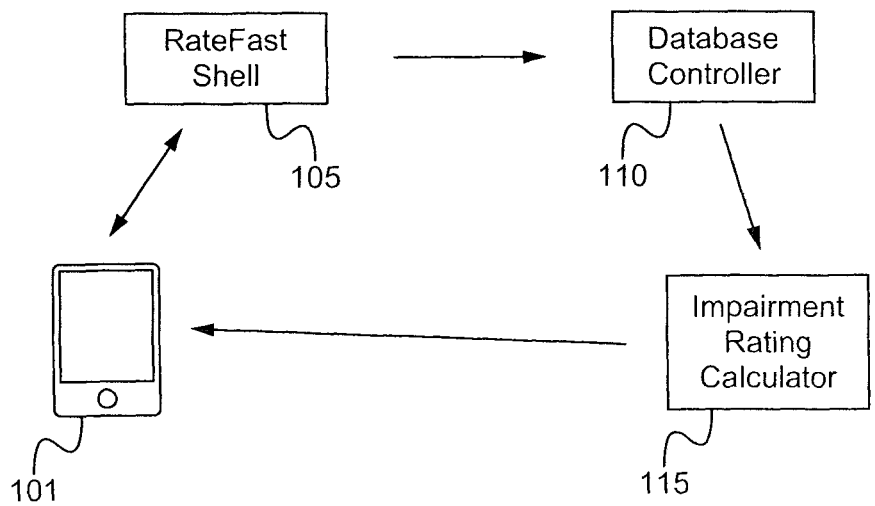
FIG. 1B illustrates a Ratefast system in accordance with some embodiments.

As shown within FIG. 1B, the RateFast system comprises three separate and interconnected processes. The system 100 comprises a shell 105, a database controller 110 and an impairment rating calculator 115. The RateFast shell 105 is operatively coupled to an electronic device 101, such as described above and controls a graphical user interface that guides a user through the data collection and entry process described above. In some embodiments, the RateFast shell 105 also alerts the user when a "real time" collection of data results in a non-valid calculation required by the ARS. The shell 105 collects both user-related information and claim data sets entered by the user. The RateFast shell 105 is also able to communicate with the electronic device 101 to place a "thin-client" program on the device 101 to facilitate the user input. The RateFast shell 101 also preferably encrypts the user inputted data and passes the claims data sets to the database controller 110 for storage.

The database controller 110 stores, indexes, and retrieves all user and claim data sets and any calculations performed on those data sets. The data sets are received at the impairment rating calculator 115, which comprises a set of spreadsheets into which the clinical data sets are imported and subject to the hierarch of impairment, such as described above. After an impairment rating is calculated, the clinical report is encrypted and sent to the user and the electronic device 101.

Section 5: General Description of the Algorithms and Approach

Shell logic manages the collection of the administrative rule set (ARS) and the clinical data set (CDS) within the RateFast system. Type 1 shell logic performs validation calculations at the level of the user interface. For example, in some embodiments, clinical data is validated by the analysis of the appropriate ARS and instructing if additional CDS is needed. This logic prompts the user to enter additional physical exam findings and to expand the clinical data set if it is required by the administrative rule set. The shell logic either expands the existing clinical data set with simply more data or creates an additional set of data by prompting another unique physical activity.

During the collection of the CDS, the ARS interrogates the CDS for anomalies including but not limited to similar values outside of the expected data range. In this manner, the CDS can properly be interpreted as authentic and not otherwise synthesized. The shell logic optimizes the user's time by prompting only for clinical data as necessary for the final production of a specific impairment report. Additionally, the method provides the added benefit of standardization of the content impairment reports that otherwise might contain either extraneous information or have omitted information necessary for a correct impairment rating calculation.

Type 2 shell logic (nested) can drive, but is not limited to the clinical data set collection sequence. For example, the presence or absence of medication and clinical side effects if present, can allow additional assignment of impairment ratings based on the CDS and based on the treatment burden and/or sustained side effects as a consequence of permanent ongoing treatment.

Figure 16:
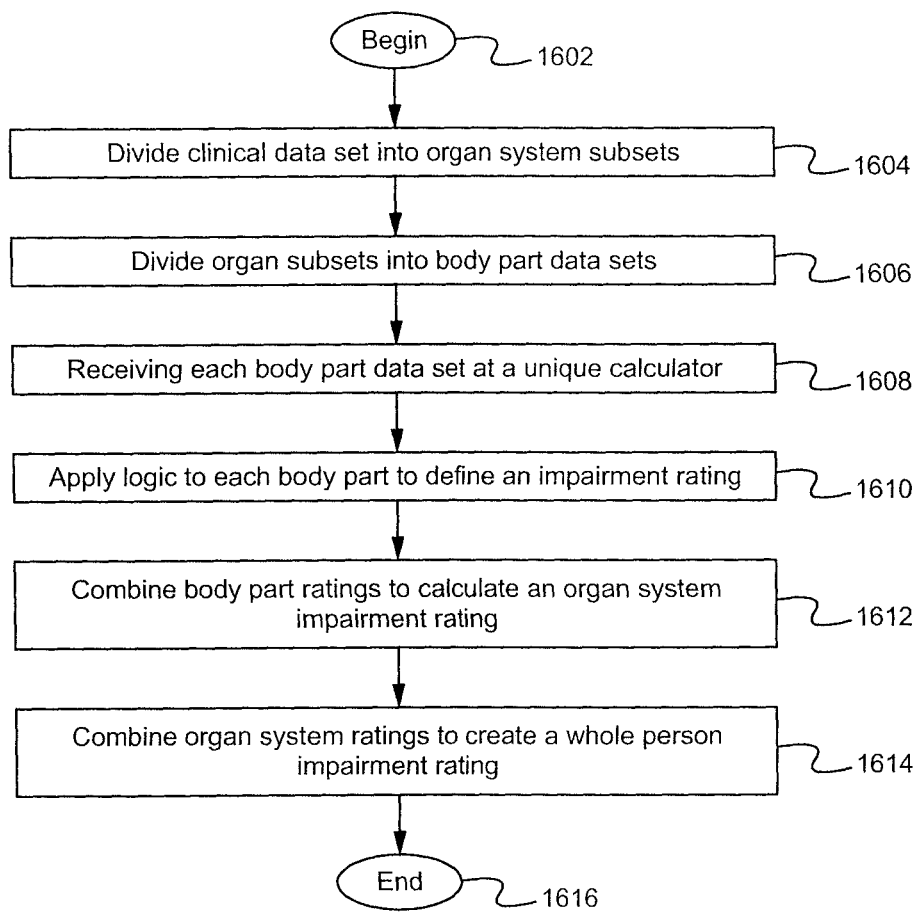
FIG. 16 illustrates a method of calculating an impairment rating based upon an observed clinical data set in accordance with some embodiments.

The application of the ARS to the specific injury has with it, an associated algorithm. Hence, extensive logic is contained within the impairment calculators, which are separate from the shell program. Data entered via the shell is imported into data fields in calculator, then applied to criteria defined by the ARS to determine a return value, if any. Once a complete set of return impairment values has been determined for all criteria defining impairment, those values are subject to the additional calculations to determine a final impairment rating for a specific body part. FIG. 16 illustrates a process of calculating an impairment rating.

The method begins in the step 1602. In the step 1604, the entire clinical data set is divided into organ system subsets. The organ system subsets (e.g. lower extremity) are then further divided into body part data sets in the step 1606. The body part data sets are all members of the organ system subset. For example, the knee and ankle are body part data sets of the single organ system, "lower extremity."

In the step 1608, each organ system member (e.g. knee) has a unique calculator that receives that data subset. Likewise, each body part data has a calculator that receives that ratable data set (RDS).

In the step 1610, the body part calculator (e.g. knee) then applies logic to determine numerical values for each criterion which define impairment for each body part data subset (e.g. skin loss, loss of strength, limb length discrepancy, and muscle atrophy). This is an example of the RDS. Keeping with logic defined by the ARS, additional calculations are performed on the RDS, in the step 1612. This involves evaluating all allowable combinations of ratable data points to calculate the highest allowable impairment rating specific to the body part data set.

In cases of multiple injured organ systems (e.g. both knees), the appropriate ratable data set is first generated for each body part. Subsequently, in the step 1614, additional logic is applied which combines all body part ratable data sets within one organ system to calculate an impairment rating for that injured organ system (e.g. "lower extremity").

Then, in the step 1616, further logic is then applied combining all organ system impairment ratings into a final whole person impairment rating. The method ends in the step 1618.

RateFast includes limitations in the 34 possible activities of daily living (ADLs) as input on rating in every upper extremity body part. This is a requirement in correctly calculating impairment ratings. Existing techniques exclude ADLs from their calculations and thus are unable to calculate specific whole person impairment ratings based on objective data. instead, existing techniques return a range of possible impairment ratings rather than a single, specific number. The inventory of ADLs within RateFast allows indexing of ADL restrictions to each injured organ system and each body part within that organ system. RateFast defines ADL restrictions as "can perform but painful" and "can not perform, with or without pain." Including these different levels of ADL restriction improves the accuracy of the impairment rating as they impact the individual.

To evaluate strength, the date of injury is used to determine if loss of strength can be included in the ratable data set. Date of surgery, if any, is used to determine if loss of strength can be included in the ratable data set. Presence of pain in the injured side can exclude strength data from the ratable data set. If pain is present in the injured side, the user is provided an option to use clinical judgment as to whether the pain precludes a full and maximal effort during the physical examination of the upper extremity. Additional screening for "any other condition" preventing full and maximal effort during the physical examination of the upper extremity.

Section 6: Apportionment of Activity Limitation

Apportionment is the assigning of percentages of a permanent disability determination resultant from permanent impairment. The AMA Guides $5^{th}$ Edition discusses the concept of disability as follows, "[t]he term disability has historically referred to a broad category of individuals with diverse limitations in the ability to meet social or occupational demands. However, it is more accurate to refer to the specific activity or role that the 'disabled' individual is unable to perform. Several organizations are moving away from the term disability and instead are referring to specific activity limitations to encourage an emphasis on the specific activities the individual can perform and to identify how the environment can be altered to enable the individual to perform the activities associated with various social or occupational roles." (Table 1-1.4) [AMA Guide $5^{th}$ Ed., page 8]

The RateFast method performs apportionment on the basis of a direct contribution of permanent impairment as required as the precursor to permanent disability. As the AMA Guides $5^{th}$ Edition states, "[a]n alteration of an individual's capacity to meet personal, social, or occupational demands because of an impairment." (Table 1-1) [AMA Guide $5^{th}$ Ed., page 3] RateFast performs apportionment of activity limitations and/or functional limitations as it directly affects permanent impairment.

Permanent disability or a permanent disability rating (PDR) is multifactorial calculation based on jurisdictional or administrative rule sets (ARS). For example, an individual's demographic may or may not include an earning potential and a consideration of vocation. The apportionment of all considered factors shall not exceed 100%. The factors of non industrial apportionment are those which arise from factors other than those arising out of employment (AOE). Apportionment is done without consideration of avocation. Fore example, the AMA Guides $5^{th}$ Edition states, "[t]he whole person impairment percentages listed in the Guide's estimate the impact of the impairment on the individual's overall ability to perform activities of living, excluding work, as listed in Table 1-2." [AMA Guide $5^{th}$ Ed., page 4]

RateFast incorporates an adjusted pain value (APV) method, as described throughout this text to create digital models of an individual's permanent disability that is; 1) consistent, 2) data driven, 3) mathematically precise, 4) uniquely bounded by the conditions being considered, 5) based on both measurable loss and functional limitations, and 6) weighted on methods consistent with philosophy, magnitude, and values consistent with the ARS.

For example, an individual twists a knee at work and now hurts. Recovery is limited by pre-existing arthritis, now symptomatic. The individual makes a less than complete recovery after available treatment is rendered, due to the arthritis. The knee arthritis is considered a non-industrial apportionable factor.

50% is due to the accepted injury and 50% is due to the pre-existing arthritis. The apportionment is valuable to the stakeholders as it assigns liability and benefits that are owed or not owed by the stakeholder assuming the risk. For example, if $1,000 is owed for an accepted injury liability, $500 is the responsibility of the stakeholder assuming the risk for the accepted injury. Particularly, the apportionment must be based on substantial medical evidence, objective, and consistent in approach and reasoning.

In another case, complications arising from a degenerative joint disease such as arthritis are objectively measured (mild or 3 mm joint space, moderate or 2 mm joint space, severe or 1 mm joint space, bone on bone, 0 mm joint space). The complications are measured according to a reasonably medically accepted result in pain, symptoms, measurable loss, and functional loss and weighted in a way to reflect a direct effect on permanent disability.

The apportionment must take into account functional limitations (eg ADLs) and as reflected by pain and/or organ system loss. The interplay of pain and organ or body system loss is a complex relationship, with both concepts requiring representation in the apportionment process, as both can contribute to permanent disability (administrative and/or open labor market) derived from permanent impairment. The AMA Guides 5$^{th}$ Edition defines ADLs as a reflection of permanent impairment, not disability, "[i]mpairment ratings were designed to reflect functional limitations and not disability." [AMA Guide 5$^{th}$ Ed., page 4] For example, pain can limit the functional use of an arm, but there is no measurable loss for range of motion, strength, sensory, etc. The result is a functional limitation. Or there is no pain, but there is an amputation (organ or body system loss). The result is a functional limitation. Additionally, there can be a combination of both. Pain limits some ADLs and amputation limits a few. Combined, this condition results in many ADL limitations. The weighted on methods are consistent with philosophy, magnitude and values consistent with the ARS.

To create the digital apportionment model, two or more independent conditions are constructed absent the impact of the other and total contributing factors are assigned for consideration. For example, arthritis, obesity and other pre-existing injuries can be contributing factors to a knee injury. The objective tolerance ranges can be defined. Or obesity classes I-III as defined by the World Health Organization (WHO) can be assigned by a subtraction method. The model can be created by subtracting the contributing apportionable factors from the native injury model.

A contribution model can be created by assigning percentage for each apportionable factor, not exceed 100% contribution. An injury can have zero percent apportionment assigned to non-industrial factors or can have 100% assigned to non-industrial factors.

Figure 20:
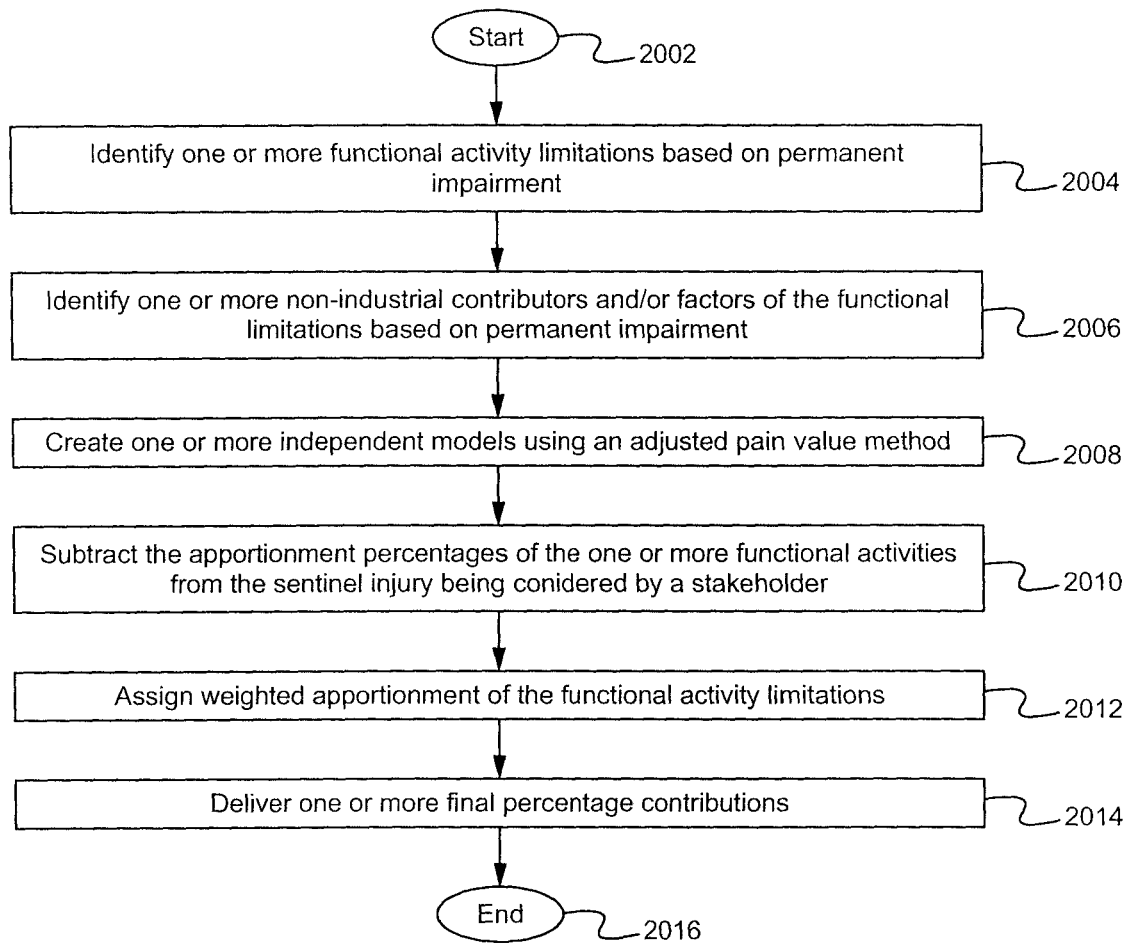
FIG. 20 illustrates a method of constructing an apportionment of a permanent disability determination resulting from a permanent impairment in accordance with some embodiments.

FIG. 20 illustrates a method of constructing an apportionment of a permanent disability determination resulting from a permanent impairment. The method begins in the step 2002. In the step 2004, one or more functional activity limitations based on permanent impairment are identified. In the step 2006, one or more non-industrial contributors and/or factors of the one or more functional activity limitations based on the permanent impairment are identified. Then, in the step 2008, one or more independent models using an adjusted pain value method are created. In the step 2010, the apportionment percentages of the functional activity limitations are subtracted from the sentinel injury being considered for the stakeholders. In the step 2012, weighted apportionment of the functional activity limitations are assigned and in the step 2014 a final percentage of each contribution is delivered. The method ends in the step 2016.

Section 7: The ADL Subset of the CDS Allows Incorporation of Clinical Influence of the Final Impairment Rating Under the AMA's Guide to the Evaluation of Permanent Impairment "[t]wo measurements made by the same Examiner using the Guides that involve an individual or an individual's functions [are] consistent if they fall within 10% of each other. Measurements should also be consistent between two trained observers by one observer on two separate occasions, assuming the individual's condition is stable. Repeating measurements can decrease error and result in a measurement that is closer to average function." [AMA Guide, page 20] A unit of functional measurements can include, but is not limited to degrees of motion (D), or a linear distance such as centimeters, or a measurement of force (e.g. kilograms ((kg)) or pounds ((lbs.)) or millimeters of mercurial force (e.g. mm Hg in blood pressure).

The AMA Guide, however, does not instruct a user how to calculate the 10% variance of functional measurements. Further, the AMA Guide does not provide any clinical examples as demonstrations of how a user should arrive at the 10% determination for validation.

The RateFast system calculates the 10% standard of variance (index of % variance ((I % V)) defined as % variance for 1D of difference) based on degrees of expected motion, which applies a fixed value to a known distance between two functional measurements, where each degree of variance is equally weighted for impairment value, not the ratio of two numbers because it is now defined as "bounded by a defined plane of motion expressed in D where both measurements are within the AMA Guides" and "expected normal" set range are provided by the AMA Guides master text and corrected with the March 2003 Errata.

Using the ratio of two measurements (e.g. 1−smaller measurement/larger measurement) will result in inequity for the examinee who has a higher burden of impairment having a higher likelihood of invalidation of his/her measurements, because as the size of the two measurements increase, the higher the likelihood of validation, and as the size of the two measurements decrease, the lower the likelihood of validation. This method leads to inequitable outcomes that are propagated forward and result in errors for all stakeholders and can lead to measurement size bias.

For example, Examinee A has two degrees of motion measurement numbers of 176D and 165D, which account for a variance equal to 1−(165/176)=0.0625, or 6.2%. These measurements are valid because there is <10% variance and the measurements are therefore consistent. In another case, Examinee B has two degrees of motion measurement numbers of 1D and 2D. Examinee B has the higher burden of impairment, which leads to an invalidation of the measurements at 1−(½)=0.5, or 50%, which is >10%.

In situations when a functional measurement falls within the normal expectation of the bounded data set, the function of the calculation of expected values established by the AMA Guide's 10% variance is mathematically expressed as follows: 100%/(x+y)=% variance per degree measured, where 100% is defined as the total value of data set range, and x is the value of the first data range from 0 measurement reference point, and y is the value of the data range complimentary to x, but in the opposite direction, if applicable.

This standardization method and approach equally weighs and defines 1D of difference between the distance of two measurements in a single data set within the expected range of motion in a plane of motion provided by the AMA Guide and corrected with the March 2002 Errata (e.g. a measurement that is greater than that expected from the "normal" expectations of the AMA Guide 5th ed.).

For example, in the case of a shoulder plane of motion flexion/extension, the AMA Guide defines the flexion endpoint of normal to be 180D and extension endpoint 40D based on a OD reference in the vertical plane. The full set range is 180D+40D=220D. The full range of possible "normal" degrees is defined at having 100% value divided by the number of degrees in the expected range. For the shoulder flexion/extension plan of the shoulder, this is expressed as 100%/total number of degrees in the set range, or, 100%/220D=0.45% I % V, or, 1 degree of variance is worth 0.45%. In this example 10% validation variance cut off is 10%/0.45=22.2D or difference tolerance between any two measurement numbers as "Valid" and <22D difference tolerance between any two measurements>23D as "Invalid".

When a functional measurement exceeds the boundaries, the I % V must be re-calculated (e.g. "adjusted and/or recalculated) based on the expansion of the data range endpoints re-defined and collected from the examinee, which now define a new range for the data range endpoints that were previously defined by the expected "normal". The AMA Guide's data for reasons of maintaining consistency and accuracy are now adjusted and "re-defined" based on the examinee's actual endpoints at either the high and/or low end of the of the data set tolerance. In situations when a functional measurement falls outside the normal expectation of the bounded data set, the function of the calculation of expected values established by the AMA Guide's 10% variance is mathematically expressed as follows: $100\%/(((x+x'))+((y+y')))=\%$ variance per degree measured, where 100% is defined as the total variance value of the data set range, and x is defined as the range of the "normal" expectation, and x' is defined as the number of D beyond x, and y is defined as the range of the "normal" expectation, and y' is defined as the number of D beyond y. This standardization method and approach equally weighs and defines 1D of difference between the distance of two measurements in a single data set exceed the expected range of motion in a plane of motion provided by the AMA Guide and corrected with the March 2002 Errata (e.g. a measurement that is greater than that expected from the "normal" expectations of the AMA Guides 5th ed.)

For example, in the case of a shoulder plane of motion flexion/extension, such as described above, the AMA Guide defines the flexion endpoint of normal to be 180D and extension endpoint 40D based on a 0D reference in the vertical plane. The full set range is 180D+40D=220D. The full range of possible "normal" degrees is defined at having 100% value divided by the number of degrees in the expected range. For the shoulder flexion/extension plan of the shoulder, this is expressed as 100%/total number of degrees in the set range, or, 100%/220D=0.45% I % V, or, 1 degree of variance is worth 0.45%. In this example 10% validation variance cut off is 10%/0.45=22.2 D or difference tolerance between any two measurement numbers as "Valid" and <22D difference tolerance between any two measurements>23D as "Invalid".

When functional measurements are obtained beyond the expected data range of motion such as flexion trial 1=190D; and trial 2=175D flexion (e.g. expected normal 180D) and extension trial 1=66D; and trial 2 D=67D (e.g. expected normal 40D) the 10% variance method of $100\%/(((x+x'))+((y+y')))=\%$ variance per degree measured, where 100% is defined as the total variance value of the data set range, and x is defined as the range of the "normal" expectation, and x' is defined as the number of D beyond x, and y is defined as the range of the "normal" expectation, and y' is defined as the number of D beyond y. Therefor x is the expected AMA Guide's upper bound of a "normal" flexion motion for the examinee (x=180D) and x' is the difference the examinee's highest measurement minus the expected upper bound (x'=190D-180D=10D) and y is the expected AMA Guides upper bound of a "normal" extension motion for the examinee (y=40D) and y' is the difference the examinees highest measurement minus the expected "normal" upper bound (y'=67D-40D=27D). Therefore the I % V value using the RateFast method is $100\%/(((x+x'))+((y+y')))$; or $100\%/(((180+10))+((40+27))) 100\%/(190+67)=0.39$.

For bounding data ranges in two or more independent data sets where two or more sets exceed the expected range of motion in a single data set in a plane of motion equal the conditions when a single data set functional measurement fall within the guidelines of the AMA Guide. In situations when functional measurements of two or more sets exceed fall outside the normal expectation of the bounded data set, the function of the calculation of expected values established by the AMA Guide's 10% variance is mathematically expressed as follows: Set A is defined as $100\%/(((x+x'))+((y+y')))=\%$ variance per degree measured, where 100% is defined as the total variance value of the data set range, and x is defined as the range of the "normal" expectation, and x' is defined as the number of D beyond x, and y is defined as the range of the "normal" expectation, and y' is defined as the number of D beyond y. Set B is defined as $100\%/(((x''+x'''))+((y''+y''')))=\%$ variance per degree measured, where 100% is defined as the total variance value of the data set range, and x" is defined as the range of the "normal" expectation, and x''' is defined as the number of D beyond x", and y" is defined as the range of the "normal" expectation, and y''' is defined as the number of D beyond y.

This standardization method and approach equally weighs and defines 1D of difference between the distance of two measurements in two or more independent data sets where two or more sets exceed the expected range of motion in a plane of motion provided by the AMA Guide and corrected with the March 2002 Errata (e.g. a measurement that is greater than that expected from the "normal" expectations of the AMA Guides 5th ed.)

Example Set B: in the case of a shoulder plane of motion flexion/extension, such as described above, the AMA Guide defines the flexion endpoint of normal to be 180D and extension endpoint 40D based on a OD reference in the vertical plane. When functional measurements are obtained beyond the expected data range of motion such as flexion trial 1=190D; and trial 2=175D flexion (e.g. Expected normal 180D) and extension trial 1=66D; and trial 2 D=67D (e.g. Expected normal 40D) the 10% variance method of set A is $100\%/(((x+x'))+((y+y')))=\%$ variance per degree measured, where 100% is defined as the total variance value of the data set range, and is defined as the range of the "normal" flexion expectation, where x is defined as the number of D, and x' is defined as the number of D beyond x, and y is defined as the range of the "normal" extension expectation, and y' is defined as the number of D beyond y. Therefore x is the expected AMA Guides upper bound of a "normal" flexion motion for the examinee (x=180D) and x' is the difference the examinee's highest measurement minus the expected upper bound (x'=190D-180D=10D) and y is the expected AMA Guide's upper bound of a "normal" extension motion for the examinee (y=40D) and y' is the difference the examinee's highest measurement minus the expected "normal" upper bound (y'=67D-40D=27D). Therefore the I % V value using the RateFast method is 100%/(((x+x'))+((y+y'))); or 100%/(((180+10))+((40+27))=100%/(190+67)=0.39.

Example Set B: in the case of a shoulder plane of motion flexion/extension, such as described above, the AMA Guide defines the flexion endpoint of normal to be 180D and extension endpoint 40D based on a 0D reference in the vertical plane. When functional measurements are obtained beyond the expected data range of motion such as flexion trial 1=200D; and trial 2=175D flexion (e.g. Expected normal 180D) and extension trial 1=75D; and trial 2=67D (e.g. Expected normal 40D) the 10% variance method of set B is 100%/(((x"+x'"))+((y"+y'")))=% variance per degree measured, where 100% is defined as the total variance value of the data set range, and is defined as the range of the "normal" flexion expectation, where x" is defined as the number of D, and x'" is defined as the number of D beyond x", and y" is defined as the range of the "normal" extension expectation, and y'" is defined as the number of D beyond y". Therefore x" is the expected AMA Guide's upper bound of a "normal" flexion motion for the examinee (x=180D) and x" is the difference the examinee's highest measurement minus the expected upper bound (x"=200D-180D=20D) and y" is the expected AMA Guides upper bound of a "normal" extension motion for the examinee (y"=75-40D=35D) and y" is the difference the examinee's highest measurement minus the expected "normal" upper bound (y'=75D-40D=35D). Therefore the I % V value using the RateFast method is 100%/(((x+x'))+((y+y'))); or 100%/(((180+20))+((40+35))=100%/(200+75)=0.36.

In sum, as described above, the RateFast approach uniquely assigns a bounded range for both normative measurements and measurements which are outside of the normative expected range allows more accurate comparison to any possible measurement obtained and assigns equal comparison regardless of the size of the measurement numbers of the examinee, therefore removing the problem of measurement size bias.

Section 8: Body Region and System Specific Discussions and Algorithms

Upper Extremities

The algorithms involving the Upper Extremities are found in FIGS. 2A-2D. These algorithms are the result of the interactive Administrative Rule Sets (ARS) arising from the potential of a multilateral pathologies both within the upper extremities and with the other structures and systems as well. An example of the combined ARS's is a correction in calculating upper extremity impairment when range of motion limitation, including hypermobility, is combined with loss of strength in separate planes of motion.

Figure 2A:
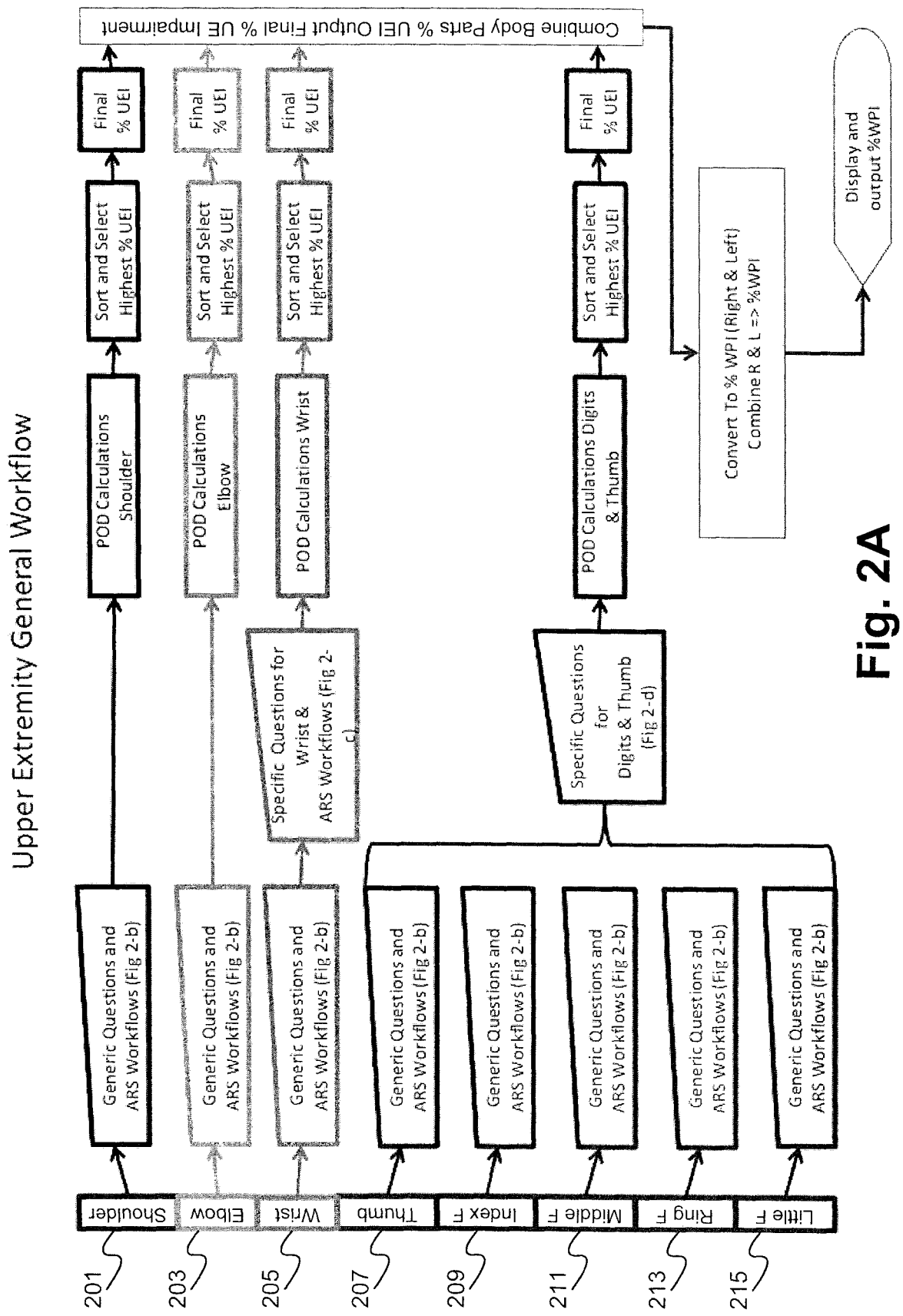
FIGS. 2A-2D illustrate upper extremity impairment algorithms in accordance with some embodiments.
Figure 2B:
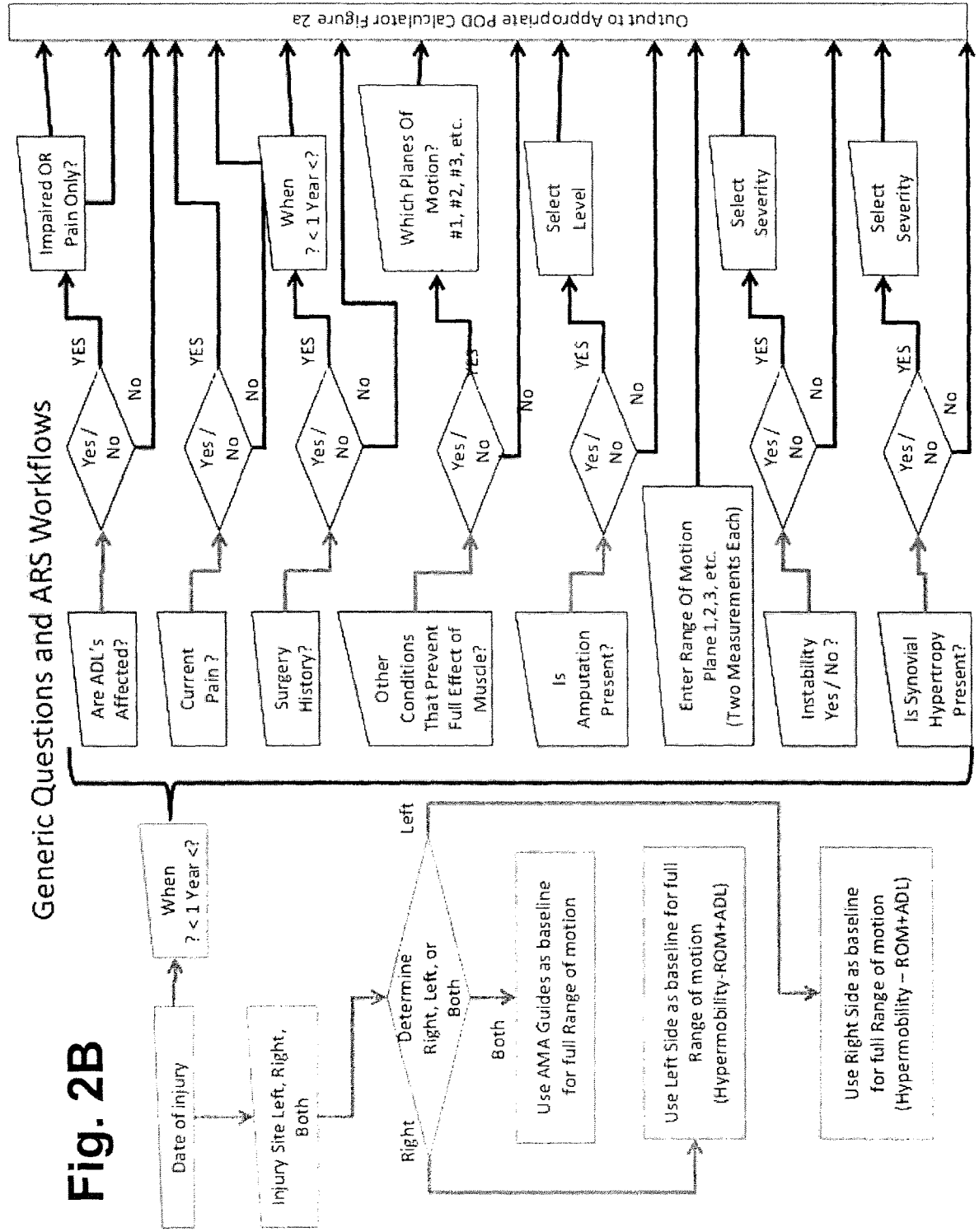
Figure 2C:
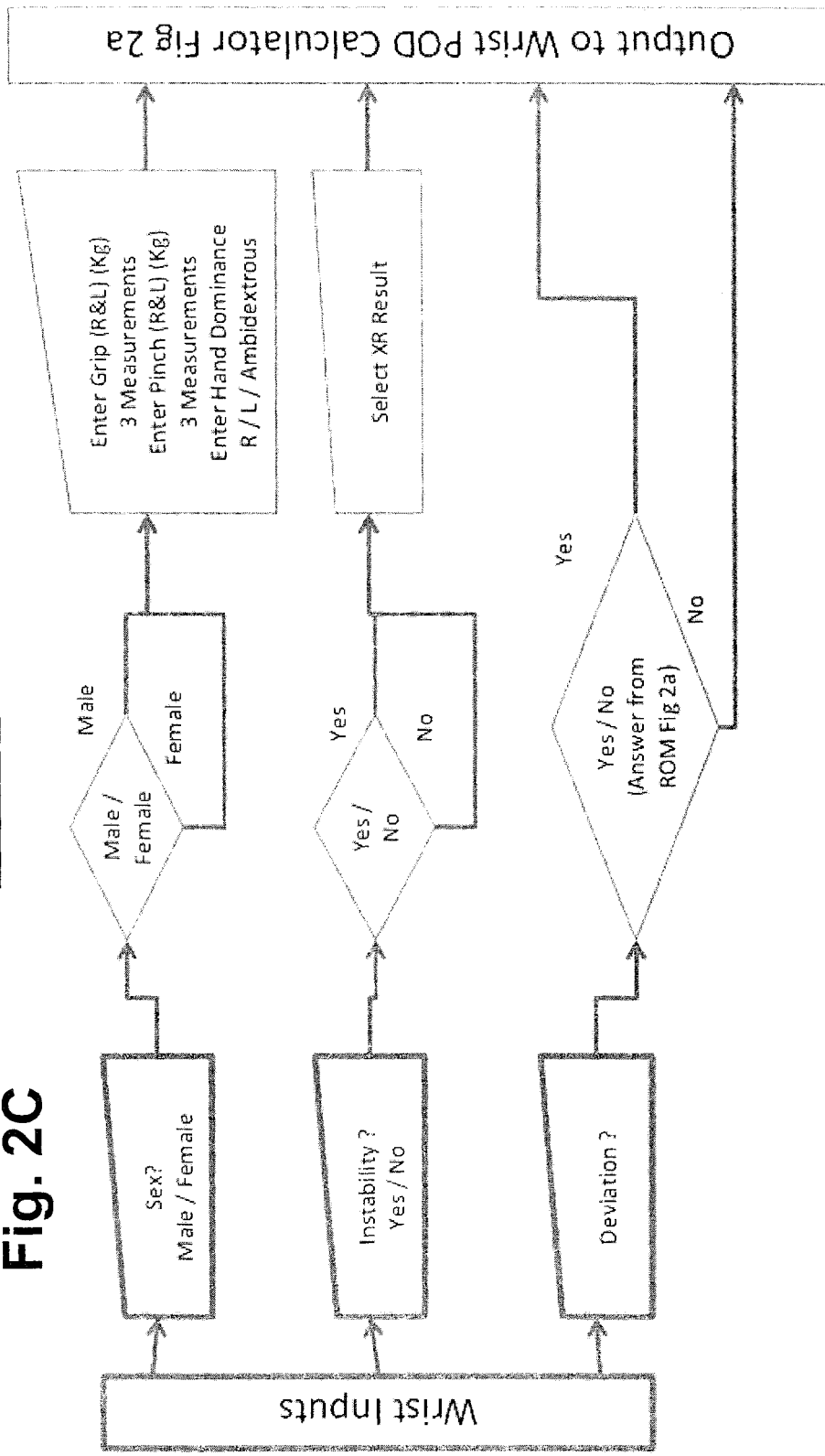
Figure 2D:
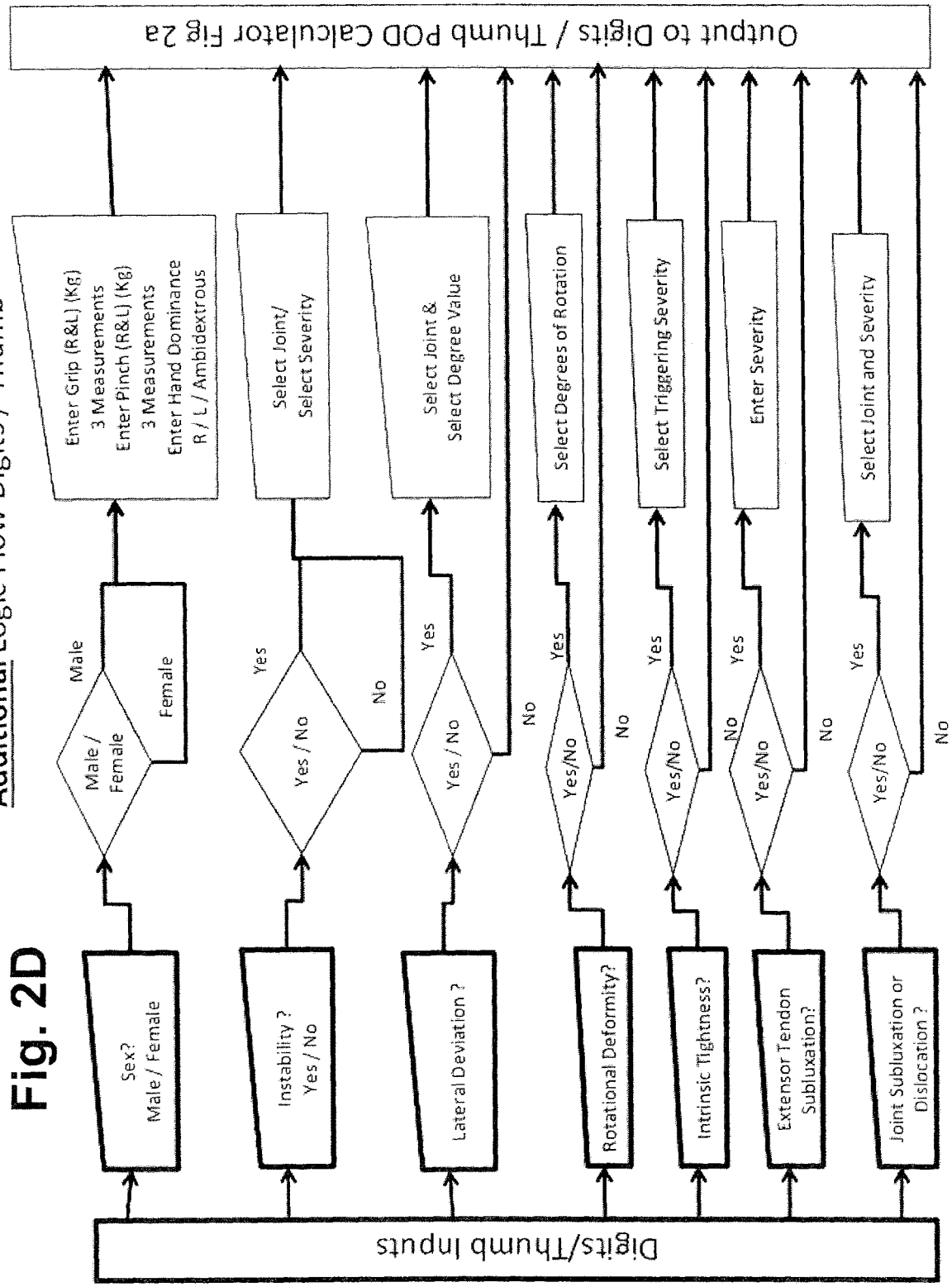

Existing rating engines (e.g. AMA Guides 5 and 6 ed) do not appropriately account for the combination of a loss of strength with full range of motion in one plane of motion with a limited range of motion in another. RateFast appropriately allows this combination of deficits in calculating upper extremity impairment. Additionally, existing rating engines do not report separate impairment values for each body part in the upper extremity, only reporting a combined impairment value for the shoulder, elbow, and wrist. RateFast provides the user with separate impairment values for each body part that is evaluated, such as shown in FIG. 2A. Each body part; shoulder 201, elbow 203, wrist 205, thumb 207, and fingers 209, 211, 213, and 215 of the upper extremity are subjected to the ARS workflows of FIG. 2B. Combining each impairment rating for each body part of the upper extremities allows RateFast to correctly calculate an overall impairment rating for the upper extremity.

Hypermobility is a condition where the combination of an excessive range of motion (ROM) beyond that described in the AMA Guides and the Activities of Daily Living are not impacted or affected. Hypermobility is a condition that includes but not limited to hyperextension, hyperflexion, subluxation, hyperlaxity, and dislocation. This condition, though not normal, is common enough and significant enough to merit examination for its presence in the writing of the AMA Guide, where it is stated, "[i]f an involved joint has 'normal' motion according to the values specified in the Guides and the contralateral uninvolved joint has greater than average motion, there is a relative loss of motion a zone beyond the normal values does not as a rule represent a loss of function or impairment." [AMA Guide, page 455] It further states that, "[i]n rare cases, based on the Examiner's clinical judgment, an impairment percent not to exceed 2% of the maximal regional impairment value of a unit of motion can be given. The rationale for this decision must be explained in the report." Hypermobility is described in FIG. 2B.

Applying an impairment value for hypermobility requires the following considerations: 1) define if hypermobility is present and validated, 2) define if the hypermobile state is a permanent impairment by examination of the condition's impact on the individual's ADLs, and 3) determine the value of the permanent impairment not to exceed 2% of the maximum regional impairment value of a unit of motion based on the extent to which the ADLs impact the individual.

Six clinical criteria define upper extremity muscle strength in the context of the disability evaluation. Based on clinical examination, the Examiner assigns a value from 0 through 5 for each criterion. However, current calculators only allow values of 3 or 4 for each criterion; values of 0, 1, 2, and 5 are not available. RateFast allows the user to enter any number from 0 to 5 for each criteria and assigns corresponding impairment values based on extrapolation of guidelines outlined in existing administrative rule sets for the values of 3 and 4.

For the shoulder 201, there is a determination of the presence of pain in all 6 planes of motion in an injured shoulder. There is also a determination of the presence of "any other condition" which prevents full and maximal effort during the physical examination of the shoulder. Existing techniques incorrectly calculate shoulder instability in that an impairment value related to instability is combined with an impairment value related to an arthroplasty procedure when calculating upper extremity impairment. RateFast corrects this error by not allowing combination of these 2 values.

Additionally, existing techniques calculate shoulder impairment based on range of motion limitation incorrectly for shoulder extension and adduction between 30 and 40 degrees. These errors also result in incorrect calculation impairment ratings based on of loss of strength when shoulder range of motion (in adduction and extension) is between 30 and 40 degrees. RateFast uses the corrected values for range of motion as found in the errata to AMA Guide. Existing inventions also do not allow inclusion of impairment values related to loss of strength when there is concomitant loss of range of motion in shoulder flexion, abduction, external rotation, and internal rotation. RateFast correctly includes loss of strength when the range of motion in any plane is within normal limits as defined by the errata to the AMA Guide.

To evaluate the elbow 203, RateFast performs an impairment rating for persistent joint subluxation or dislocation not provided in existing techniques. Existing techniques do not allow inclusion of impairment values related to loss of strength when there is concomitant loss of range of motion in elbow flexion, extension, supination, or pronation. RateFast correctly includes loss of strength when the range of motion in any plane is within normal limits as defined by the errata to the AMA Guide.

For the wrist 205, fingers 209-215, and thumb 207, the RateFast platform allows inclusion of pinch strength for each finger independently. This allows strength deficits in any finger to be included in the impairment rating. RateFast allows impairment calculation based on loss of grip strength for an injured wrist even when the uninjured wrist is unable to serve as a baseline (e.g. amputation of the uninjured side). For unilateral wrist injuries, RateFast adds a new option that medial-lateral deviation in the uninjured side be measured as a reference to which the injured wrist is compared. Existing techniques do not allow these ratings based on actual measurements of the wrist motion deviation, but rather allow direct input of the impairment selection without measurements or validation required.

Lower Extremities

Figure 3A:
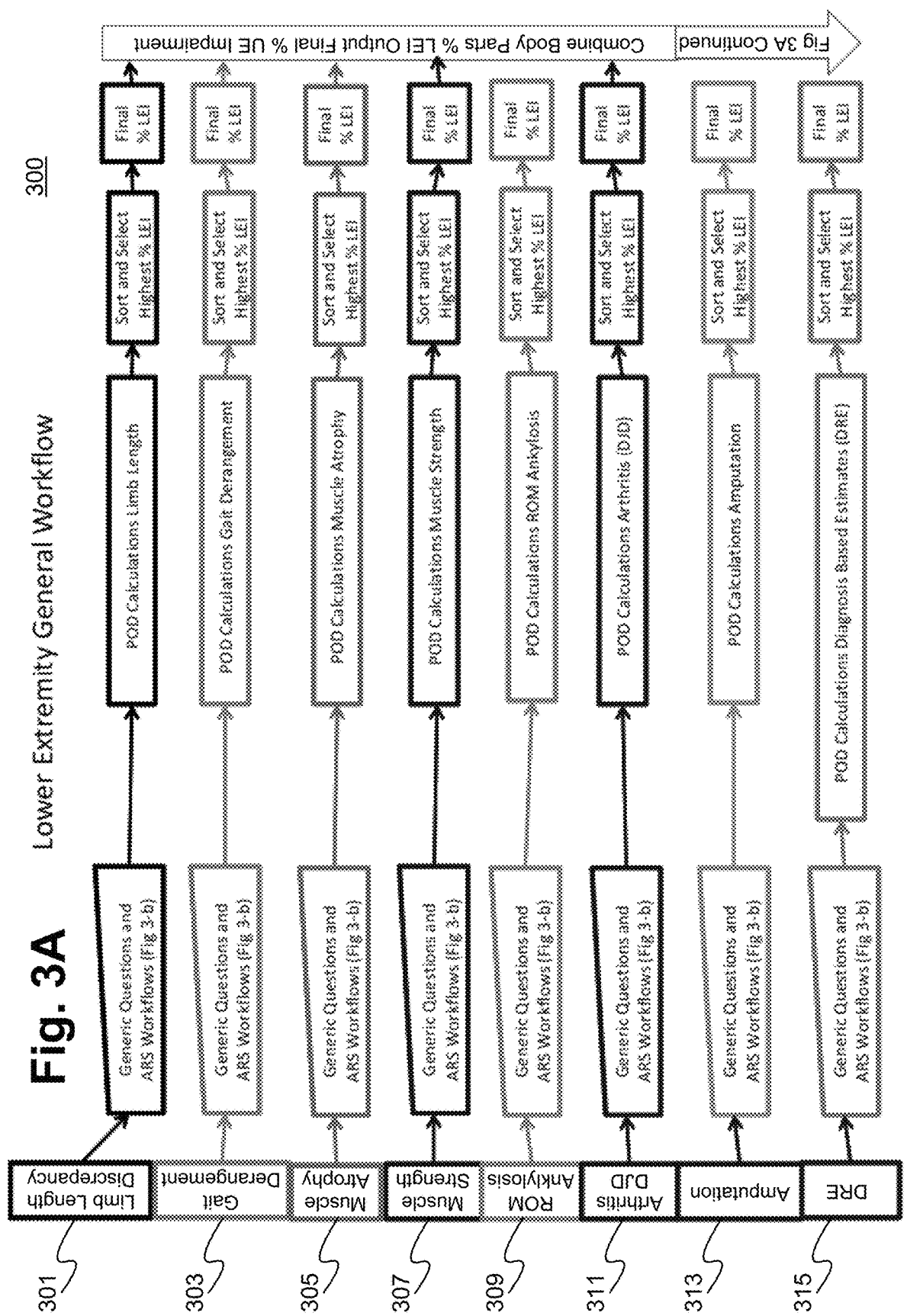
Figure 3B:
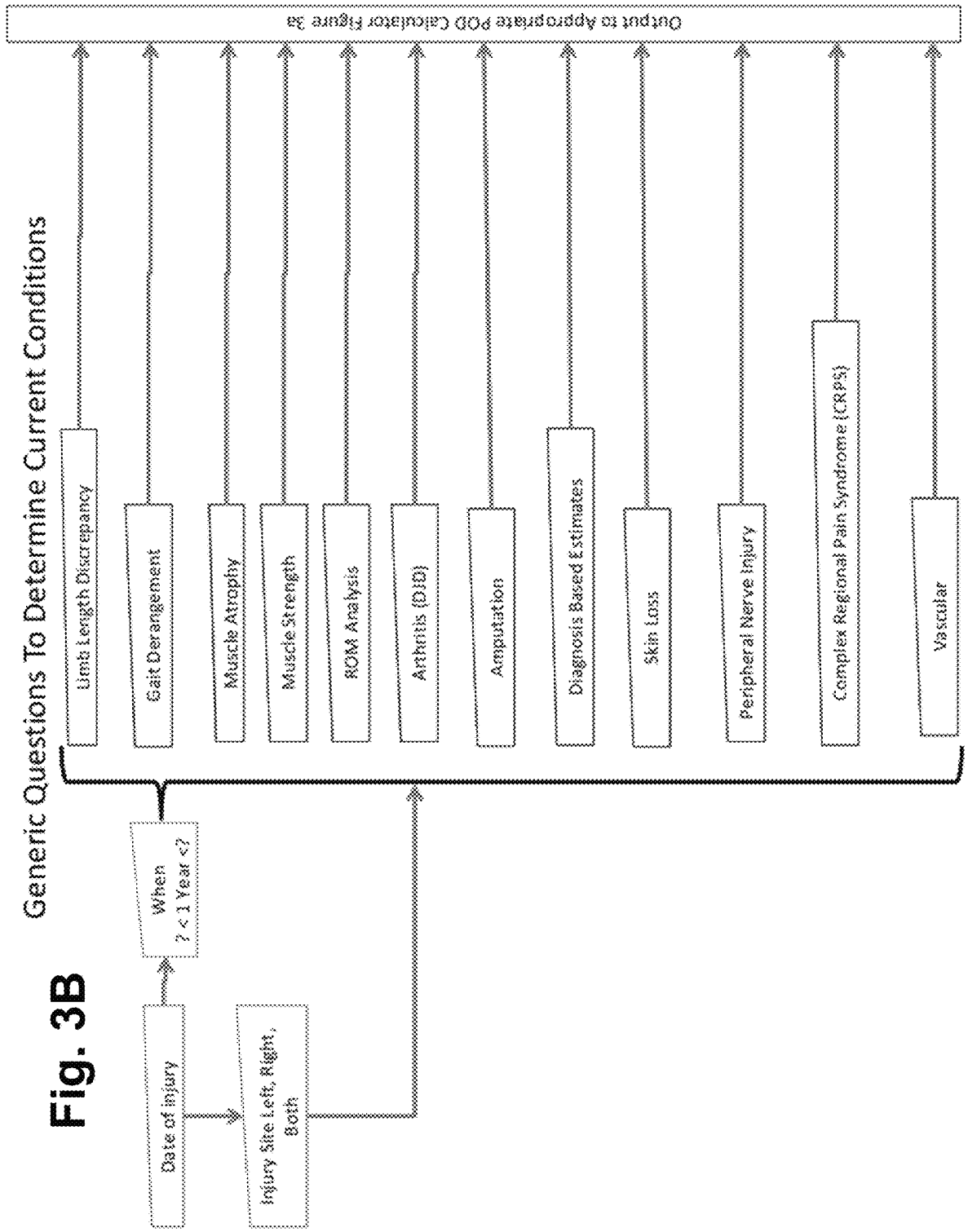

The algorithms involving the lower extremities are found in FIGS. 3A-3C. The outline for the Impairment rating of the lower extremities is outlined in the AMA Guides 5th edition. Specifically, the table of FIG. 3C lists the areas of examination to perform the rating. In these algorithms, the areas of examination and their interaction between lower extremity parts and with the rest of the body are what make up the administrative rule sets. As with the other unique algorithms, these ARS's then provide the workflow in the examination to obtain the data necessary for an accurately characterize the pathology and in turn enable an accurate impairment rating. Much of this determination is dependent on the number of pathologies present in the worker. Frequently there are multiple pathologies present. Having a guide in the clinical setting that can in 'real time' guide the physician through the labyrinth of ARS's to arrive at the correct set of measurements and insure the highest Examiner effort to generate an accurate impairment rating as described within the FIGS. 3A-3C. RateFast provides the user with separate impairment values for each criteria that is evaluated, such as shown in FIG. 3A. Each criteria; limb length discrepancy 301, gait derangement 303, muscle atrophy 305, muscle strength 307, ROM ankylosis 309, arthritis DAD 311, amputation 313, and a diagnosis rating exam (DRE). Combining each impairment rating for each criteria of the lower extremity allows RateFast to correctly calculate an overall impairment rating for the lower extremity.

For Limb Length Discrepancy 301, the ARS workflow algorithm guides the physician to solicit the measurements necessary to obtain a % WPI.

For Gate Derangement 303, the ARS workflow algorithm guides the physician to observe the movements necessary inventory of ambulatory devices to obtain a % WPI.

For Muscle Atrophy 305, the emphasis is the determination of unilateral Leg dimensions, etc to guide the physician to the measurements necessary to obtain a % WPI. A reminder will be present to remind the Examiner that additional conditions (e.g. varicose veins) can invalidate the measurement.

The muscle strength 307 ARS workflow algorithm guides the physician to solicit the strength, resistance measurements necessary to obtain a % WPI. This examination includes: Hip, Knee, Ankle, Big toe % WPI to obtain a Final Manual Muscle Test % WPI.

The ROM ankylosis 309 ARS workflow algorithm guides the physician to solicit the Range of Motion measurements when underlying organic pathology is determined as the cause of impairment to obtain a % WPI. This examination includes: Hip, Knee, Ankle, Hindfoot, Tibia-Os Calsis Angle, Great Toe, Lesser toes. These are then combined to obtain Full Range of Motion % WPI.

For arthritis 311, the ARS workflow algorithm guides the physician to solicit the measurements necessary to obtain a % WPI in the context of potential multilateral presence of different pathologies, including: Sacroiliac, Hip, Knee, Patellofemoral, Ankle. Subtalar, Tolonavicular, Calcaneocuboid, First Metatarsophalangeal, Other Metatarsophalangeal. These are then analyzed, or combined to obtain a "Final Arthritis" % WPI. Specific conditions that include but are not limited to patellofemoral pain can be specifically validated for impairment rating if other areas of the RateFast program document specific conditions such as a direct strike trauma, analyze for a comparison of arthritic rating vs. non arthritic rating and return the higher value.

The amputations 313 ARS workflow algorithm guides the physician to solicit the measurements necessary to obtain a % WPI of different pathologies, including: percent partial WPI for each of: Hemipelvectomy, Hip Disarticulation, Above Knee, Knee Disarticulation, Below the Knee, Syme (Hindfoot), Mid Foot, Transmetartarsal, First Metatarsal, Other Metatarsals, All toes at Metatarsal, Great Toe at MTP joint, Great Toe at Interphalangeal Joint, Lesser Toes at MTP Joint. Then Final determine final % WPI for amputations.

The diagnosis based estimates 315 ARS workflow algorithm guides the physician to solicit the measurements necessary to obtain a % WPI of different pathologies, including: PelvisHip, Femoral Shaft, Knee, Tibial Shaft, Ankle, Hindfoot, Midfoot, Forefoot Deformity. In certain instances which include but are not limited to joint arthroplasty of a hip, additional considerations of the CDS such as an extended ADL review of hip activities are used to further validate the rating as required by the ARS. Then a Final DBE % WPI is calculated.

The skin loss 317 Algorithm guides the physician to solicit the measurements necessary to obtain a % WPI of different pathologies, including: Isheal, Tibial Tuberoscity, Heel Plantar Surface/Metatarsal Head, Chronic Osteomyelitis (Active Drainage), dressing demands and alteration in footwear. This data is then used to obtain a Final Skin Loss % WPI.

For peripheral nerve injuries 319, the ARS workflow algorithm guides the physician to solicit the measurements necessary to obtain a % WPI in the context of potential multilateral presence of different pathologies. Including: Motor Injuries: Femoral, Obturator, Superior Gluteal, Inferior Gluteal, Sciatic, Common Peroneal, Medial Plantar, Lateral Plantar. Final Motor % WPI Sensory injuries: Femoral, Lateral Femoral Cutaneous, Sciatic, Superior Gluteal, Sural, Common Peroneal, Superficial Peroneal, Medial Plantar, Lateral Plantar. Then they are combined (Final Motor and Sensory) to obtain a Peripheral Nerve % WPI.

The ARS workflow algorithm for complex regional pain syndrome and causalgia (RPS) 321 guides the physician to solicit the examinee information necessary to obtain a % WPI in the context of potential multilateral presence of different pathologies with or without the pain. This then leads to the calculation of RPS to the % WPI.

The vascular disorder 323 ARS workflow algorithm guides the physician to solicit the measurements necessary to obtain a % WPI of potential multilateral presence of different pathologies. This then leads to the calculation of vascular disorders to % WPI.

To obtain a final lower extremity % WPI results from the analysis of the LEI's and the other lower extremity body part regions. A calculation is made for a unilateral or bilateral injury if applicable and reported. FIG. 3C shows the lower extremity impairment rating elements in combination for the ARS workflow.

Spine

Figure 4A:
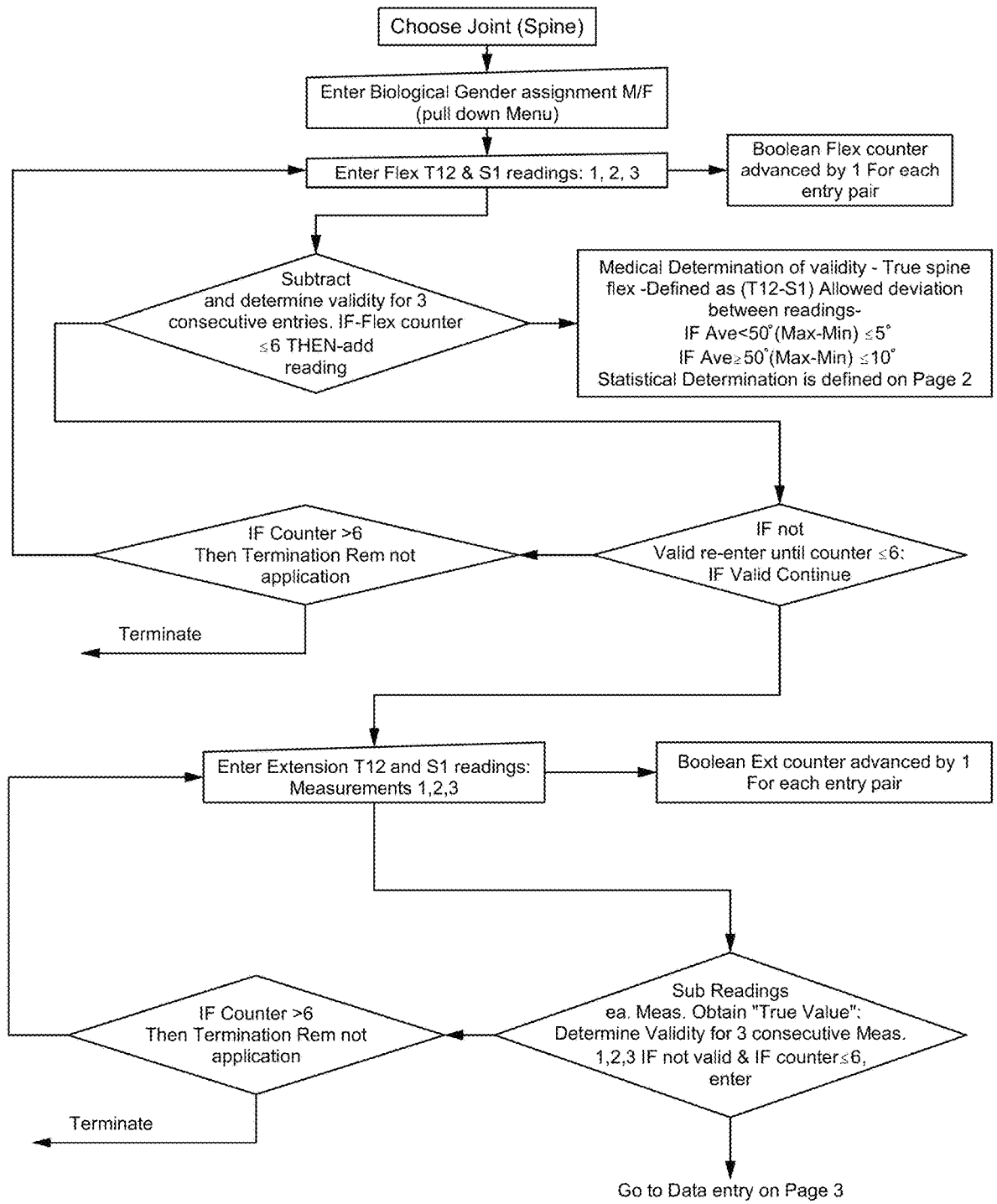
FIGS. 4A-4C illustrate spine impairment algorithms in accordance with some embodiments.
Figure 4B:
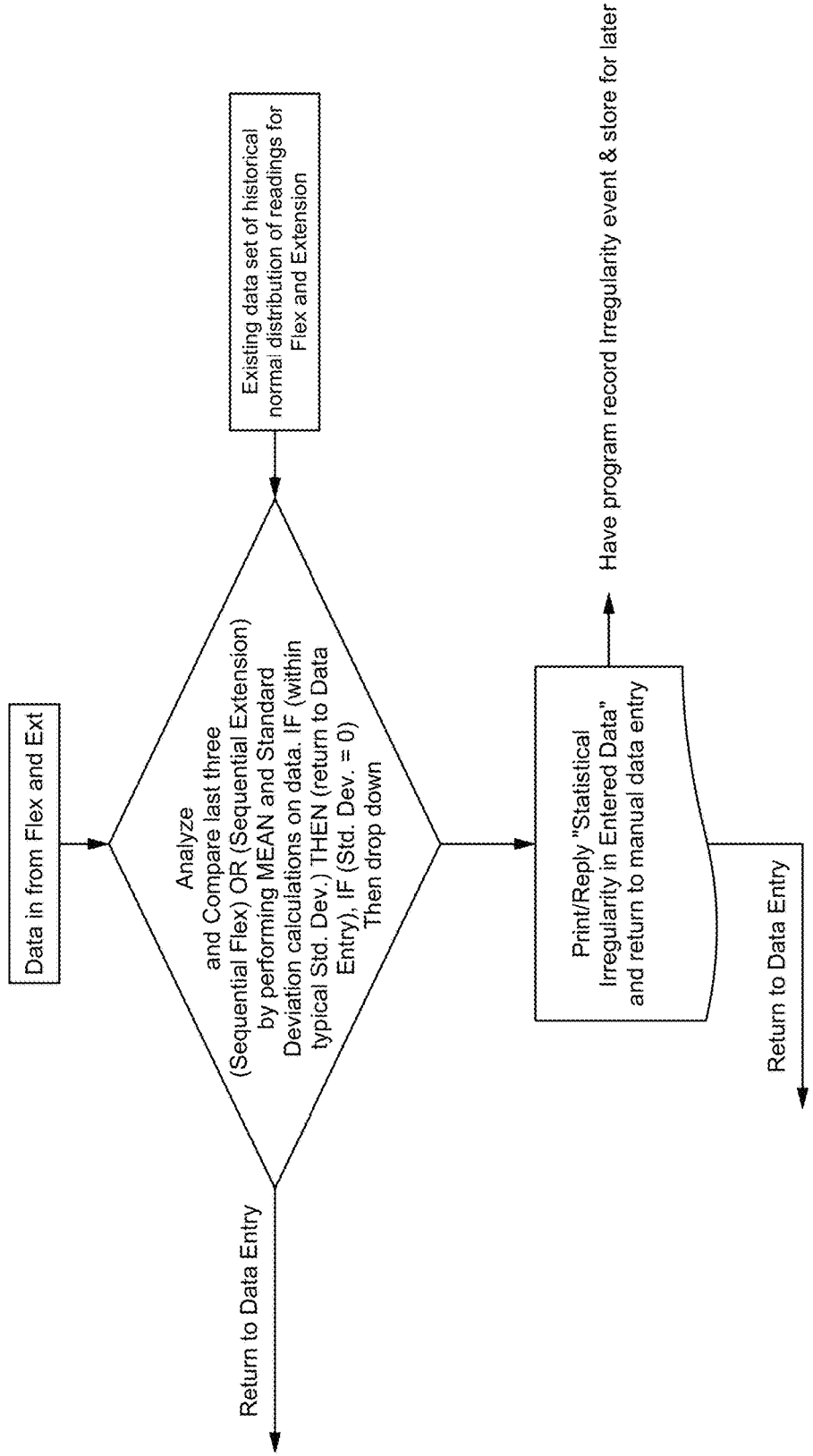
Figure 4C:
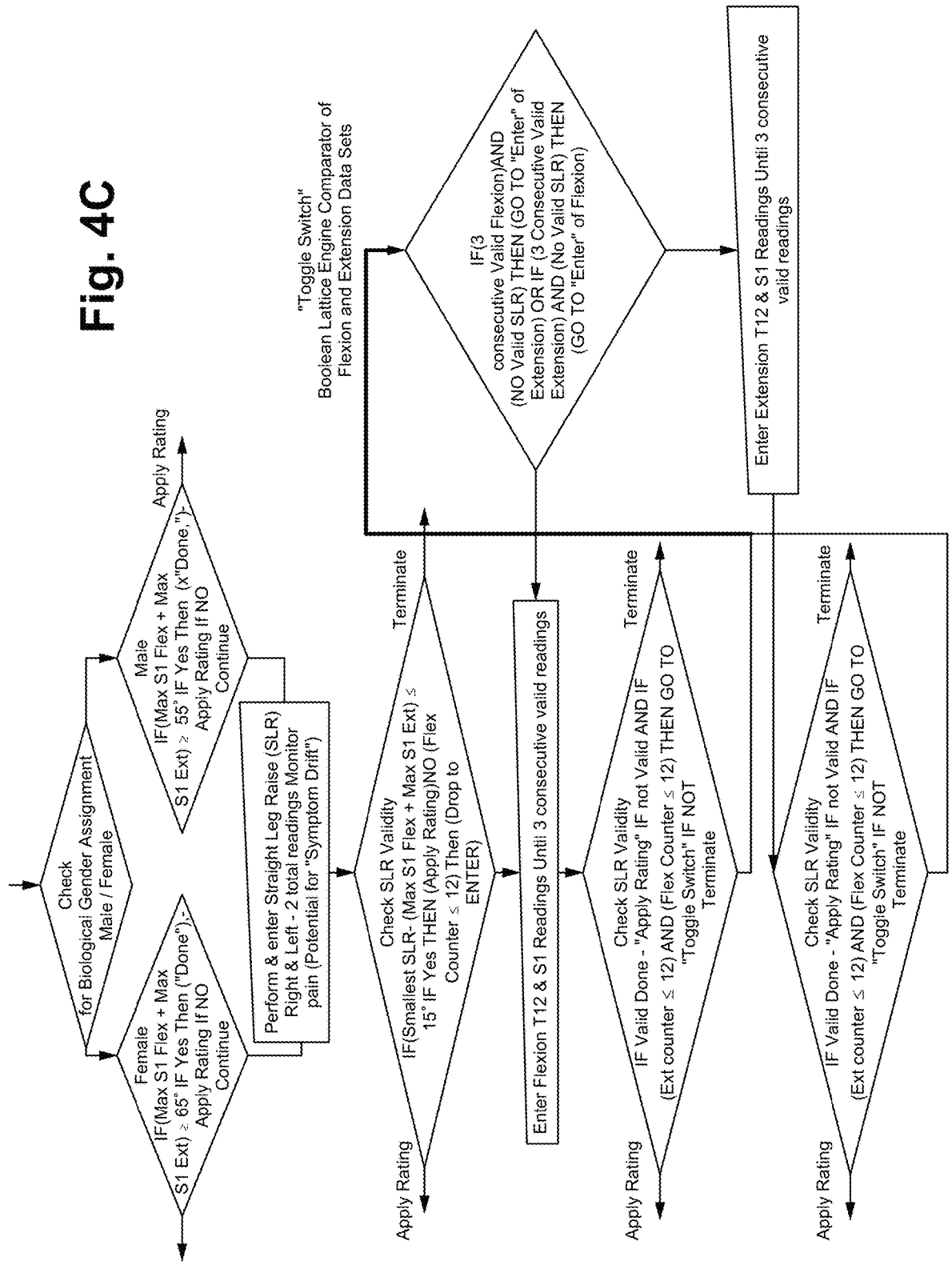

The algorithms involving the spine are found in FIGS. 4A-4C. It is first determined if the diagnosis rating exam (DRE) or range of motion (ROM) can be used to obtain an impairment rating. This first protocol or administrative rule set of DRE versus ROM needs to be ascertained to determine which clinical approach is appropriate in order to select the correct subset of ARS's or algorithms that are to be used in the rating process. A primary evaluation is made to determine which method is to be used to examine the spine segments. If there is fusion or injury of two or more segments, the ROM method must be used. If NOT then there are still options of DRE or ROM (shown in FIG. 9) and further explained below. In either case the calculators will out put a % WPI for each method.

The options path, displayed in FIG. 9, provides an evaluation of the "conditions represented" for each method. These conditions can include: spasm, radiculopathy, motion, herniated disc, fracture, surgical event, arthrodesis, alteration segment integrity, and degenerative joint changes.

As shown within FIG. 9, 1) the method with the highest "represented condition" number wins!=>Find % WPI, 2) If there is a tie of (same #) "conditions represented", then highest WPI is awarded as winner method and % WPI, 3) if there is a tie and (both=) conditions represented and % WPI then answer is "DRE and ROM methods are equivalent" output WPI %=

Referring now to FIG. 4A, the clinical algorithm for ROM first asks for spine flex data in sets of 3 consecutive readings. This data is then statistically analyzed for validity of the data by determining the variance of the input readings. The validation for the specific spinal regions (e.g. cervical, thoracic and lumbar) vary in the definitions which adds to additional confusion and calculation burden to remain compliant with the ARS. For example, the lumbar spine average is used to determine if the variance tolerance is 5 D or 10D using a 50D result as the decision. cervical spine validation is not based on a split variance, but rather must be validated within a fixed difference of degrees OR 10%, whichever is greater. Finally, a thoracic spine rating is validated from the mean of the three measurements using a 5D tolerance or 10% variance, whichever is greater.

An administrative rule set is applied based on the size of the base value and application of statistics, to arrive at a bounded variance specific to the body part under analysis. This provides a more reproducible result and is a fairer and balanced approach to rating the specific motion range.

As further described below, the input readings are also 'real time' analyzed for data that is too singular (same number). This special situation is one that might indicate the data is being fabricated without actual measurement. The statistical analysis will recognize this situation and output a message indication the potential for an "anomaly" in the data. Requesting the clinician to re-check the data.

The method also applies Boolean operators in counting the number of data entry attempts for the purpose of bounding the number of acceptable operations before the rating process is halted. The source of the rejection of the data, described above, can be due to excessive variance or lack of variance in the data. This application of the Boolean operation takes place a set number of times based on a statistical student's t-algorithm of 95% confidence in the data. In this particular application of the spine analysis a set of 3 readings is considered 1 data set. The analysis requires n+3 (=4) to achieve 95% confidence in the data. The result is a possible of 12 total readings (3*4).

Bounding is unique and useful in the data acquisition process. Algorithm monitoring of the frequency of acceptance and rejection provides an iterative or adaptive adjustment of the statistical bounding over time. This further defines expected variance and assist in reducing the inherent error in the impairment rating process.

In some embodiments, the impairment rating process algorithm can identify malingering on the part of the examinee. The anticipation of inherent variance and bounding the variance and number of trials are set specifically by statistical rules to attain a 95+% accurate rating. Examinee embellishment, self medication, stoic (pain) tolerance, are examples of factors enabling inappropriately adjusted or shifted range of motion values leading to a rating not accurately reflecting the actual impairment.

Another special cause is the Examiner prematurely concluding the test and data acquisition, prior to possessing sufficient data to attain 95% confidence. This might be due to time constraints, lack of diligence, or collusion with the examinee. The specific ARS has within it logic specific to detect this types of impairment rating error.

For example, the RateFast method can employ a "toggle switch" in the data acquisition process which cycles back and forth between flexure and extension measurements of spinal mobility. This algorithm uniquely incorporates the validity of the single leg raise (SLR) with the flexion and extension measurements. The purpose is to provide statistical rigor to the data acquisition process to attain a 95% confidence in the accuracy of the impairment rating while introducing efficiency in the data collection process.

In some embodiments, the RateFast method adjusts for clinical variance and/or experience. For example, the difference in the anticipated flex of the Lumbar portion at 10% while the Thoracic is equal to or Less than 5%. This is felt to be an arbitrary expected value, with substantial base value difference, not based on historical data set (see discussion above on ROM motion validation).

As described above, the method enables every examinee to have equal worth and opportunity to demonstrate his/her permanent impairment.

Skin Section

Figure 5:
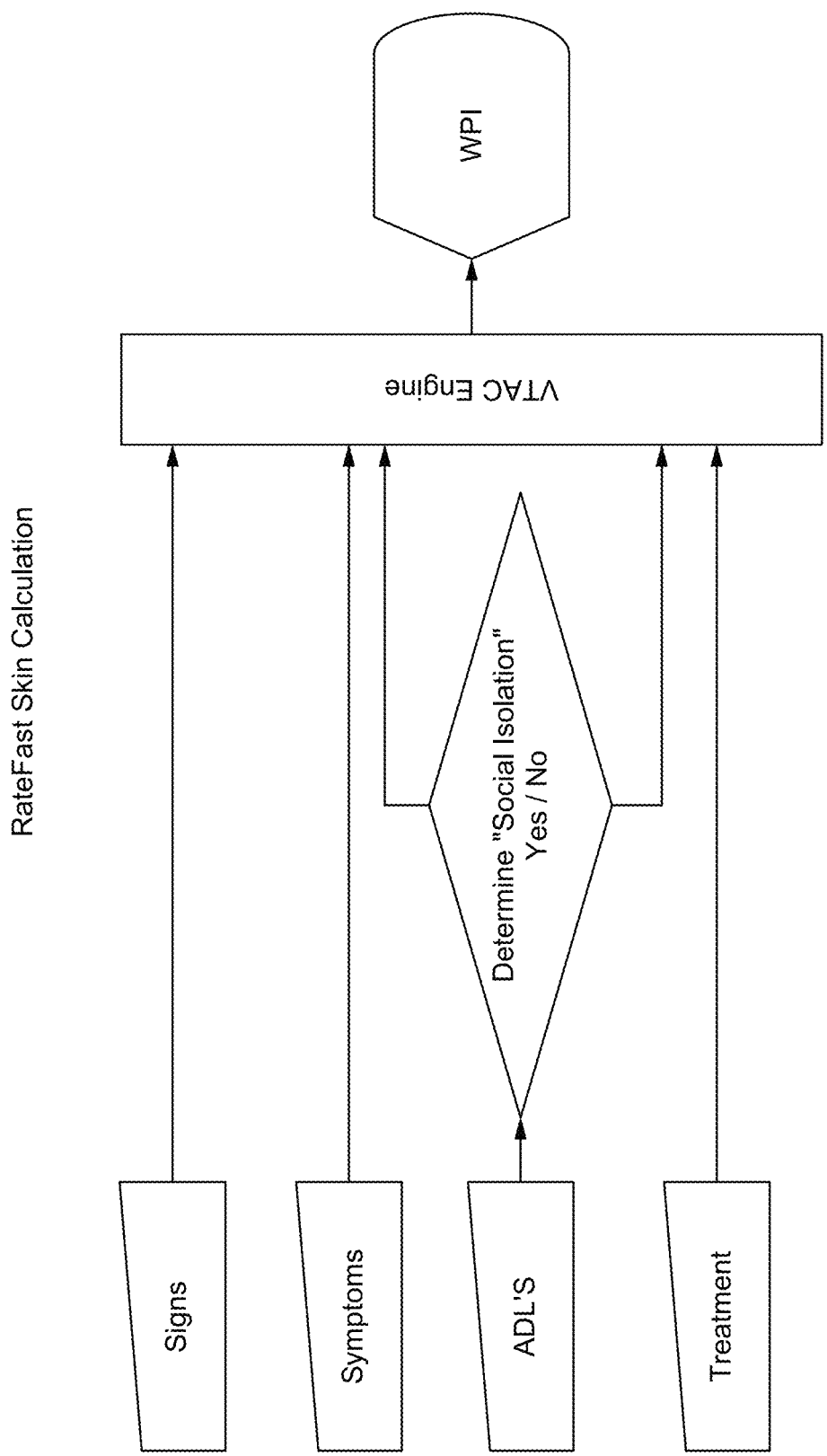
FIG. 5 illustrates skin impairment calculations in accordance with some embodiments.

FIG. 5 illustrates the process of calculating a skin impairment rating. Skin permanent impairment rating poses a special challenge for standardization of data collection, as it is exclusively driven by activities of daily living for impairment rating classification, and spans a tremendous range of impairment from 0% to 95% WPI over the course of five rating classes (1-5).

Current inventions have no activities of daily living inventory to assign weighted values to assist the Examiner in the selection of classification. RateFast includes a weighted activity of daily living inventory algorithm which objectively assigns the primary 1-5 rating class, and additionally prompts social factors to delineate between classes 4 and 5 specifically.

Skin permanent impairment can include a consideration of two additional influential factors in the adjustment of the impairment rating class assigned, which includes the signs and symptoms of the condition both be present, and the consideration of the treatment burden. Current implementations do not provide bounded definitions for critical rating terminology such as "few", "some", "many" and "most". RateFast provides an aggregation of the CDS and RDS to perform this determination for the user.

Variable Thread Analytic Computation (VTAC)

Figure 6:
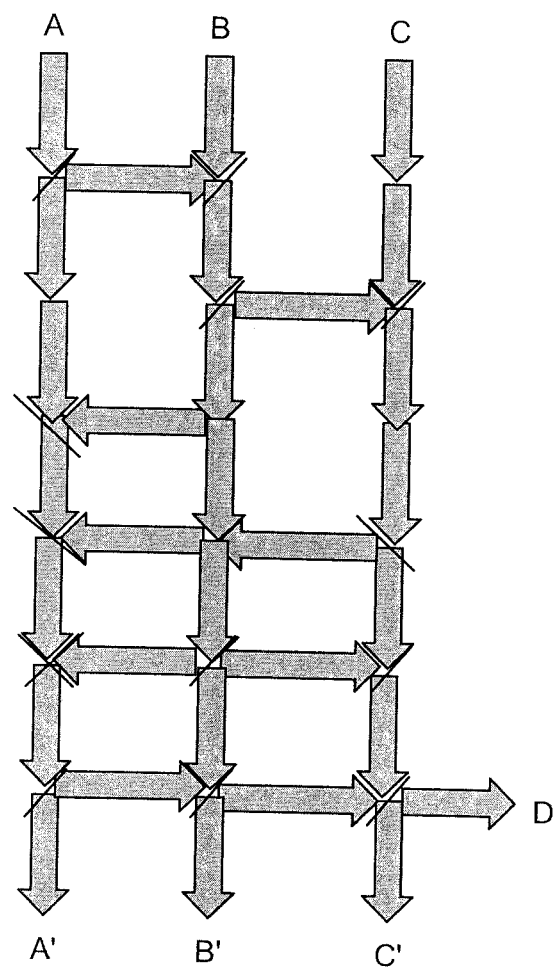
FIG. 6 illustrates a variable thread analytic computation (VTAC) concept in accordance with some embodiments.

As shown within FIG. 6, VTAC comprises a unique algorithm enabling a multiplicity of Administrative Rule Sets (ARS) or body parts, to be simultaneously involved in the impairment rating process. VTAC comprises of elements of Boolean and fuzzy mathematic functions. FIG. 6 is a representation of, but not limited to, the potential interaction matrix that can be involved in an impairment rating of an individual.

FIG. 6 is a representative flow chart where the vertical lines of A, B, C are representative of, but not limited to, ARS, body systems, or body parts. Each of these input sources are comprised of a data sets. The interaction of the vertical lines indicates the interaction of the input sources affecting one another. For example, this can represent one body part affecting another such as a primary injury causing a derivative or secondary injury and the impairment rating process. Additionally a single body part versus a two or more involved body parts in an injury can influence the outcome of "grouped logic data sets" to realize the highest impairment value provided by the ARS.

A calculator engine that contains the ARS can undergo specific and simultaneous calculations. This also includes logic for missing or incomplete data entry requests to account for the final result and assures the validity of the dependent data.

MMI Calculator Discovery Tool

Figure 7:
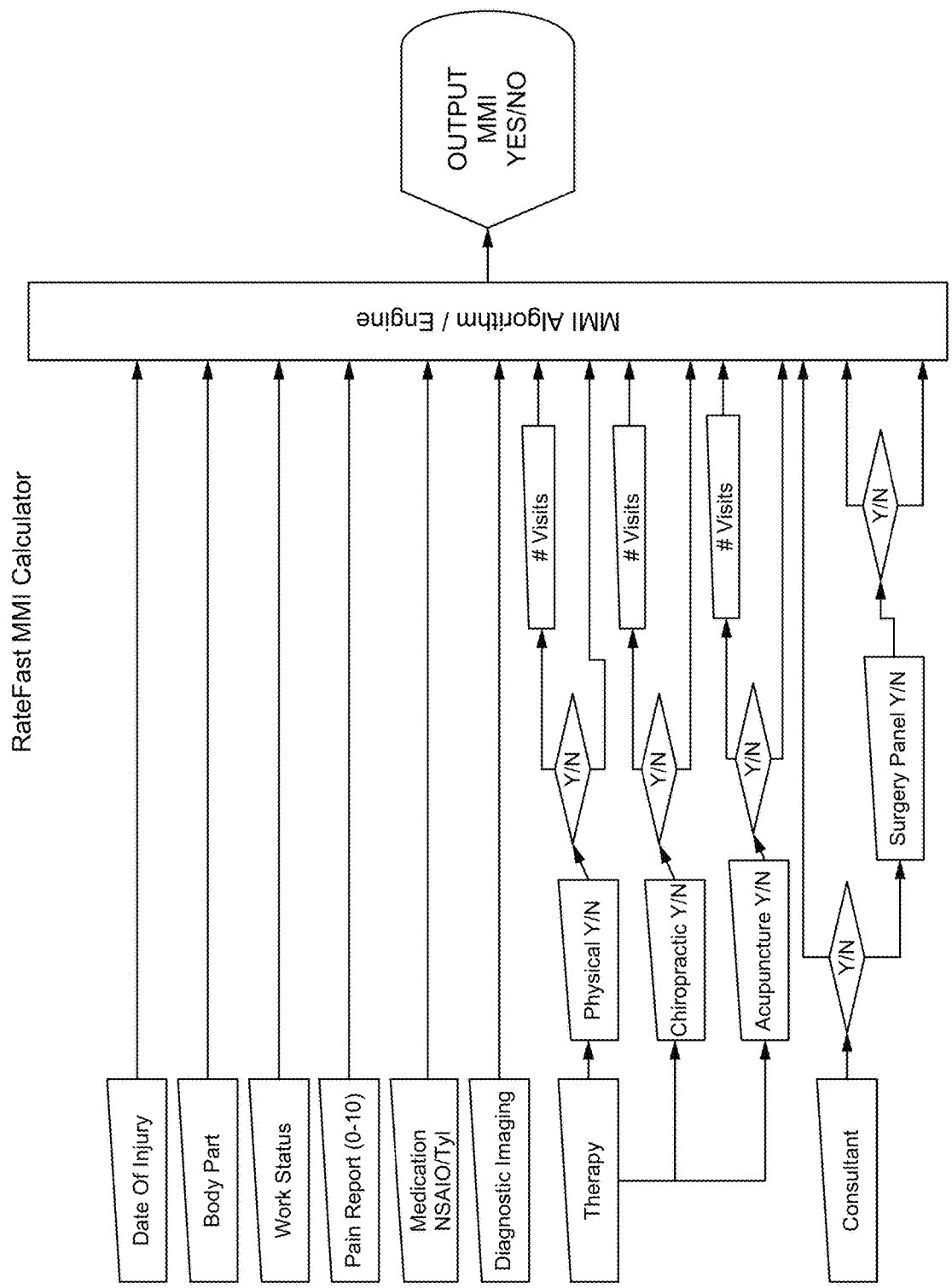
FIG. 7 illustrates one or more maximum medical improvement (MMI) calculator in accordance with some embodiments.
Figure 8A:
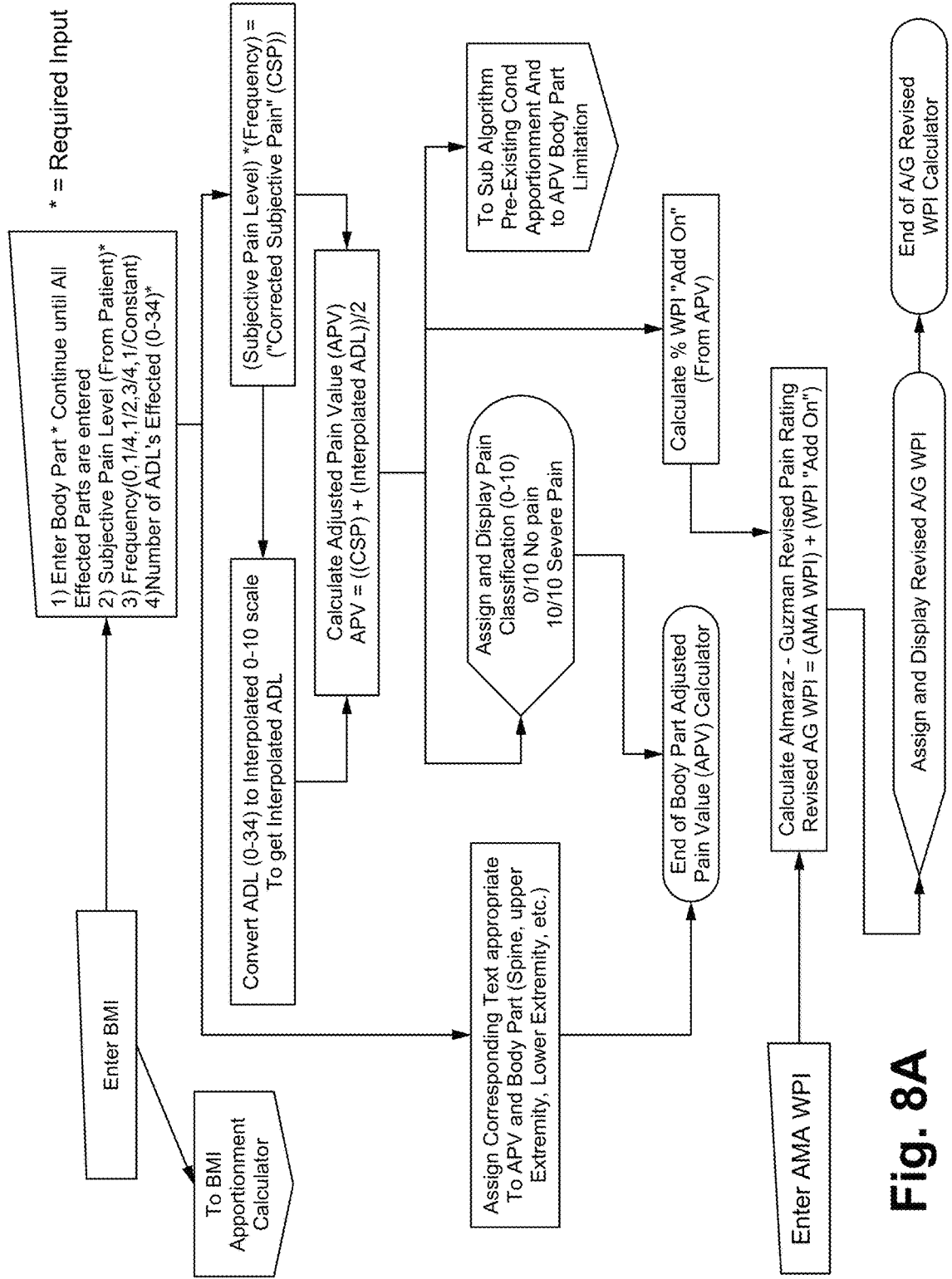
FIGS. 8A-8F illustrate an Almaraz-Guzman flow chart in accordance with some embodiments.
Figure 8B:
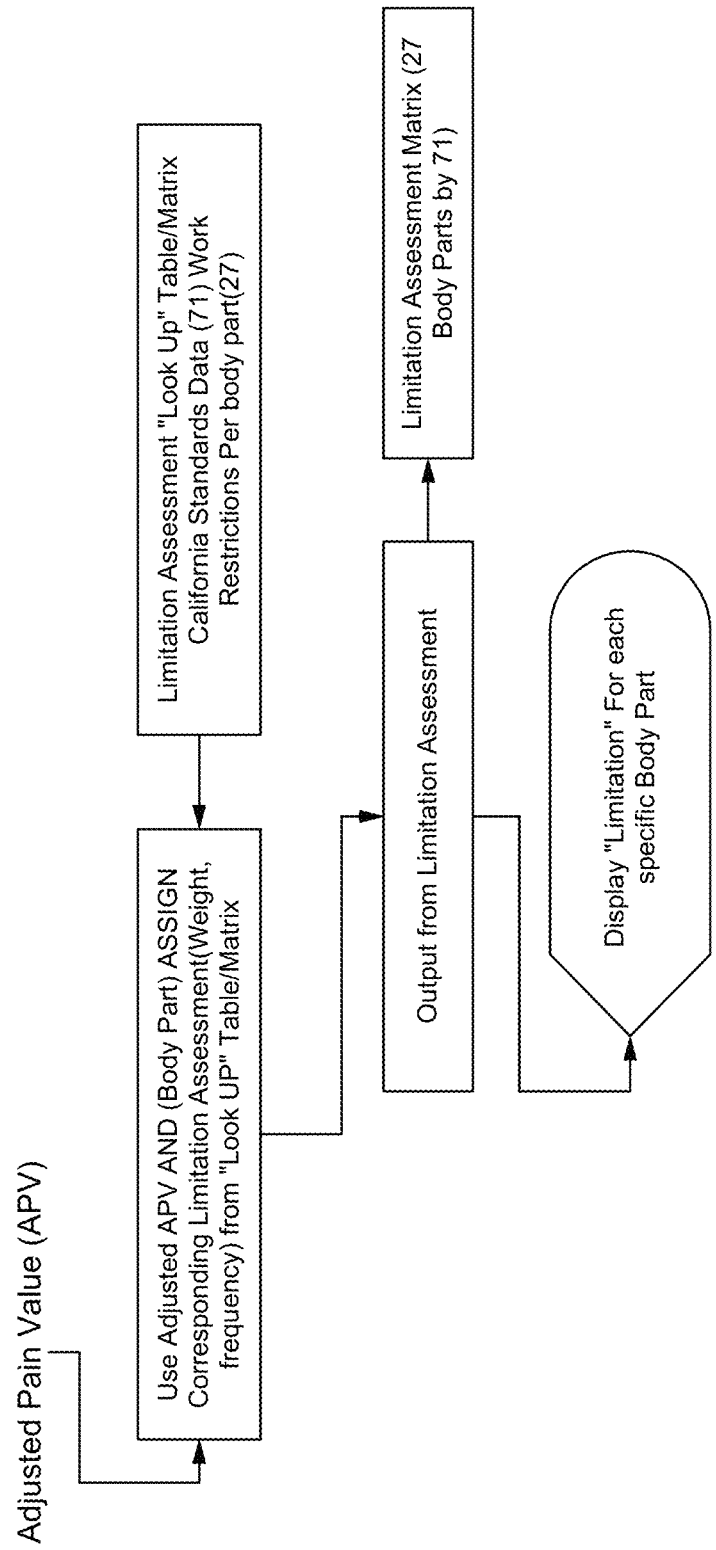
Figure 8C:
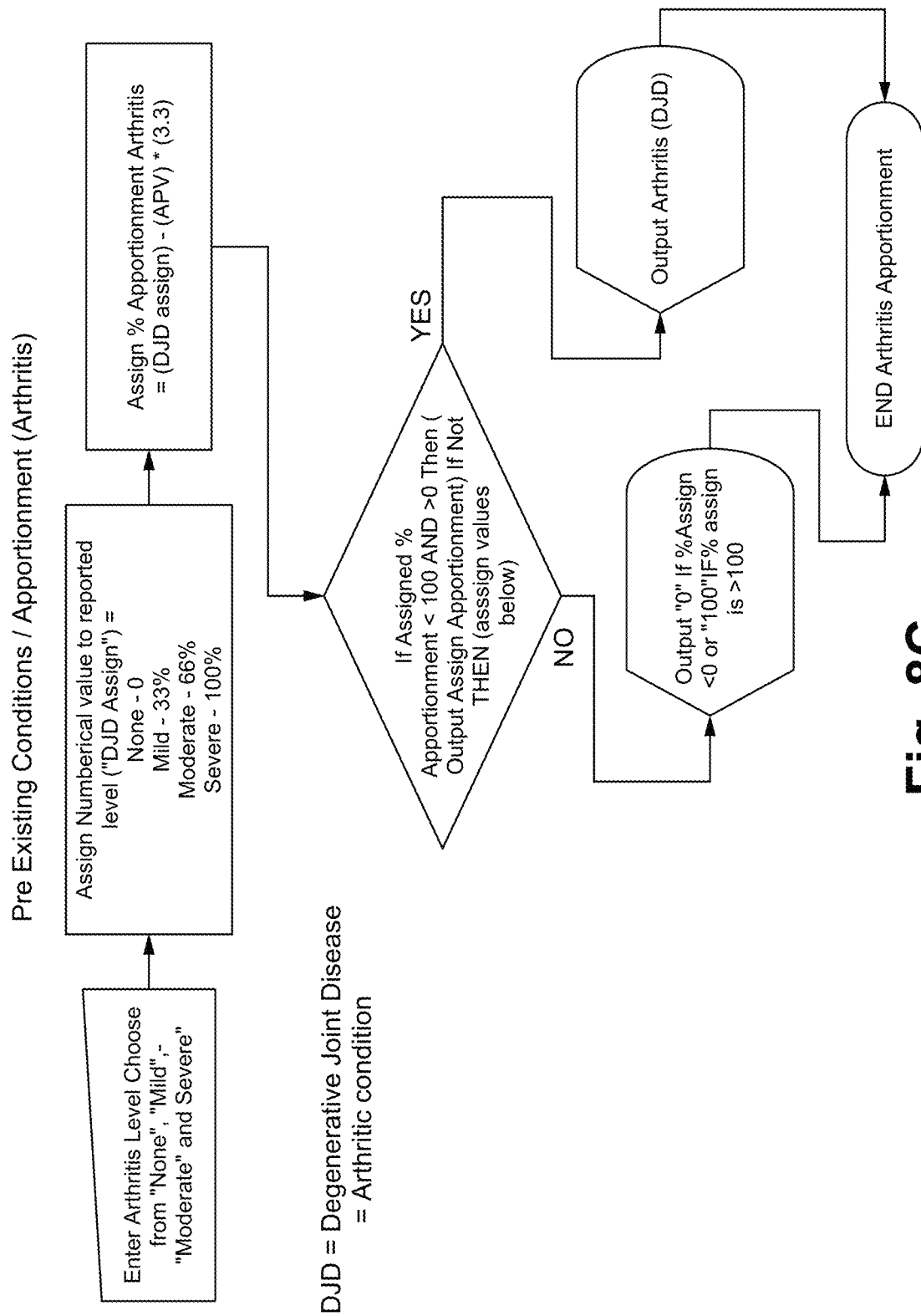
Figure 8D:
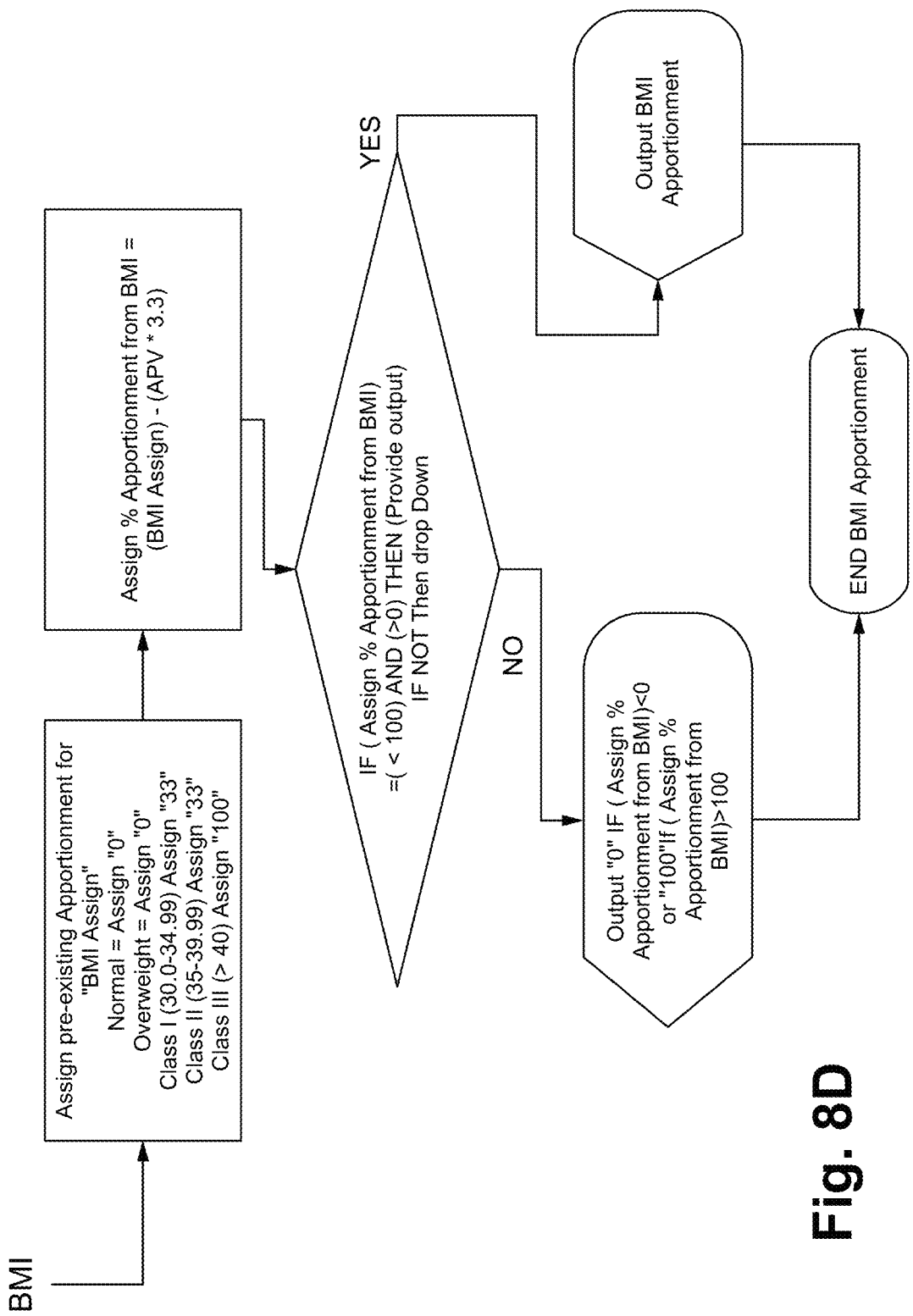
Figure 8E:
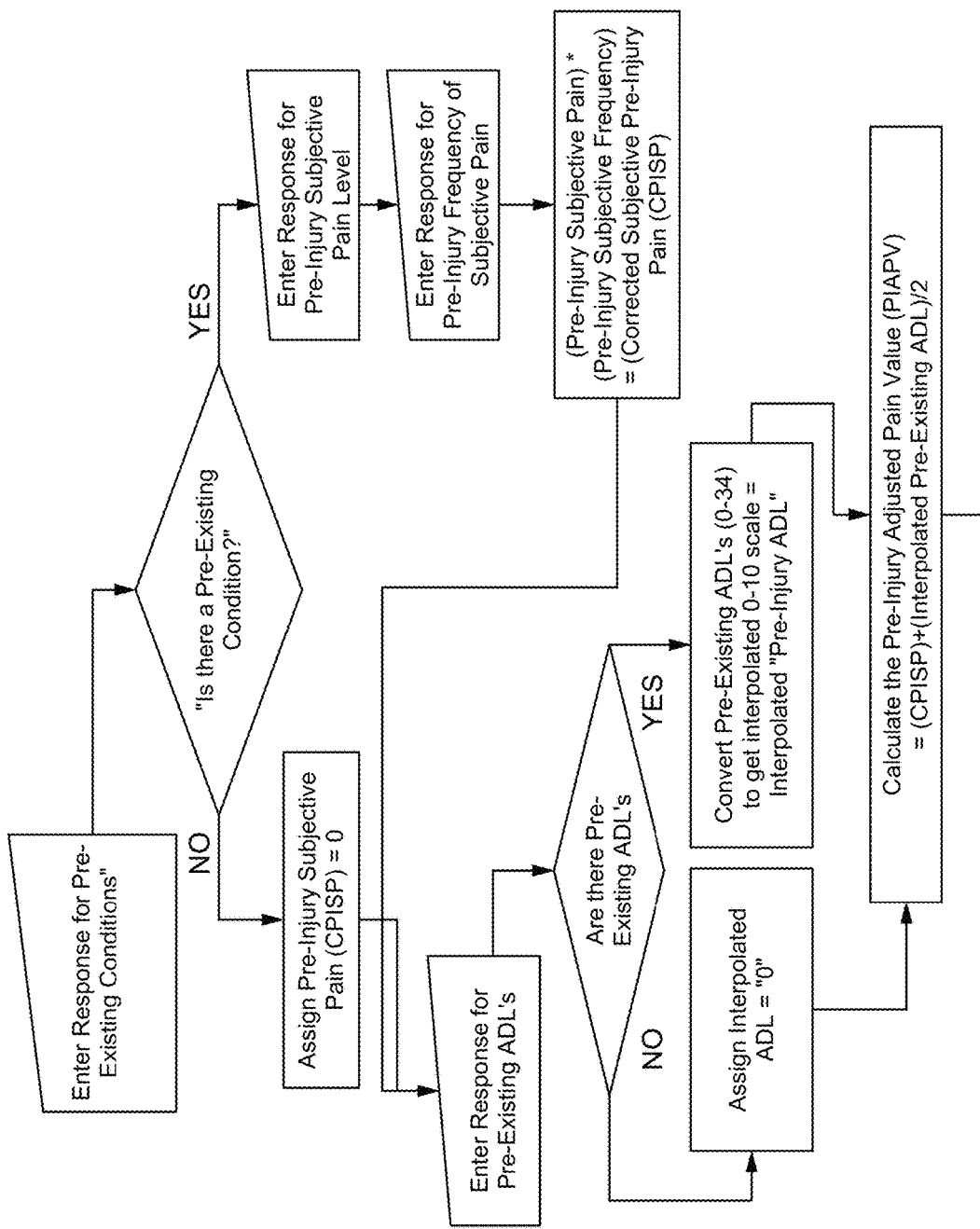
Figure 8F:
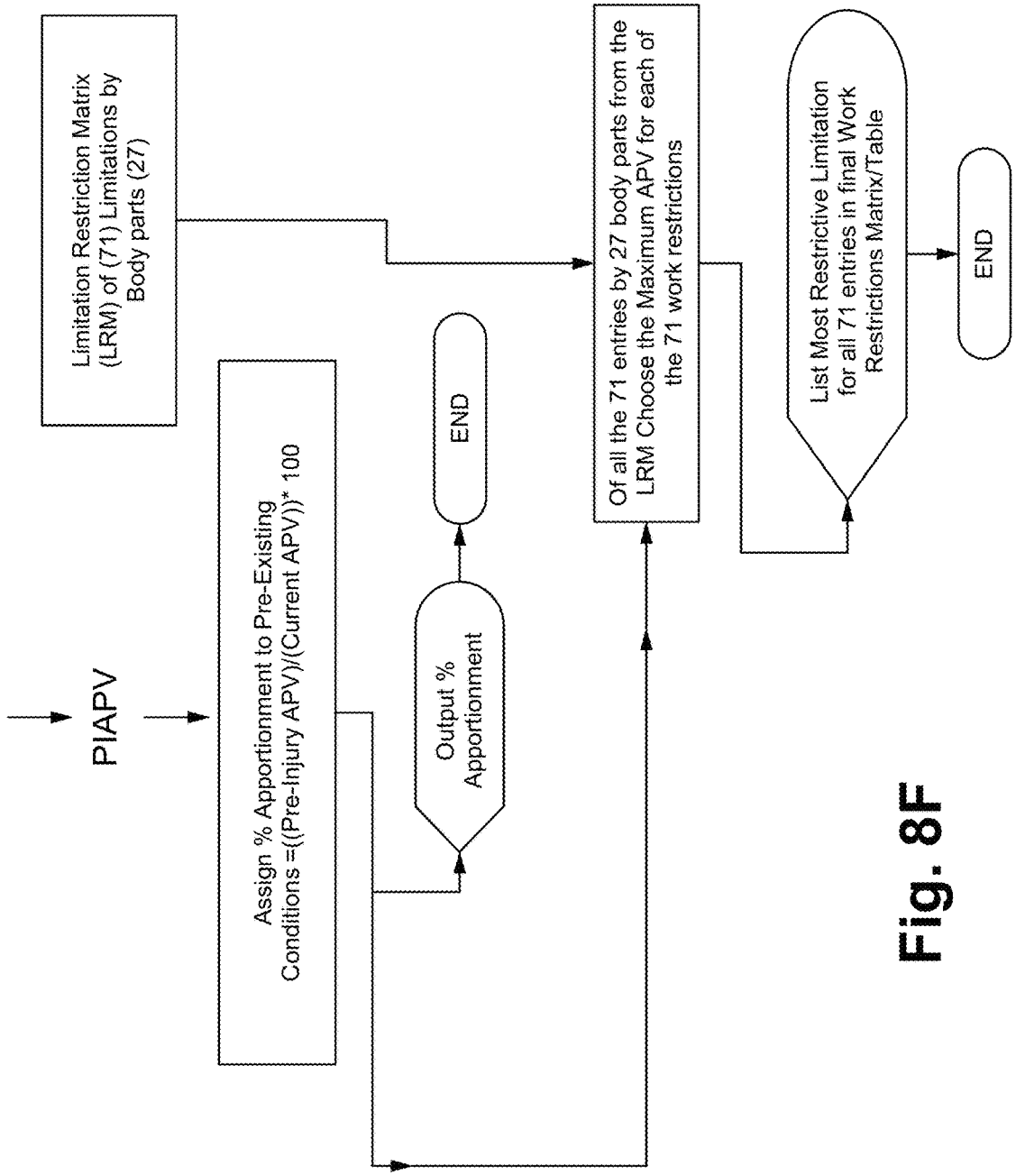

FIG. 7 illustrates an algorithm used to determine if an injured worker has met the ARS definitions for MMI. This is a combination of time and medical treatment attempts for reaching milestones in claim treatment (e.g. is the recovery process still ongoing for the diagnosed pathology or condition or not ((e.g. MMI definition has been met)) or has ARS mandated treatment guidelines that are beneficial and which must be exercised or available by a stakeholder. For example, HIPPA compliant data to determine a MMI status. An example of this is the California workers' compensation adoption of the Medical Treatment Utilization Schedule for purposes of outlining consistent understanding of treatment recommendations across stakeholders.

An example of data entry parts, can be but is not limited to: date of injury (DOI), body part(s), work status, pain report, medication trials, diagnostic data, therapy intervention, advanced imaging, consultant evaluation and determination of intervention to be made available or considered.

Pain (Almaraz Guzman, Cannon Algorithms)

The algorithms as shown within FIGS. 8A-8D arose from the California case rulings of Mario Almaraz and Joyce Guzman. Together these worker compensation cases and rulings, albeit legally separate, are known as the "Almaraz-Guzman" (AG) Cases. The commonality of these California landmark cases is the impairment rating that the physician used to rebut the rating resulting from strict adherence to the "AMA Guides". The reasons for deviation from the AMA Guides were that some medical conditions are not adequately described by conventional impairment rating methods. The California Workers Compensation Appeals Board provided guidance for a physician to provide evidence that might be considered to rebut the rating emanating from strict adherence to the AMA Guides. The board's ruling defined the so called "four corners" as the physician's judgment, training, experience and skill in the performance of the impairment rating. This further imposes a burden on the rating physician to clearly document the reasons for departing from the AMA Guides.

Currently, there are no readily identified clinical data set (CDS) elements that allow the user to consistently apply the AG consideration.

RateFast applies algorithms and identifies the user in response to these additional legal requirements of the impairment process which supports the opinion of the adjustment, or lack there of, to the impairment rating.

Cannon vs. City of Sacramento

In another ruling, an impairment rating was allowed that deviated from adherence to the AMA Guides. This judicial ruling which enables a "Whole Person Impairment" (WPI) rating at the discretion of the physician when there is absence of a ratable medical condition (e.g. 0% WPI) yet the medical condition affects the individual. The RateFast software applies an algorithm and identify this CDS configuration and assign a corrected rating, in addition to having this value subjected to AG as required.

Comparison of Two Methods (ROM and DRE/DBE)

As described above, the options path, displayed in FIG. 9, provides an evaluation of the "conditions represented" for each method ROM and DRE/DBE. The use of these impairment evaluation methods is described and used in the structural body systems such as; upper extremities, lower extremities and spine.

The ROM method is thought to be a purely objective data set that evolves from physical measurement of the mobility range of the body part under examination. DRE or DBE stand for "Diagnosis Related Estimate" or "Diagnosis Based Estimates". This evaluation method relies principally on the physician's judgment, training, experience and skill to arrive at a diagnosed impairment rating.

According to the AMA Guide, a user is instructed to use the ROM method " . . . when an individual's condition is not well represented by a DRE category." However, in Section 15.2 the DRE method is clearly pointed out as "the principle methodology used to evaluate an individual who has a distinct injury". These two comments are directly in conflict with one another, and creates confusion for the user, who is left to him/herself to interpret the way forward.

The two methods contain elements of each other. RateFast specifically provides objective discipline to the ROM methods. Consequently, the methods can be truly compared as different methods by quantifying the concept "well represented" using definitions provided within the ARS.

Comparing the DRE and the ROM logic allows a fairer, more accurate, reproducible and more complete analysis of the claimed medical conditions by using specific input analysis of digitized data for the spine including subjective complaints, functional measurements, static measurements, and diagnostic testing. As a result, each method (DRE and ROM) are simultaneously considered, compared, rated for WPI. Consequently, a determination is possible for first, the most accurate rating method representation, followed by a selection of the highest WPI value if both conditions are equally represented by the data.

The subjective and objective information elicits contrasting information to achieve an impairment rating that accurately reflects the existing pathologies. There are two elements to arriving at a complete and accurate data set. The examinee likely does not know what they need to be communicating to the physician. The physician can not know what or how to get the complete set of information from the examinee. Consequently, the examinee needs to be guided in the clinical setting to provide the Examiner the location, impact of the injuries and the ability to perform various functions. The physician, depending on the injuries and pathologies needs to know what and how to guide the examinee to provide the information. Each examinees injuries and pathologies can be different as no two persons are completely alike. This alone makes the DRE method a challenge to arrive at an accurate representation of the examinee situation.

The level of accuracy achieve in addition to the application of the Boolean, statistical methods to elicit, record, and perform functions on the data. This is due to the 'having' a more objective data set, to compare to, with which to contrast the impairment rating and elicit the differences. Having information enables the physician to apply judgment on the ROM and DRE ratings to obtain that improved accuracy impairment rating.

An added benefit to the ROM and DRE comparison is the transparency of the process because both output ratings are provided. This enables a third party reviewer to verify the completeness of the data and objective findings, as well as the output ratings.

Further, this comparison also enables a validity check on each methods approach to evaluate a pathology. Systematic difference can then be used to make adjustments in either the diagnosis (subjective) portions or to the ROM (objective) methods via adjustment of the administrative data sets ARS's or the VTAC logic being applied to obtain the rating.

Section 9: Methods to Assist Data Integrity in the Impairment Rating Process

In another aspect, a collection of methods can be used to perform a multifaceted statistical treatment of new Range Of Motion (ROM) measurements to assess their similarity to existing ROM data sets. Ultimately, this is done to identify those measurements that are suspicious because they deviate significantly from what is expected by the statistical model of the data, or Probability Density Function (PDF), and/or other numerical properties or that they display a pattern inconsistent with expected variation within the expected value range. Two processes are described below.

The Statistical Models/Probability Density Functions

Figure 11:
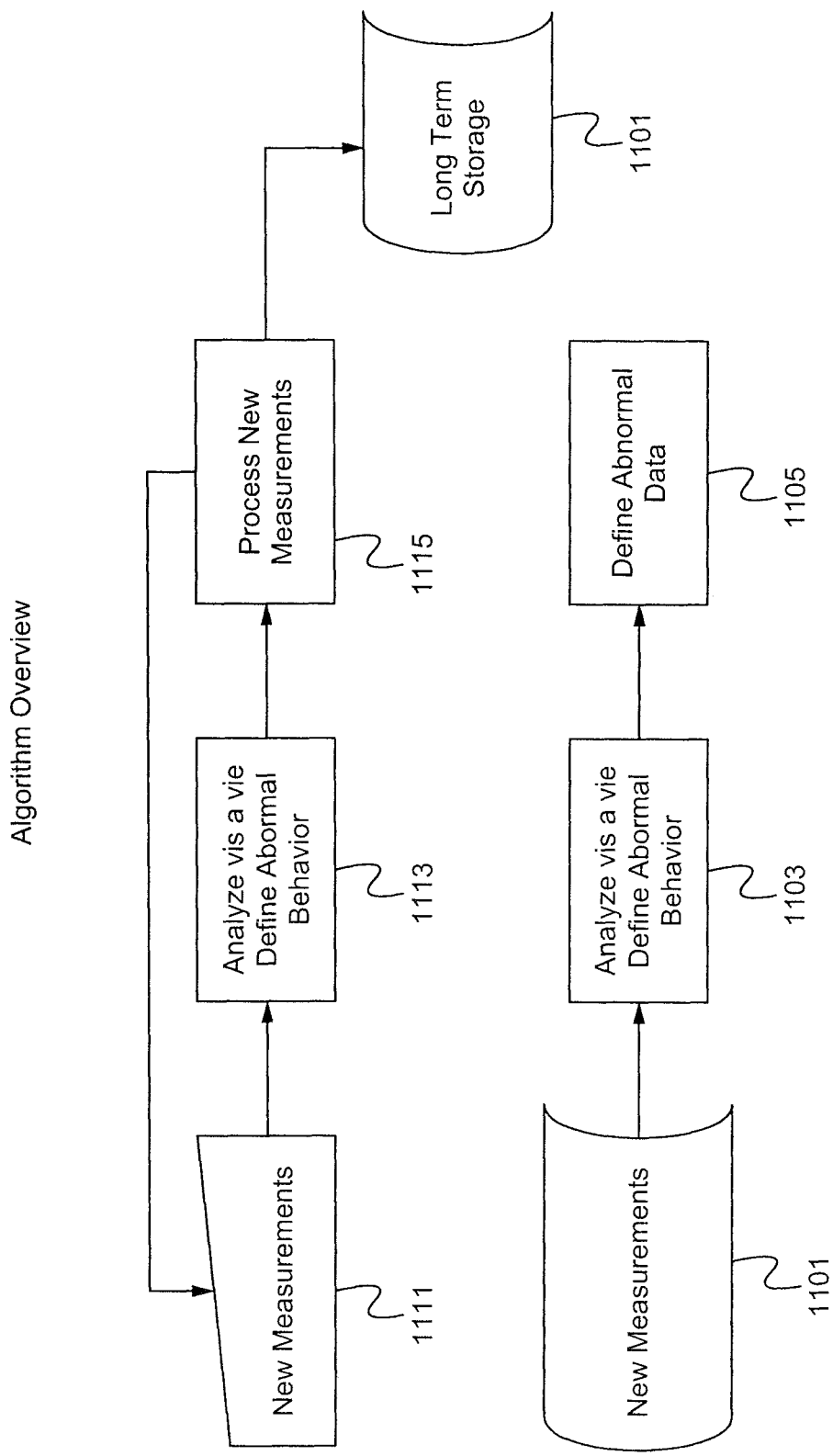
FIG. 11 illustrates the general architecture for determining abnormal behavior within the impairment rating process in accordance with some embodiments.

FIG. 11 depicts the general architecture of this process. The judgment of these abnormalities, whether because of purposeful fraud, a mistake on behalf of an Examiner or just natural aberration in the data, is left to auditing entities. These actions are performed at the time of evaluation to ensure subsequent steps in impairment rating for Workers Compensation claims process valid measurements.

As shown within FIG. 11, a base set 1101 can be used to create a characteristic profile 1103, which can be used to define abnormal data 1105. The base set 1101 can also be used to analyze the new measurements 1111 to define/analyze the abnormal behavior and/or outlier data 1113. The new measurements 1115 can also be processed such as described above and placed in shortage 1120.

The basis of statistical analysis lies in pre-existing knowledge of the data in consideration. Without such knowledge, conclusions drawn are likely to be erroneous. For example, in the field of outlier identification, data points that appear incongruous can in fact be in agreement with an underlying behavior unknown to the researcher, or vice versa. Characterizing the data with the RateFast method provides a data set whose entries form a template for other data to follow.

Figure 14A:
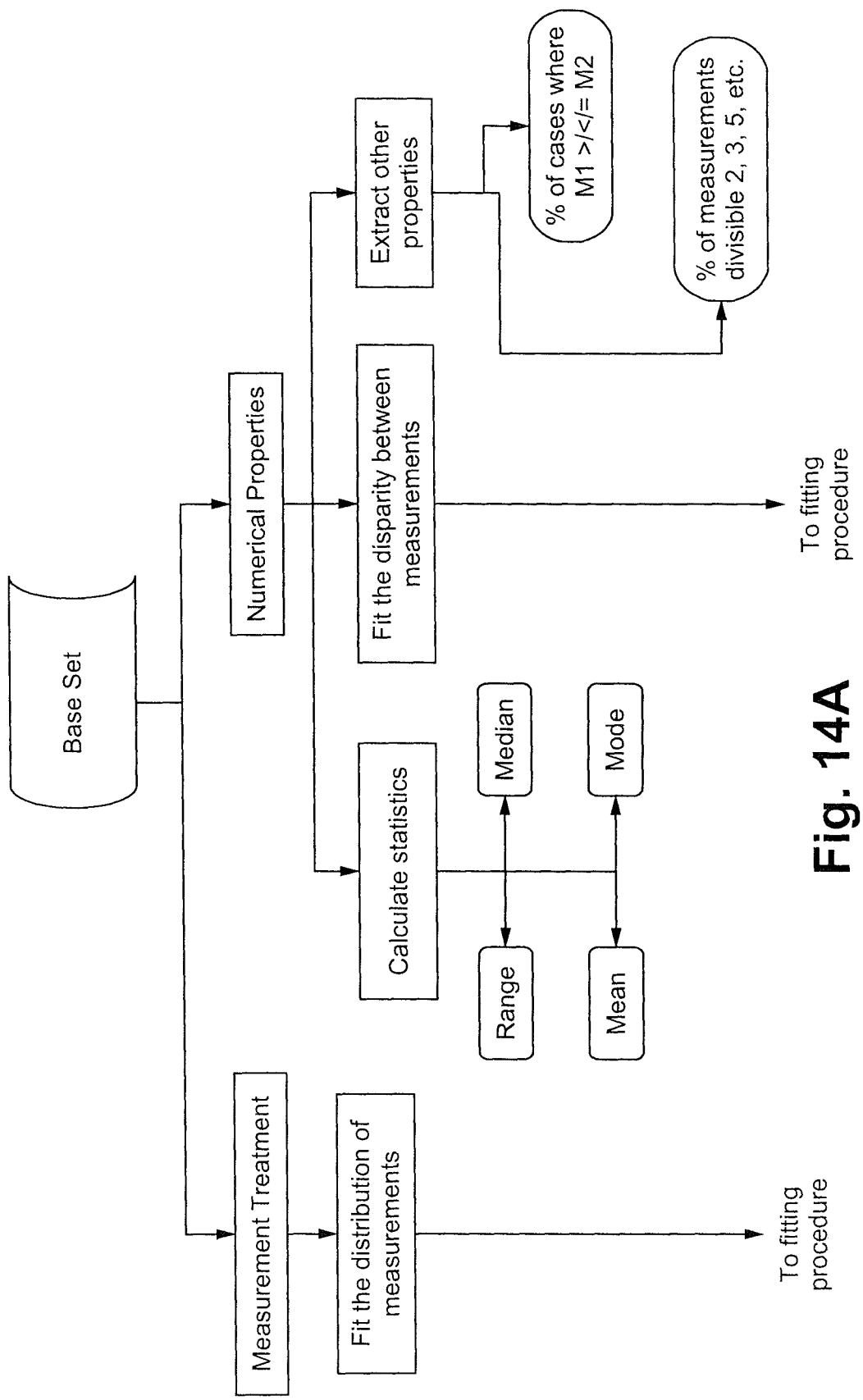
FIG. 14A illustrates a method of creating a characteristic base set for determining abnormal behavior within the impairment rating process in accordance with some embodiments.

This 'base set' shapes the data set and its numerical properties establish the 'characteristic profile' of the data. It is from the characteristic profile that abnormal data can be identified. FIG. 14A depicts the process of forming the characteristic profile within the overall Impairment Rating algorithm. Clinical users familiar with the objective collection of clinical data sets form this base set using standardized measurement devices. Base sets are formed for the specific purpose of serving as a representative sample of ROM data from which a characteristic profile is created.

Figure 14B:
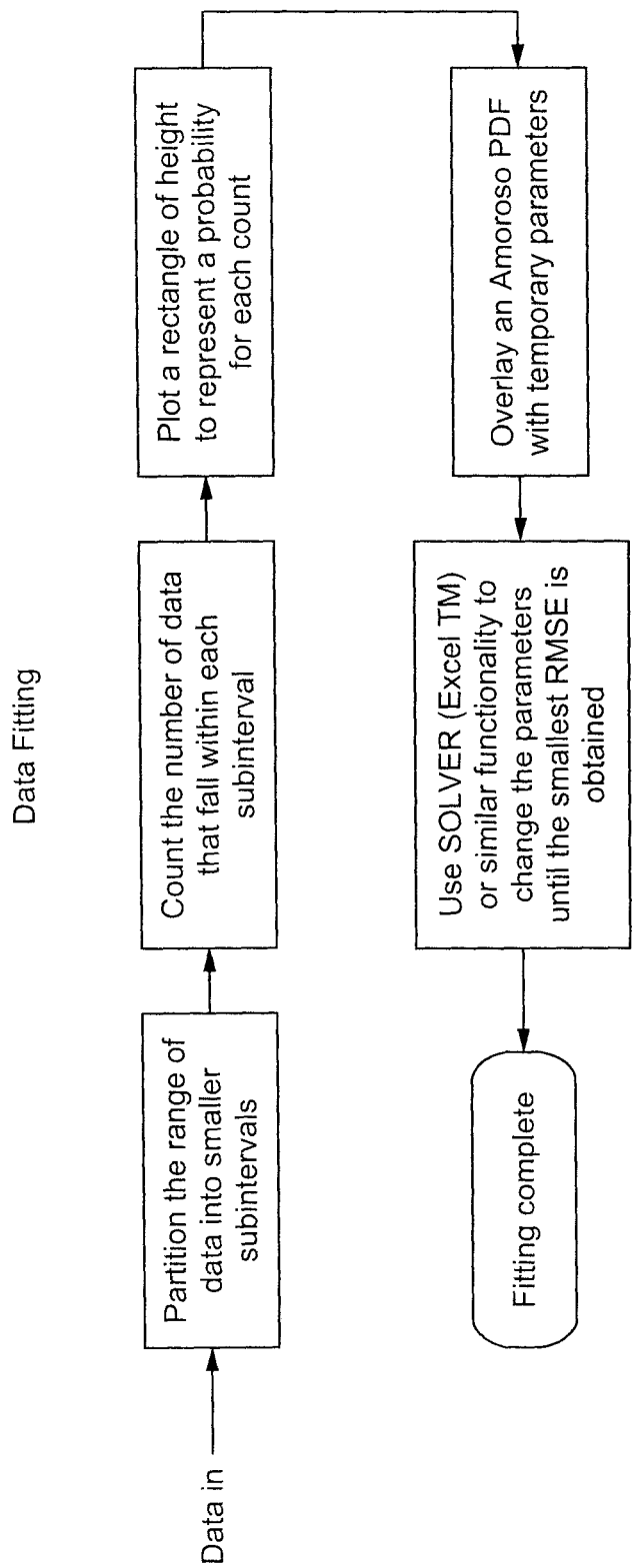
FIG. 14 B illustrates a method of fitting data to a base set for determining abnormal behavior within the impairment rating process in accordance with some embodiments.

Unique base sets are formed for each direction of motion, as each direction can have markedly different traits than others. Each base set engenders the formation of a characteristic profile, a rigorous statistical treatment of the data that falls within two broad classes. Firstly, a statistical model is assigned to the data. Additionally, numerical properties can be extracted from the base set and included in the characteristic profile. These properties include, but are not limited to: the disparity between measurements, inequality between multiple measurements within a single case, divisibility of measurements, range, mean, median, mode, skewness of data, among other representative properties. FIG. 14A depicts how and where these parameters are generated to then be used in the algorithm. FIG. 14B illustrates how the data is fit to the characteristic profile before the abnormal behavior can be defined.

In addition to the distribution of measurements and associated statistical model, a characteristic profile can include numerical considerations as shown in FIG. 14A. This can encompass many numerical properties, including: the disparity between measurements, inequality between multiple measurements within a single case, range, mean, median, mode, skewness of data, among other representative properties. The disparity between measurements considers the values an Examiner records for multiple assessments of the same direction of motion, measurements such as 155 and 157 both for right shoulder flexion would have a disparity of two. The inequality between multiple measurements would record whether a measurement was greater than, less than, or equal to previous and subsequent measurements within a single examination. Basic statistics like range, mean, median, and mode, and measures of skewness are calculated as well. These, among other methods, comprise the numerical properties of the characteristic profile.

Figure 18:
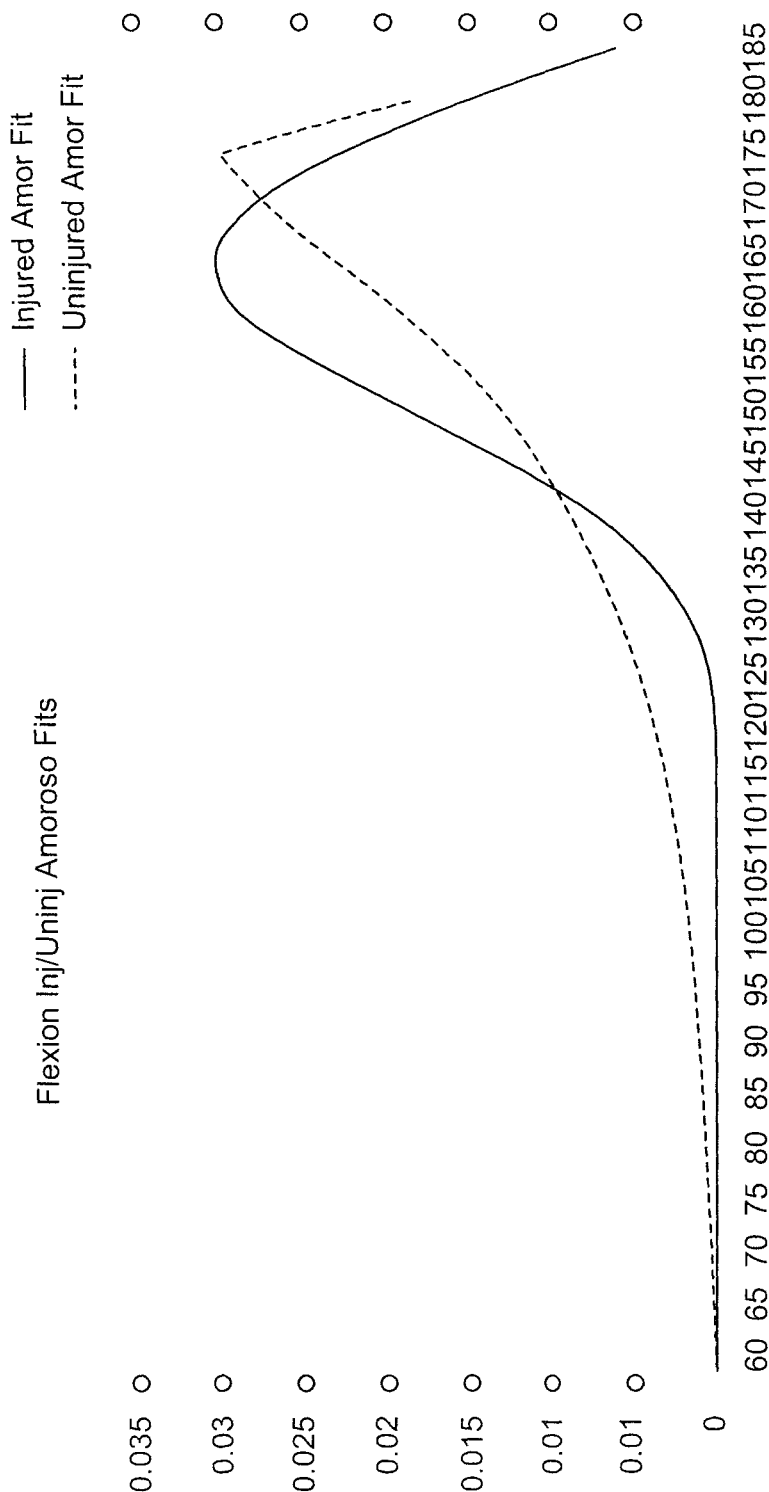
FIG. 18 illustrates a plurality of statistical models for shoulder flexion in accordance with some embodiments.

These two broad categories, the statistical model of the base set and its numerical properties, comprise the majority of the characteristic profile. For example, oftentimes the characteristic profiles of a direction of motion are different between those measurements taken on the injured or uninjured side of the body. This can be seen in FIG. 18, which shows that the statistical models for shoulder flexion are noticeably different.

Injured side, as well as other metrics, serves to better profile the data in the base set. FIG. 19 shows the distinction between injured and uninjured sides can be used in combination with other numerical properties.

Figure 15:
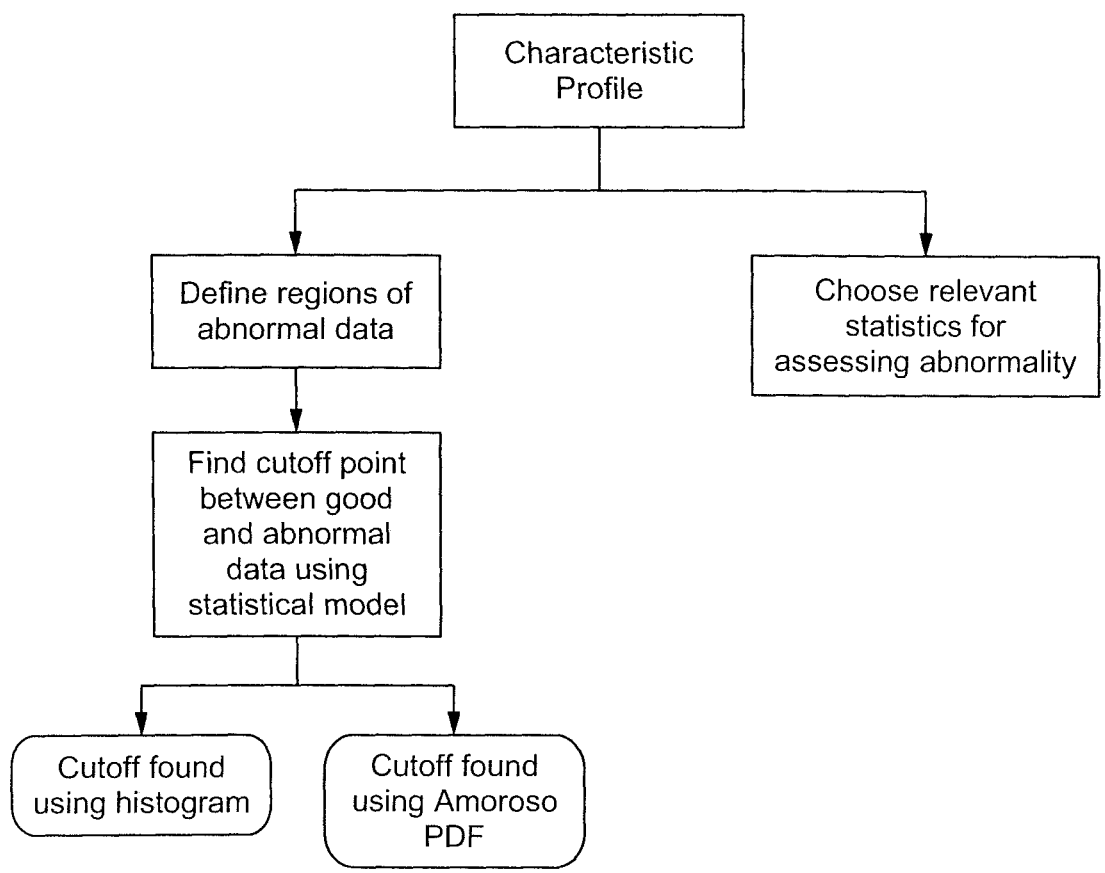
FIG. 15 illustrates a method of defining abnormal data for determining abnormal behavior within the impairment rating process in accordance with some embodiments.

With a characteristic profile for a given direction of motion, abnormal behavior can be defined, as shown in FIG. 15. Analysis can begin after assumptions are made as to the behavior of the data. This applies to the definition of abnormal behavior. Defining abnormal behavior involves both mathematical and medical considerations. Mathematical analysis provides many metrics by which similarity can be assessed, but a medical professional chooses representative metrics and defines acceptable data. These definitions can be updated at any time to improve functionality.

This flexibility avoids assuming the same behavior among data from all body parts. Any such limitation would hinder the algorithm's ability to detect data that differed from normal behavior, ultimately compromising utility.

Defining abnormal behavior begins with the distribution of measurements and the associated statistical model. From these, regions of statistically unlikely measurements (i.e. abnormal) can be defined. This definition process is done for each direction of motion as they can exhibit different regions of acceptable/unacceptable data.

In addition to the distribution of measurements, the numerical properties within a base set's characteristic profile can also be used to define abnormal data, as shown in FIG. 15. It is not unreasonable to assume different body parts' data are identifiable by different metrics. Thus, the process of selecting representative numerical properties is left to the discretion of a clinical expert.

Figure 12:
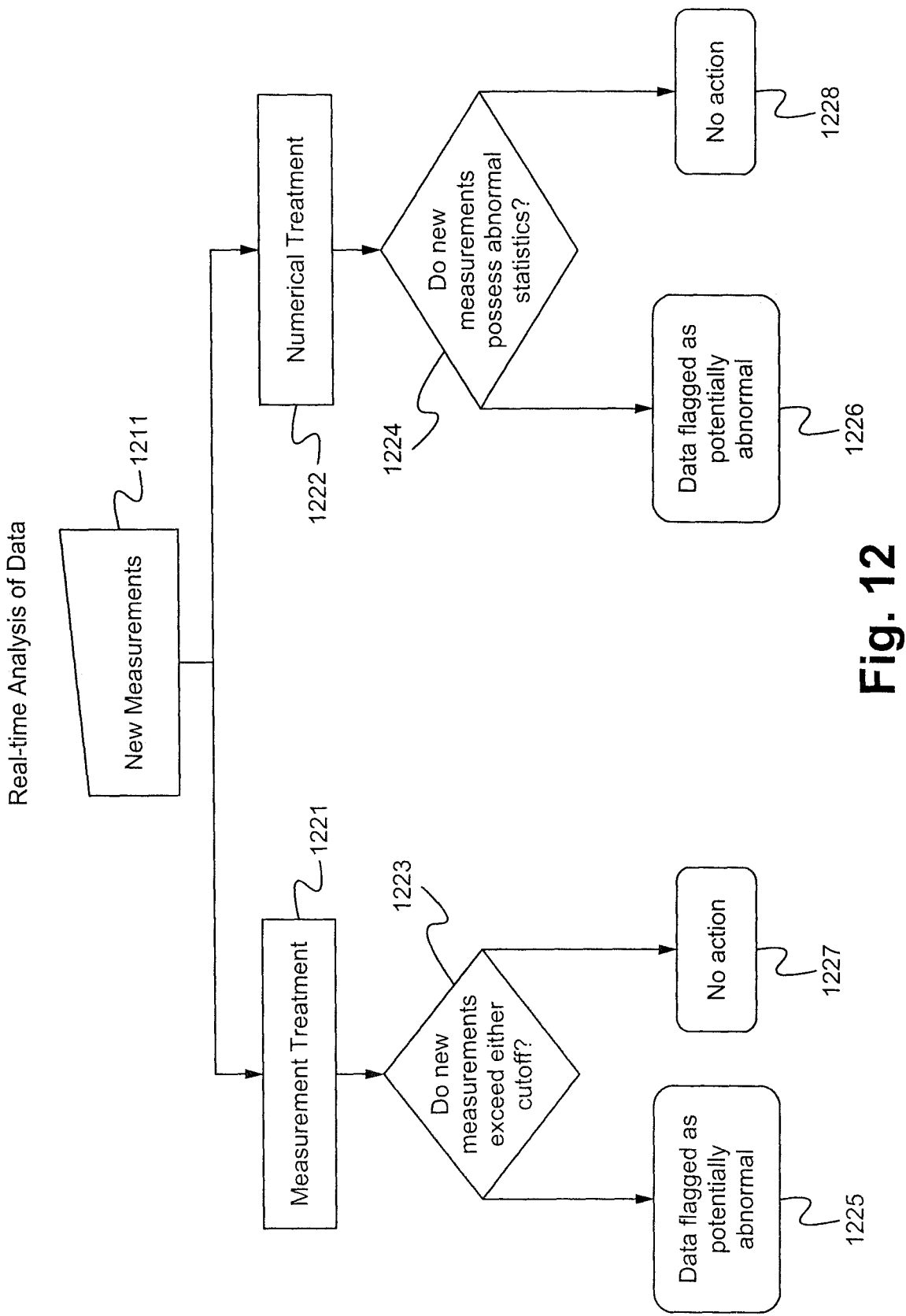
FIG. 12 illustrates a method of determining analyzing incoming data after abnormal behavior has been defined, in accordance with some embodiments.

With abnormal behavior defined, analysis of incoming data can begin. This analysis is performed in real time as the Examiner enters data during an examination, such as shown in FIG. 12. As measurements are made and entered, they are analyzed against the defined abnormal behavior of their respective direction of motion. That is, individual measurements are classified as valid or abnormal with respect to the cutoff values. Additionally, the numerical properties of the incoming data are compared with those of the characteristic profile to assess abnormality. If a measurement is identified as abnormal by either process, the case is flagged.

The new measurements 1211 are measured 1221 and numerically treated 1222. Based upon whether the measurements exceed a numerical cutoff 1223, the data is either flagged as potentially abnormal 1225 or no action is taken 1227. Additionally, based upon the numerical analysis it is determined whether the measurements possess abnormal statistics 1224 and the data can be flagged as potentially abnormal 1226 or no action is taken 1228.

The flagging process merely indicates whether or not the new measurements deviate from the characteristic profile. FIG. 13 depicts how to process the flagged and/or the unflagged data. As shown within FIG. 13, based upon the analyzed data 1313, it is determined whether the new measurements are abnormal 1330. If it is determined that the measurements are abnormal, then the Examiner can be notified 1333. Otherwise, the measurements can be included within the base set 1331. The measurements can also be saved in long term storage 1310.

Those cases left unflagged are considered similar to the characteristic profile, and a protocol is initiated for including them into the base set. Flagged cases are held separately for further consideration. In certain instances, a marked deviation can indicate a possible user error and the Examiner would be prompted to review their entries. Other cases could exhibit traits associated with fraud, other medical conditions in need of substantiation, or other factors. Regardless, all measurements being process are retained in long-term storage for further analysis.

Pattern Recognition Algorithm

Pattern recognition analysis is part of the real time audit of clinical data set generated during the examination. The pattern recognition analysis extends across data entries to determine if a sequence in the data exists. For example, within a single case measurements can all be divisible by five.

Patterns can take many forms, and this, like other facets of the invention, can be updated or adapted accordingly. This will allow RateFast to recognize new patterns. Common examples of these patterns can include, but are not limited to; 1) range-based, for example, an Examiner can enter measurements that are consistently X degrees apart, 2) divisibility, a sufficient number of measurements are divisible by 2, 3, 5, etc. can be considered anomalous, and 3) ordering, an Examiner can enter n, n+1, n+2 or n, n−1, n−2 for sufficiently many examinations.

These, among other patterns, are searched for within an Examiner's historic and current cases. While patterns can occur naturally due to randomness within a single case, patterns across multiple cases can cause a case to be flagged.

As described above, the composition of statistical modeling, pattern recognition, feedback to clinician, data retention and self-reporting method to assure accuracy and integrity to the final impairment rating. In operation, the method that teaches unique applications of statistical analysis to medical processes in order to assist in obtaining substantially improved accuracy of impairment ratings. This analysis is comprised of multiple components. First, a statistical model, evaluates the input data for anomalies or outliers. If none are found, the data proceeds into the impairment calculator. Second, an analysis for patterns in the data, which fall within the expected range, will also trigger an anomaly response. When an anomaly response is triggered, the clinician is queried as to the validity of the data just entered. Simultaneously, HIPPA compliant stakeholders retain the initially entered data for possible later audit.

Figure 17:
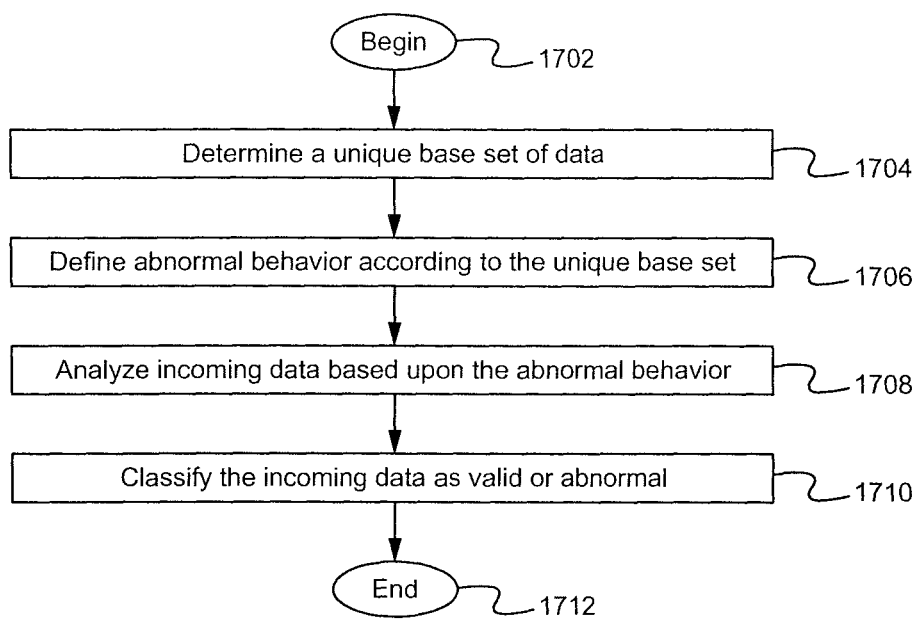
FIG. 17 illustrates a method of determining abnormal behavior within the impairment rating process in accordance with some embodiments.

FIG. 17 illustrates a method of determining abnormal behavior within the impairment rating process. The method begins in the step 1702. In the method 1704, a unique base set of data is determined and in the step 1706, abnormal behavior is defined according to the unique base set. In the step 1708, incoming data is analyzed based upon the abnormal behavior. Based upon the analyzed data, further incoming data is classified as either valid or abnormal in the step 1710. In some embodiments, the data can be analyzed according to a cutoff value. Additionally, a unique base set of data can be created for each direction of motion. The method ends in the step 1712.

The statistical model can be chosen based on its ability to accurately represent the historical medical data and assess the input data for patterns. Also, other numerical properties are extracted from the historical data. The model and related numerical properties are then used to evaluate the input data while the clinician is entering it. This 'real time' evaluation of the input data enables virtually immediate identification of patterns or values that deviate significantly from the expected ranges and their variability, i.e. abnormal data. These abnormal data, whether their origin is purposeful fraud, a mistake on behalf of an Examiner, equipment malfunction or just natural aberration, are noted and left for further review by the clinician and other parties. Hence, this analysis performs as an audit and feedback of the data quality to the clinician to assist in managing the integrity of the input data during the examination process to attain an accurate impairment rating.

As described above, the method teaches unique applications of logic and statistics to medical processes to obtain substantially improved accuracy in the measurement of an examinee's pathology due to an injury. These methods incorporate strict protocols, or "Administrative Rule Sets" to direct the examination for the purpose of obtaining an optimal, accurate and reproducible data set, from which a rating of the impairment due to the pathology resulting from an injury can be determined. These methods digitize the values obtained from a clinical evaluation of the examinee. These methods begin by characterizing the location and extent of the injuries (pathologies) then analyze the data for its variance and validity, as well as adjustments in the measurement method depending upon initial analysis.

This application of the established rule sets prior to the examination combined with hierarchical protocols or "Administrative Rule Sets" further enhance accuracy of determining the impairment rating in the event of multiple simultaneous injuries or pathologies present at the time of examination. This use of a strict set of protocols substantially reduces the variability due to personal bias on the part of the Examiner, as well as, real time verification of the exam values in the clinical visits. An anticipated use, amongst several, of this collection of methods is to obtain impairment ratings for Workers Compensation claims.

The collection of methods and system teach unique applications of logic and statistics to medical processes to obtain substantially improved accuracy in the measurement of a examinee's pathology due to an injury. These methods and the system incorporate strict protocols, or "Administrative Rule Sets" to direct the examination for the purpose of obtaining an optimal data set, from which a rating of the impairment due to the pathology resulting from an injury can be determined. Additionally, within this method and system, a statistical analysis can additionally assist in obtaining an improved accuracy of impairment ratings. Consequently, the errors in the impairment rating presently carried forward through the disability, care and compensation phases of the process are now avoided. As such, the method and system as described above, has many advantages.

The present invention has been described in terms of specific embodiments incorporating details to facilitate the understanding of the principles of construction and operation of the invention. Such references, herein, to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A method of constructing an apportionment of a permanent disability determination comprising:
    storing, in a database communicatively coupled with a server computer, a plurality of rating spreadsheets, wherein each rating spreadsheet of the plurality of rating spreadsheets is associated with an impairment and comprises logic that applies a plurality of criteria defined by a plurality of administrative rule sets for the impairment;
    receiving, by the server computer from a clinician computing device, an encrypted clinical data set including, for an injury, clinical data that is defined according to the plurality of administrative rule sets, the clinical data validated by a shell program executing on the clinician computing device as authentic based on the plurality of the administrative rule sets, wherein the shell program controls a graphical user interface on the clinician computing device to guide a user using the clinician computing device through prompts to enter the clinical data according to the plurality of administrative rule sets;
    decrypting, by the server computer, the encrypted clinical data set to obtain the clinical data;
    selecting, by the server computer, based on the injury, a particular rating spreadsheet from the plurality of rating spreadsheets;
    importing, by the server computer, the clinical data into one or more fields of the particular rating spreadsheet, wherein the particular rating spreadsheet applies a plurality of criteria for the injury, as defined by the plurality of administrative rule sets, to determine an impairment value for the injury;
    identifying, by the server computer, one or more functional activity limitations based on a permanent impairment;
    separately identifying, by the server computer, one or more non-industrial contributors and factors of the one or more functional activity limitations based on the permanent impairment;
    subtracting, by the server computer, an apportionment percentage of each of the one or more functional activity limitations from the injury;
    assigning, by the server computer, a weighted apportionment of the one or more functional activity limitations;
    assigning, by the server computer, final percentage contributions of the one or more functional activity limitations to apportion a final claim benefit for the injury;
    generating, by the server computer, a clinical report from the final claim benefit and formatting, by the server computer, the clinical report according to stakeholder requirements;
    encrypting the formatted clinical report and transmitting the encrypted clinical report to at least one of a patient computing device and an electronic health record computing device.

2. The method of claim 1, wherein the one or more functional activity limitations restrict one or more activities of daily living.

3. The method of claim 1, wherein the one or more functional activity limitations are represented by pain, organ and body system loss.

4. The method of claim 1, wherein the one or more non-industrial contributors comprise one of a pre-existing injury and a non-work related injury.

5. The method of claim 1, wherein the permanent disability determination is based on the plurality of administrative rule sets for the injury.

6. The method of claim 1, wherein one or more of the final percentage contributions of the one or more functional activity limitations are usable to apportion stakeholder liability.

* * * * *